(12) United States Patent
Robin et al.

(10) Patent No.: US 10,150,776 B2
(45) Date of Patent: Dec. 11, 2018

(54) HARRINGTONINES SALTS IN THE CRYSTALLINE STATE AND THEIR USE FOR THE PURIFICATION OF THE CORRESPONDING DRUG SUBSTANCE

(71) Applicants: Jean-Pierre Robin, Geneva (CH); Nina Radosevic, Geneva (CH); Julie Blanchard, Puyricard (FR); Thierry Roisnel, Thorigne-Fouillard (FR); Thierry Bataille, Thorigne-Fouillard (FR)

(72) Inventors: Jean-Pierre Robin, Geneva (CH); Nina Radosevic, Geneva (CH); Julie Blanchard, Puyricard (FR); Thierry Roisnel, Thorigne-Fouillard (FR); Thierry Bataille, Thorigne-Fouillard (FR)

( * ) Notice: Subject to any disclaimer, the term of this patent is extended or adjusted under 35 U.S.C. 154(b) by 0 days.

(21) Appl. No.: 15/109,254

(22) PCT Filed: Dec. 30, 2014

(86) PCT No.: PCT/EP2014/079456
§ 371 (c)(1),
(2) Date: Jun. 30, 2016

(87) PCT Pub. No.: WO2015/101628
PCT Pub. Date: Jul. 9, 2015

(65) Prior Publication Data
US 2016/0333023 A1     Nov. 17, 2016

Related U.S. Application Data

(60) Provisional application No. 61/941,723, filed on Feb. 19, 2014, provisional application No. 61/922,248, filed on Dec. 31, 2013.

(51) Int. Cl.
*C07D 491/147* (2006.01)
*C07D 491/14* (2006.01)

(52) U.S. Cl.
CPC ....... *C07D 491/147* (2013.01); *C07D 491/14* (2013.01)

(58) Field of Classification Search
CPC .................. C07D 491/147; C07D 491/14
See application file for complete search history.

(56) References Cited

U.S. PATENT DOCUMENTS 7,842,687 B2 * 11/2010 Robin .................... C07C 57/13
                                                  514/214.01
2005/0090484 A1    4/2005 Robin et al.
2006/0234999 A1 * 10/2006 Robin .................... C07C 57/13
                                                  514/214.03

FOREIGN PATENT DOCUMENTS

| WO | 02074314 A1   | 9/2002  |
|----|---------------|---------|
| WO | 02074776 A2   | 9/2002  |
| WO | 2009148654 A2 | 12/2009 |

OTHER PUBLICATIONS

Stahl et al. List of Pharmaceutical salts (2002), Handbook of Pharmaceutical salts: Wiley—VCH—VHCA.*
(Continued)

*Primary Examiner* — Yong L Chu
(74) *Attorney, Agent, or Firm* — Cantor Colburn LLP

(57) ABSTRACT

The present disclosure concerns harringtonines salts at the crystalline state exhibiting a protonated nitrogen seen in solid state analysis and having general formula 1,

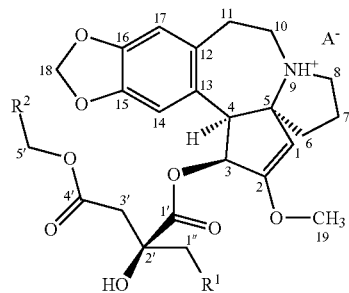

FORMULA 1 comprising solvates, made by reacting a cephalotaxine ester alkaloid base having formula 2,

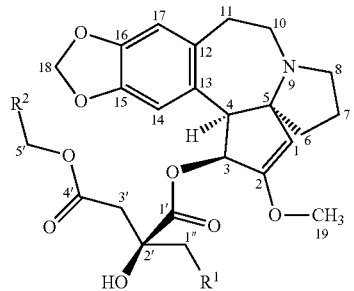

FORMULA 2 in which R1 is, but not limited to, alkyl, aryl, cycloalkyl, heteroalkyl, heteroaryl or heterocycloalkyl, and R2 is, independently, but not limited to H, alkyl, aryl, cycloalkyl, heteroalkyl, heteroaryl or heterocycloalkyl, with an acid having general formula AH in a non-aqueous crystallization solvent, wherein the said salt has a large water solubility. The disclosure is also related to a process for preparing and purifying these salts and their use as chemotherapeutic drugs.

17 Claims, 50 Drawing Sheets

(56) References Cited

OTHER PUBLICATIONS

International Search Report for International Application No. PCT/EP2014/079456; International Filing Date Dec. 30, 2014; dated May 13, 2015; 6 pages.
Kantarjian et al. "Cancer Drugs in the United States: Justum Pretium—The Just Price", Journal of Clinical Oncology, vol. 31, No. 28, Oct. 1, 2013, 5 pages.
Written Opinion for International Application No. PCT/EP2014/079456; International Filing Date Dec. 30, 2014; dated May 13, 2015; 14 pages.
Caira "Crystalline Polymorphism of Organic Compounds"; Topics in Current Chemistry; 1998; pp. 163-208; XP001156954.

* cited by examiner

FIGURE 1.1:
IR SPECTRUM OF HOMOHARRINGTONINE (BASE ALKALOID)
i. IR (ATR) spectrum in the crystalline state
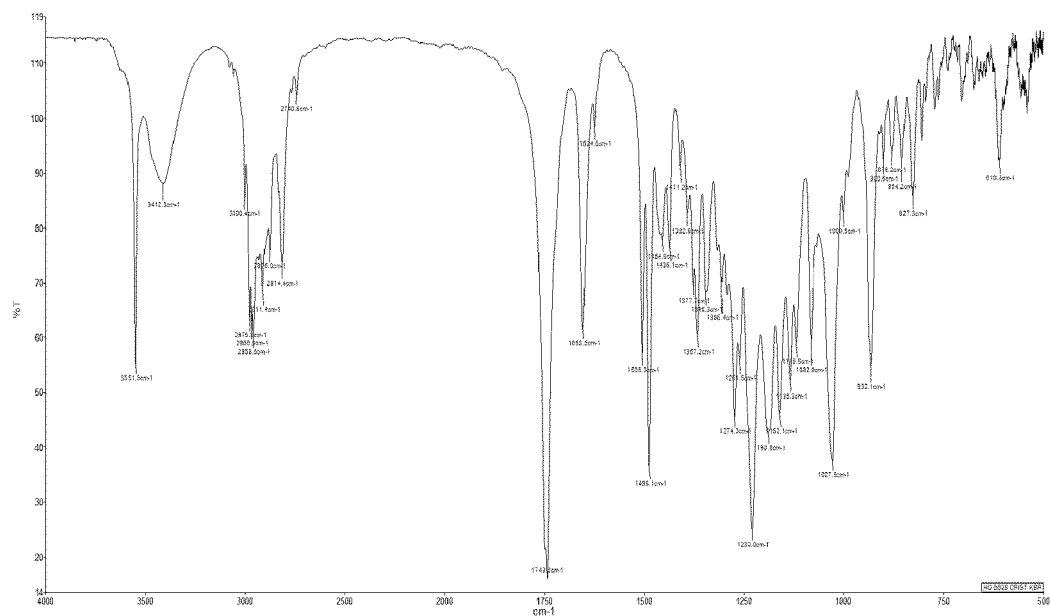
ii. IR (ATR) spectrum in the amorphous state
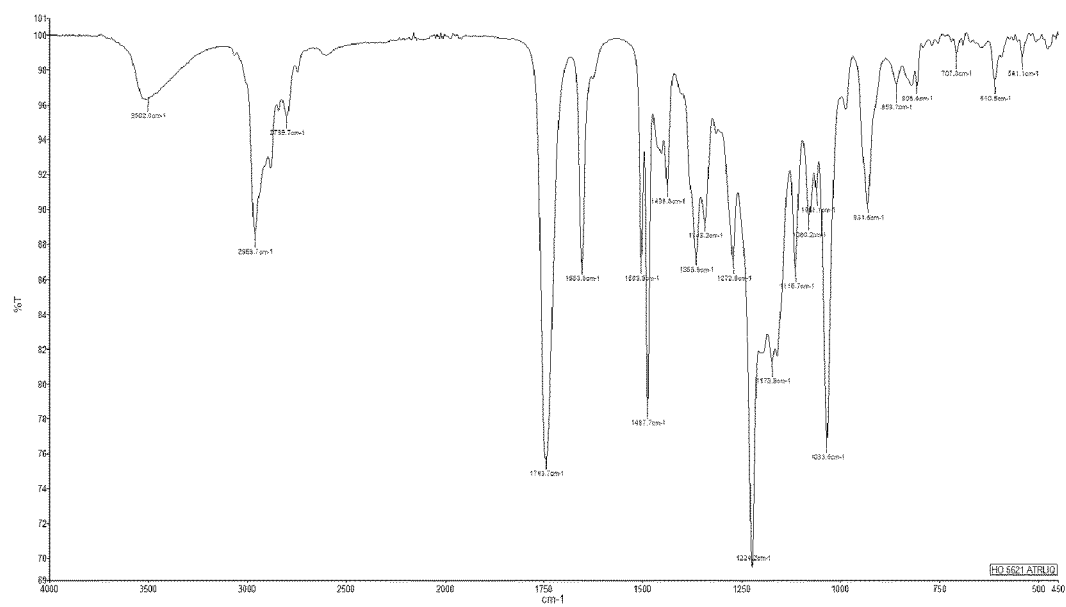

FIGURE 1.2: IR spectrum of homoharringtonine hydrogen (S)-malate in the solid state.
i. IR (ATR) spectrum in the crystalline state
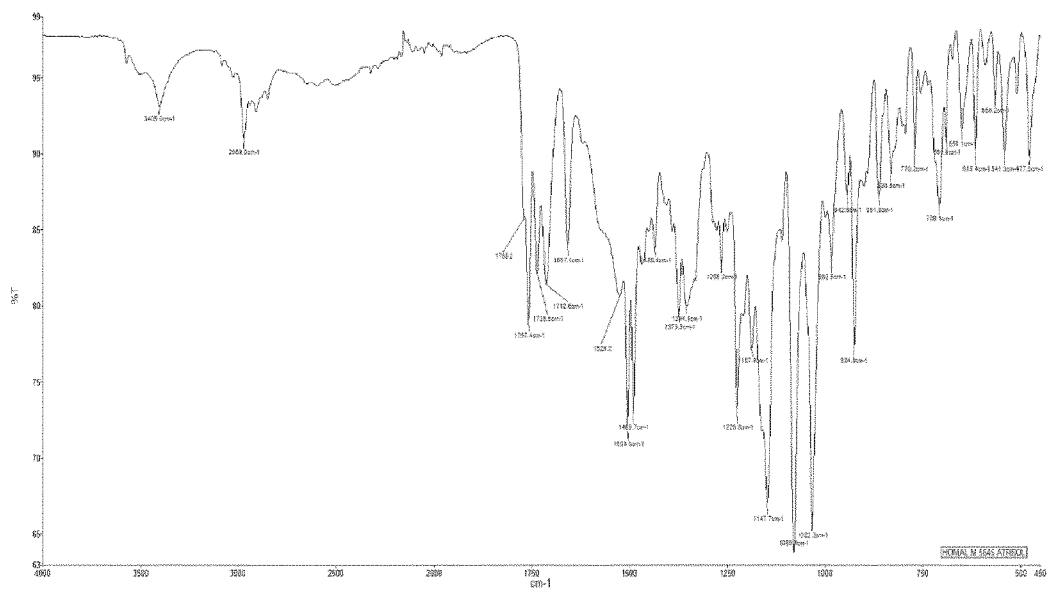
ii. IR (ATR) spectrum in the amorphous state (film)
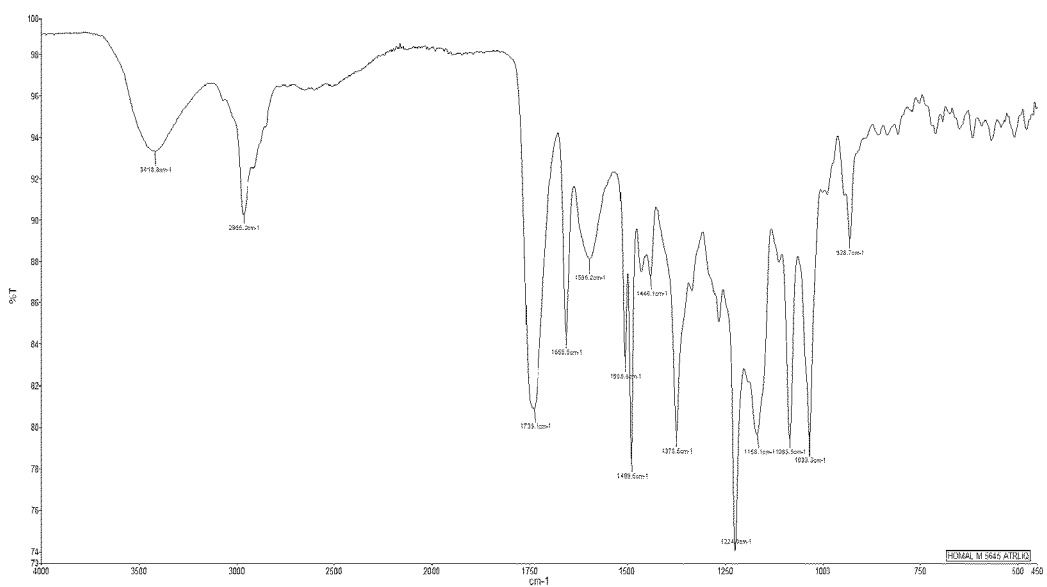

FIGURE 1.3: IR spectrum of homoharringtonine hydrogen (R)-malate in the solid state.
i. IR (ATR) spectrum in the crystalline state
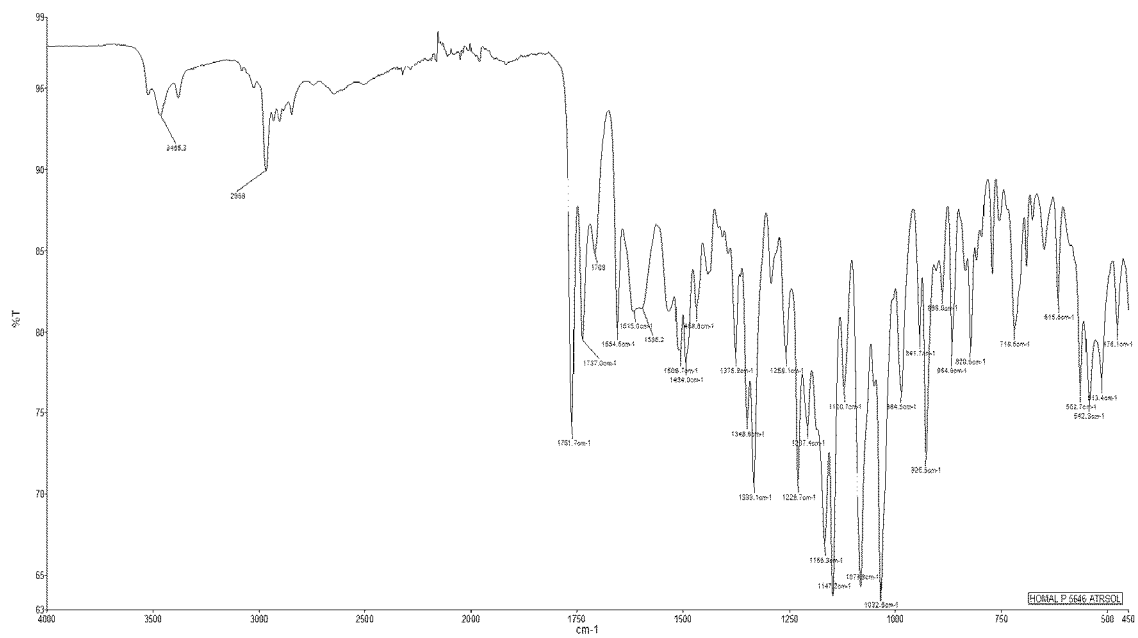
ii. IR (ATR) spectrum in the amorphous state (film)
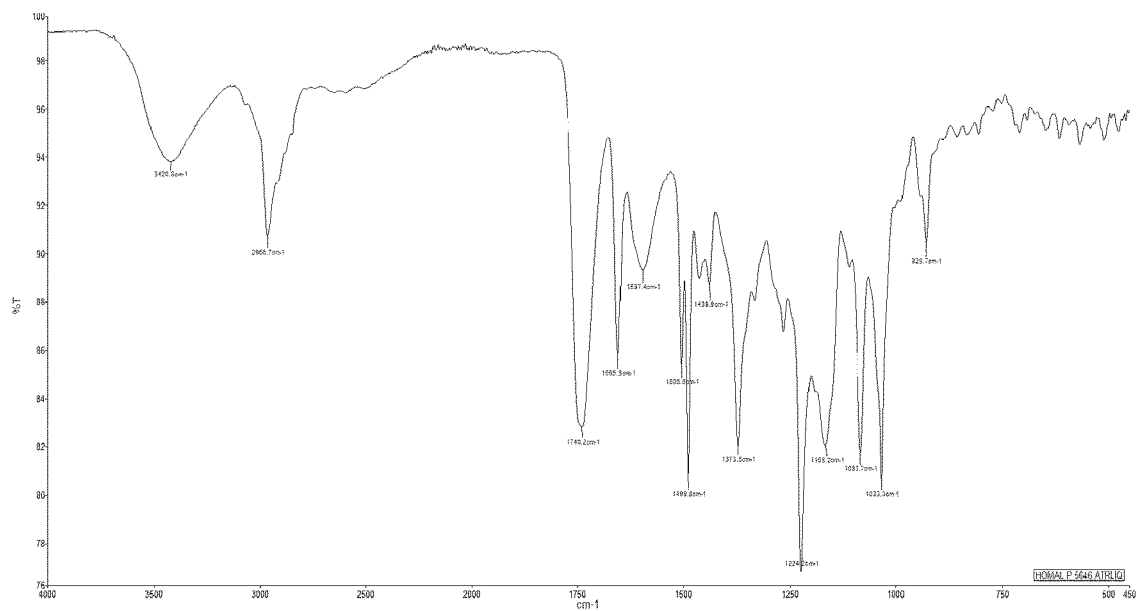

FIGURE 1.4: IR spectrum of homoharringtonine hydrogen (2S,3S)-tartrate in the solid state.
i)     IR (ATR) spectrum in the crystalline state
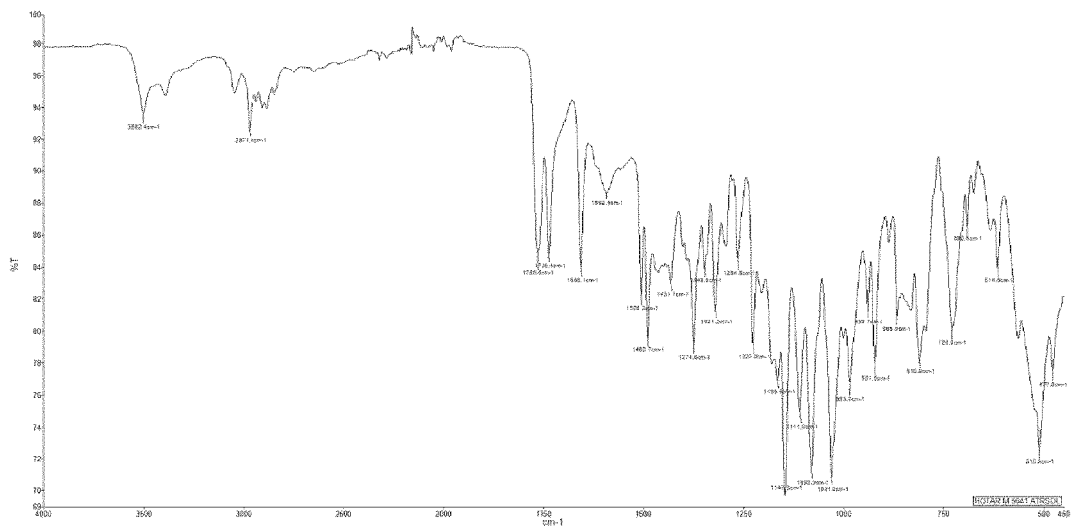
ii)     IR (ATR) spectrum in the amorphous state (film)
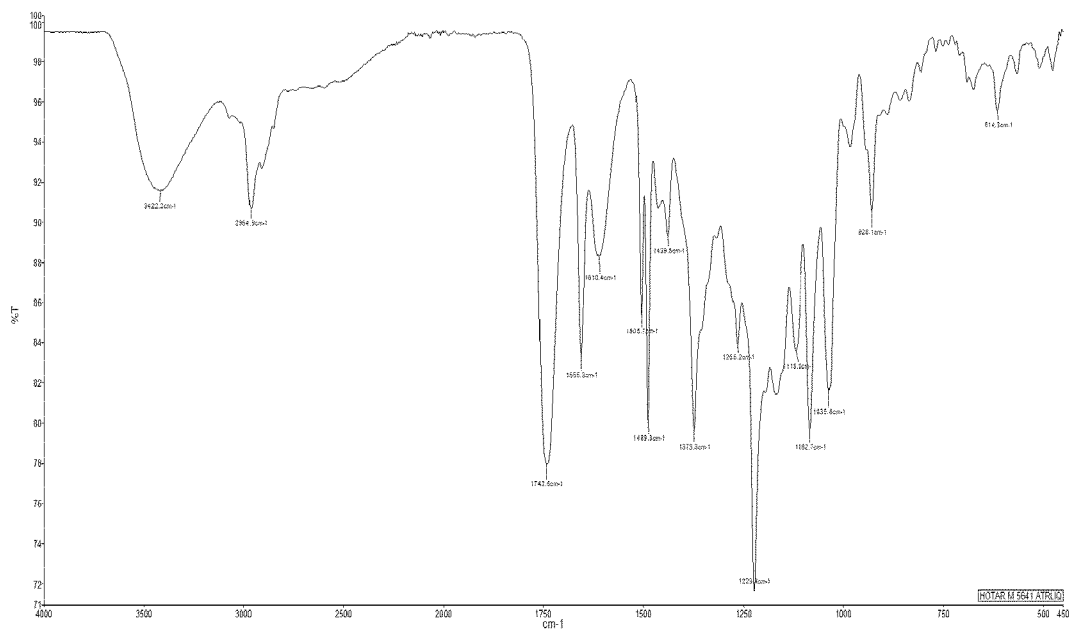

FIGURE 1.5: IR spectrum of homoharringtonine hydrogen (2R,3R)-tartrate in the solid state.
i) IR (ATR) spectrum in the crystalline state
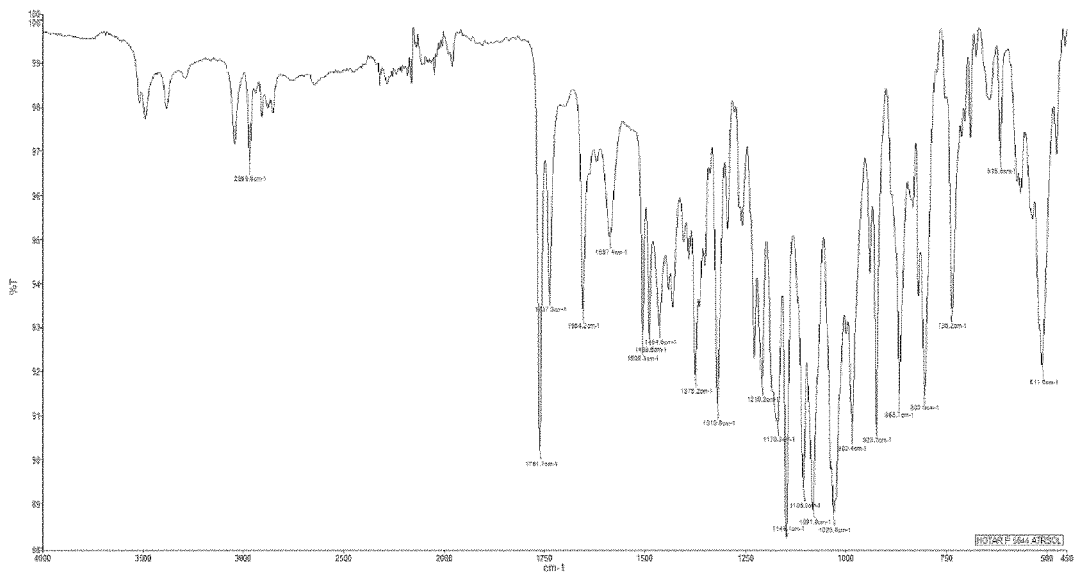
ii) IR (ATR) spectrum in the amorphous state (film)
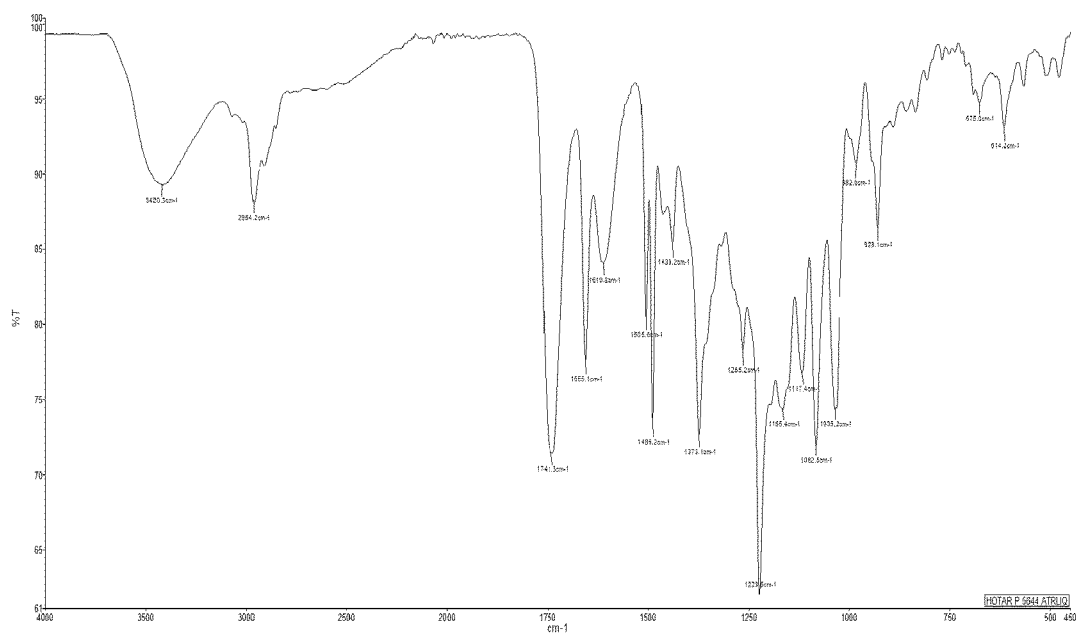

FIGURE 1.6: IR of homoharringtonine hydrogen (2'''S)-citramalate in the solid state.
i) IR (ATR) spectrum in the crystalline state
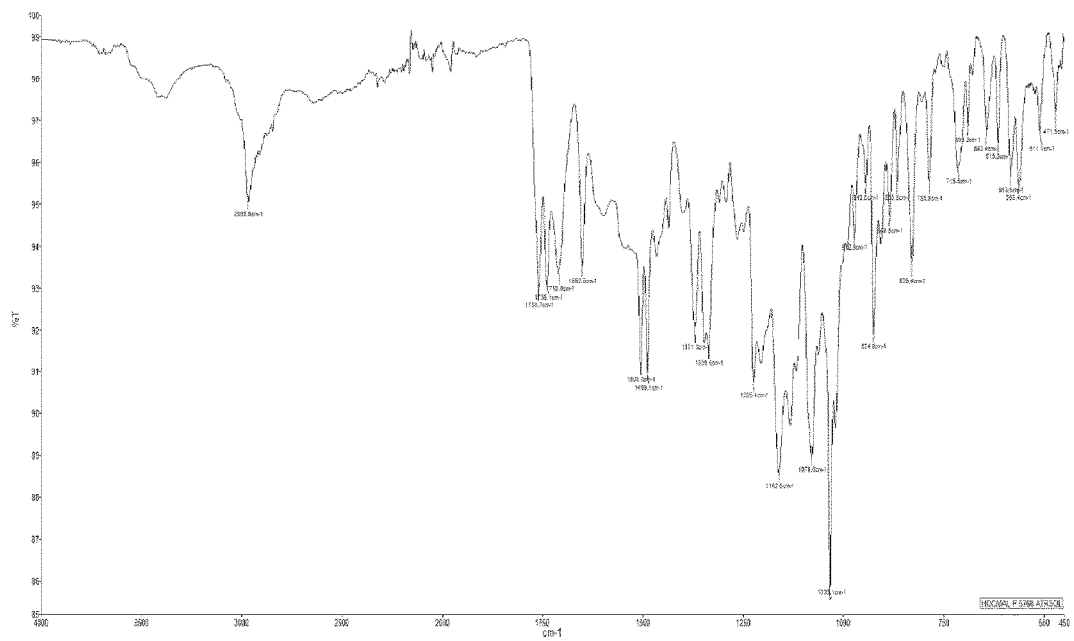
ii) IR (ATR) spectrum in the amorphous state (film)
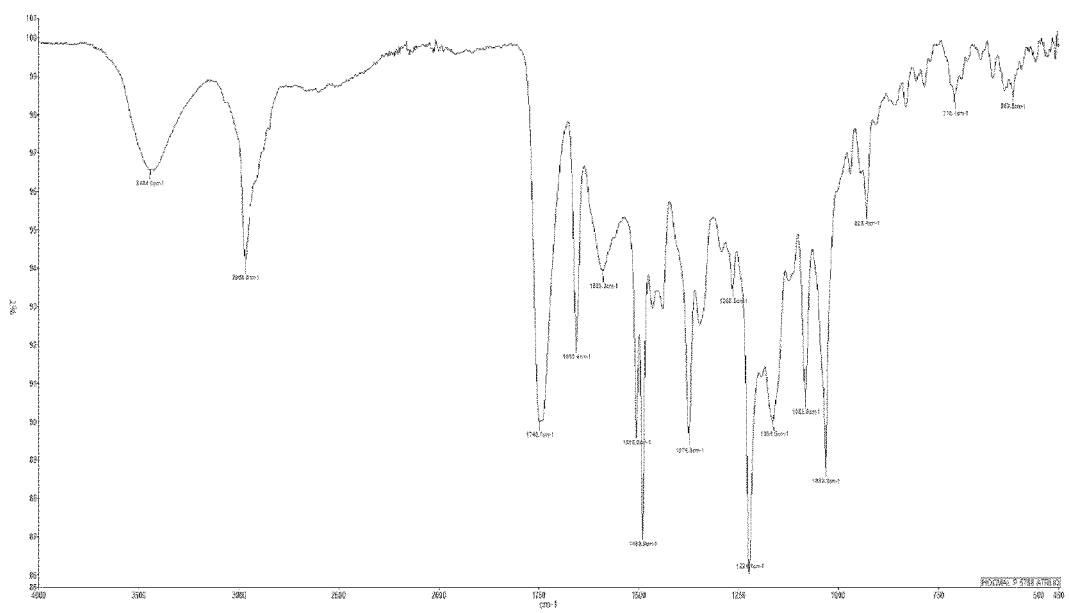

FIGURE 1.7: IR of homoharringtonine hydrogen (2'''R)-citramalate in the solid state.
i) IR (ATR) spectrum in the crystalline state
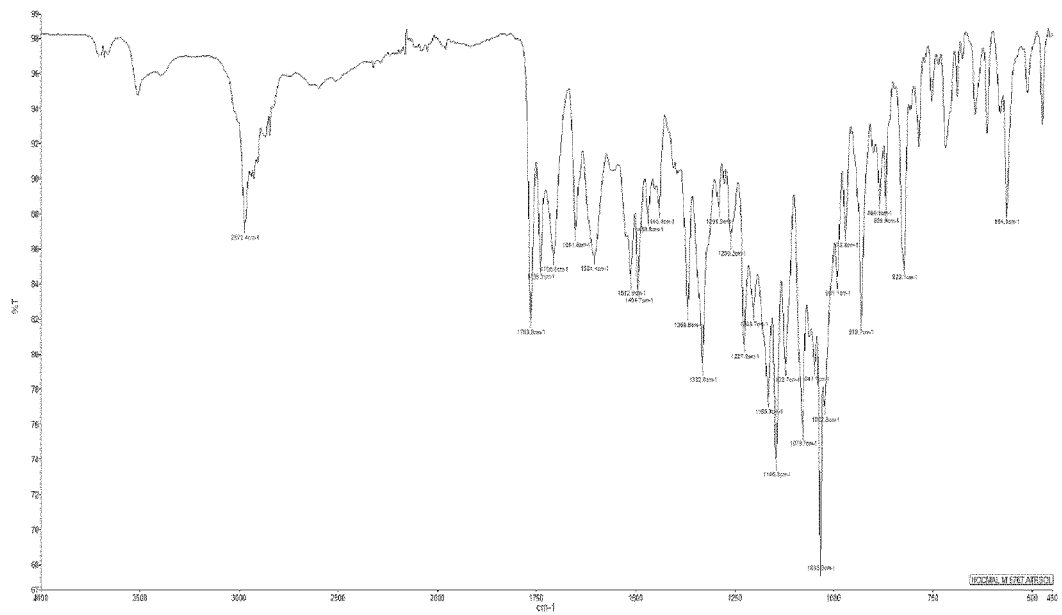
ii) IR (ATR) spectrum in the amorphous state (film)
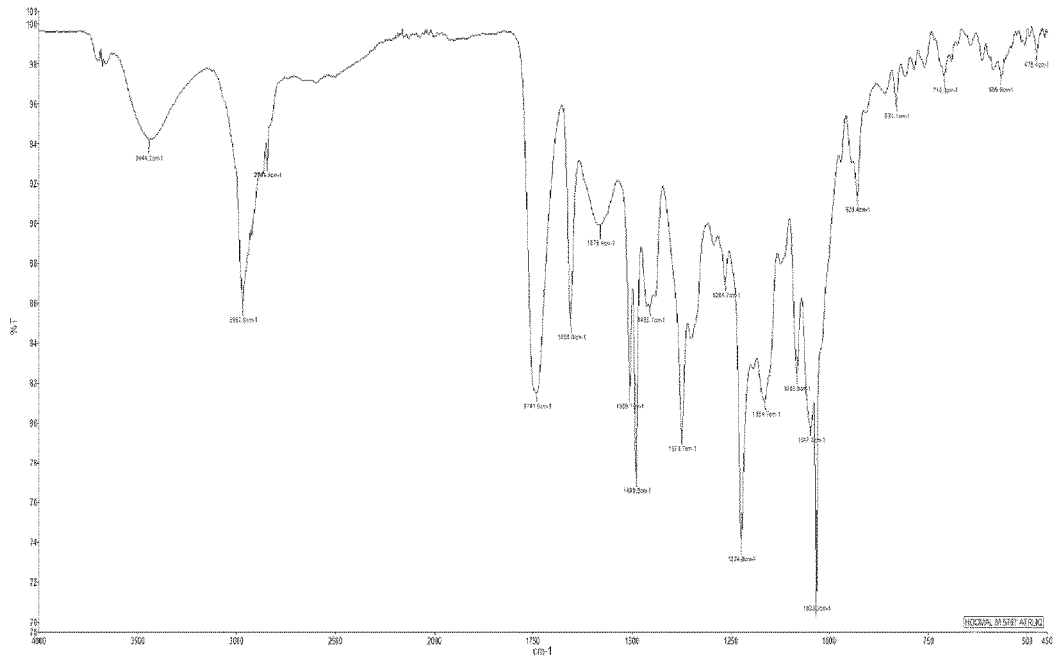

FIGURE 1.8: IR of homoharringtonine hydrogen succinate.
i) IR (ATR) spectrum in the crystalline state
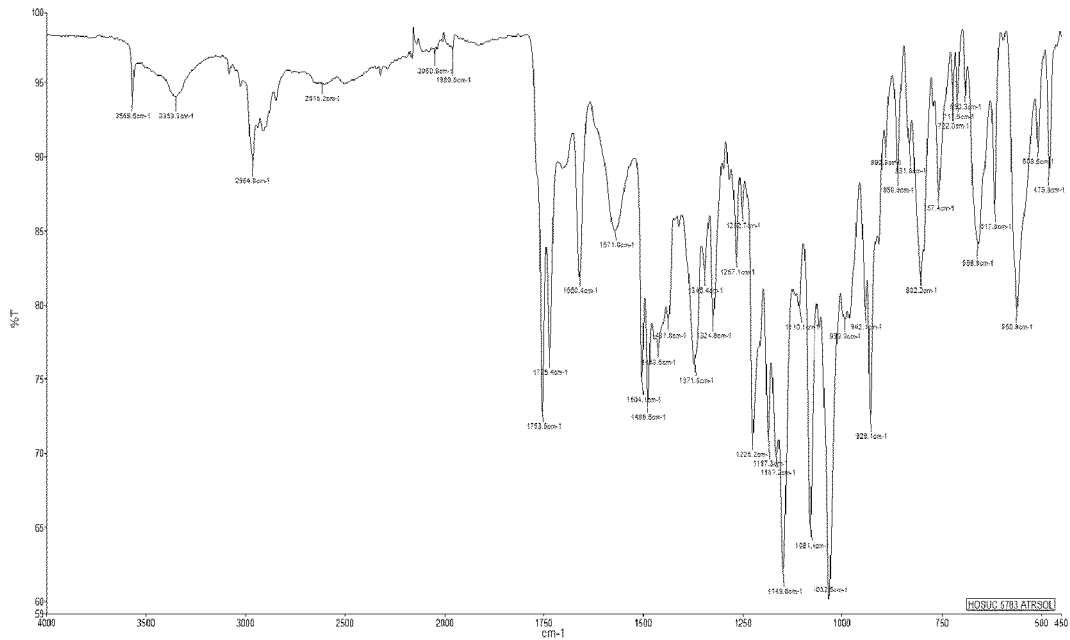
ii) IR (ATR) spectrum in the amorphous state (film)
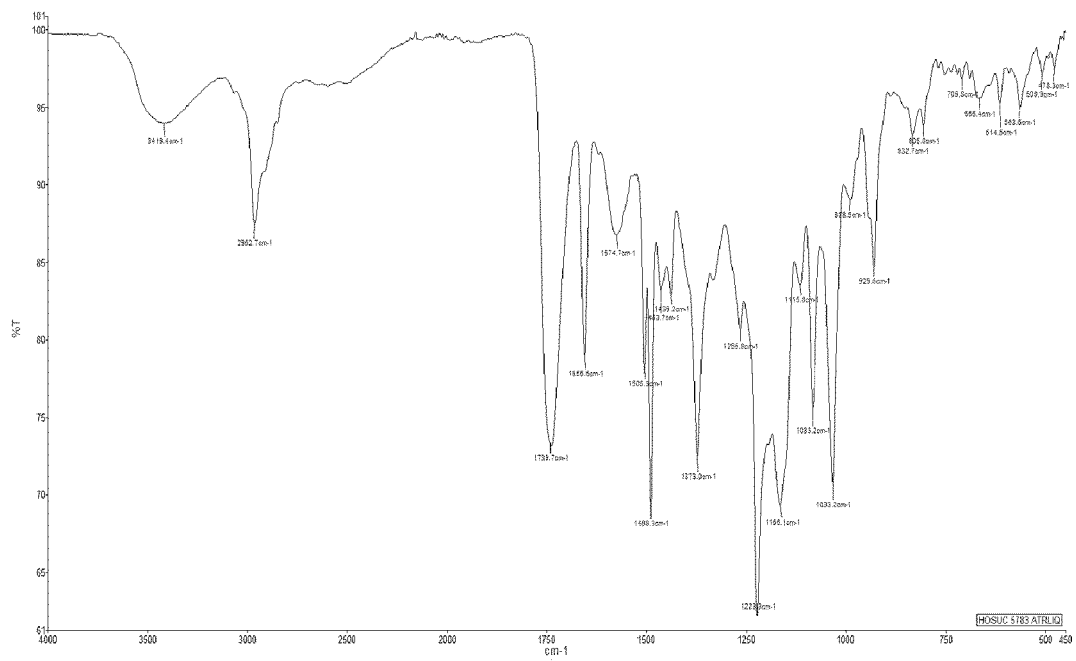

FIGURE 1.9: IR of homoharringtonine hydrogen itaconate in the solid state.
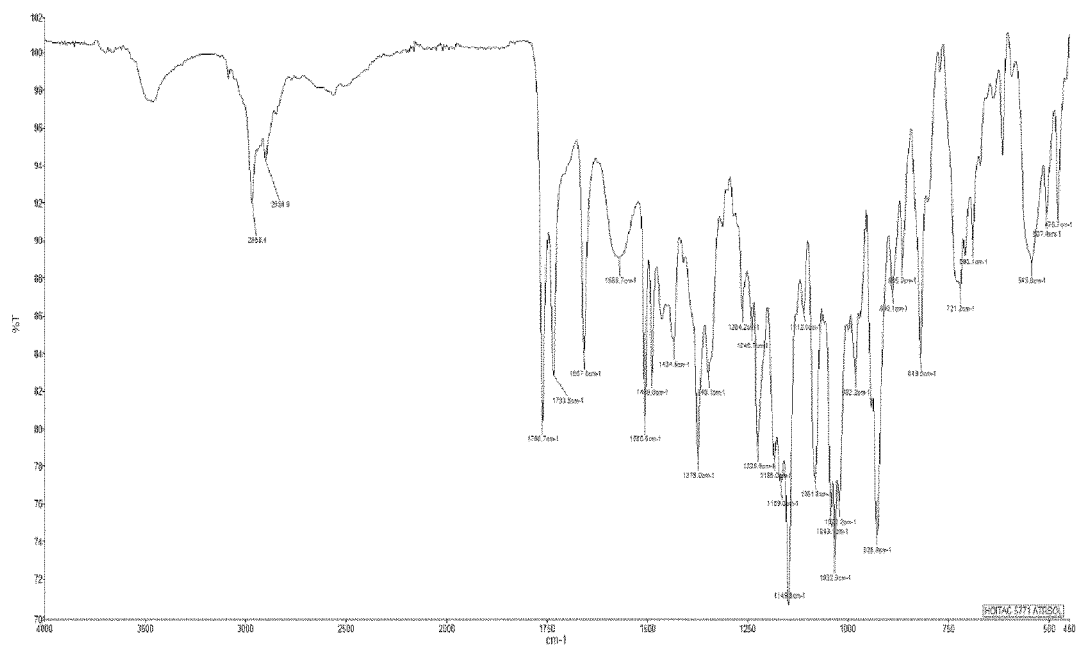
i)     IR (ATR) spectrum in the crystalline state
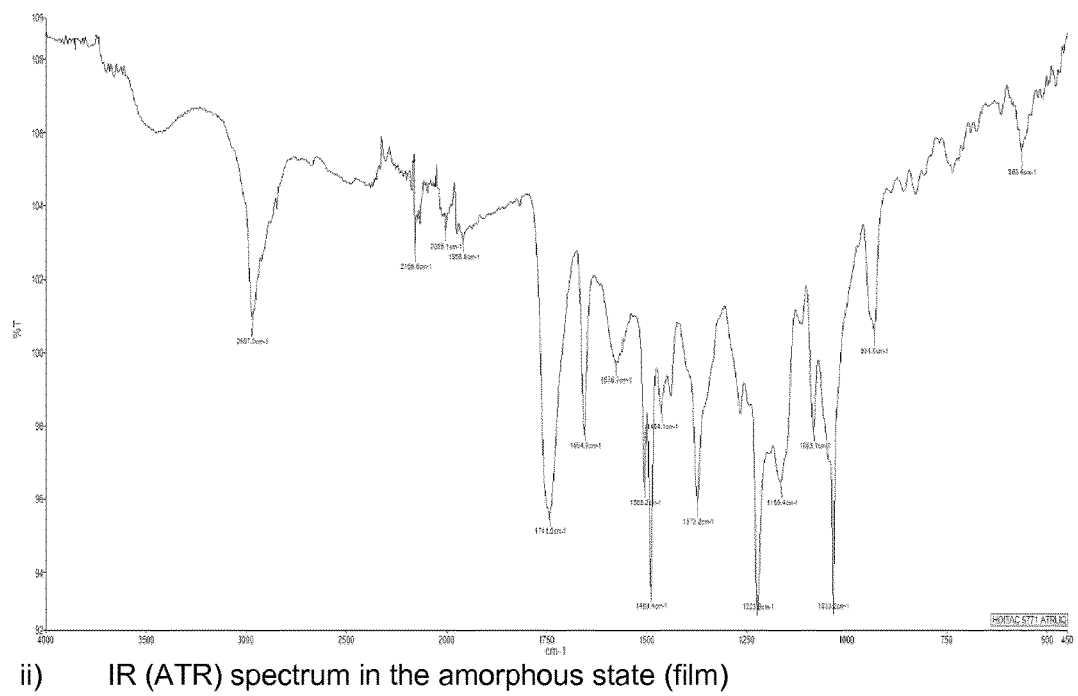
ii)     IR (ATR) spectrum in the amorphous state (film)

FIGURE 1.10: IR of the salt named homoharringtonine hydrogen fumarate at the solid state.
i) IR (ATR) spectrum in the crystalline state
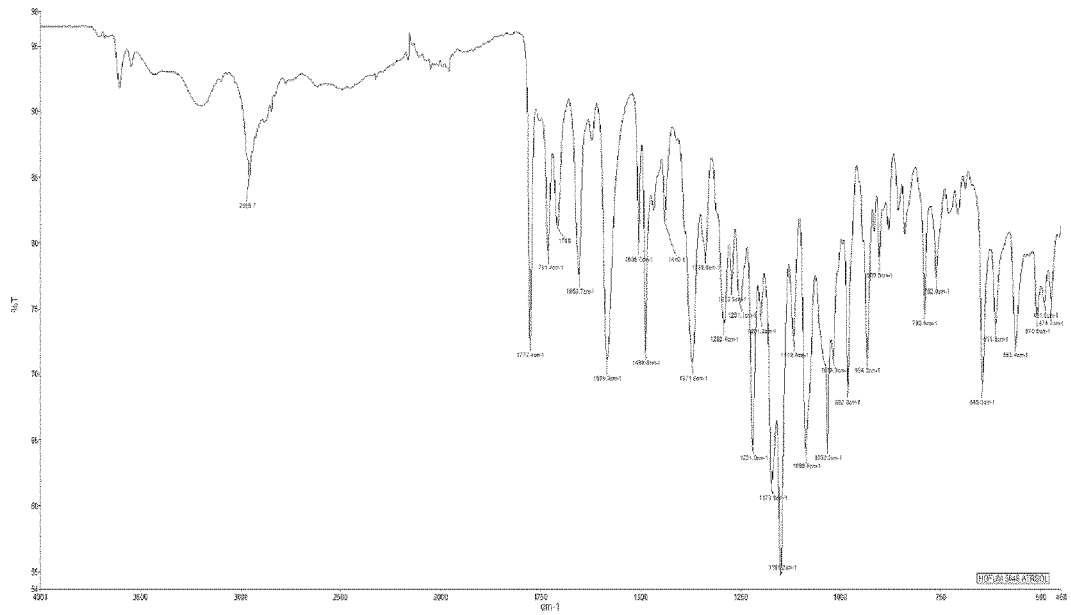
ii) IR (ATR) spectrum in the amorphous state (film)
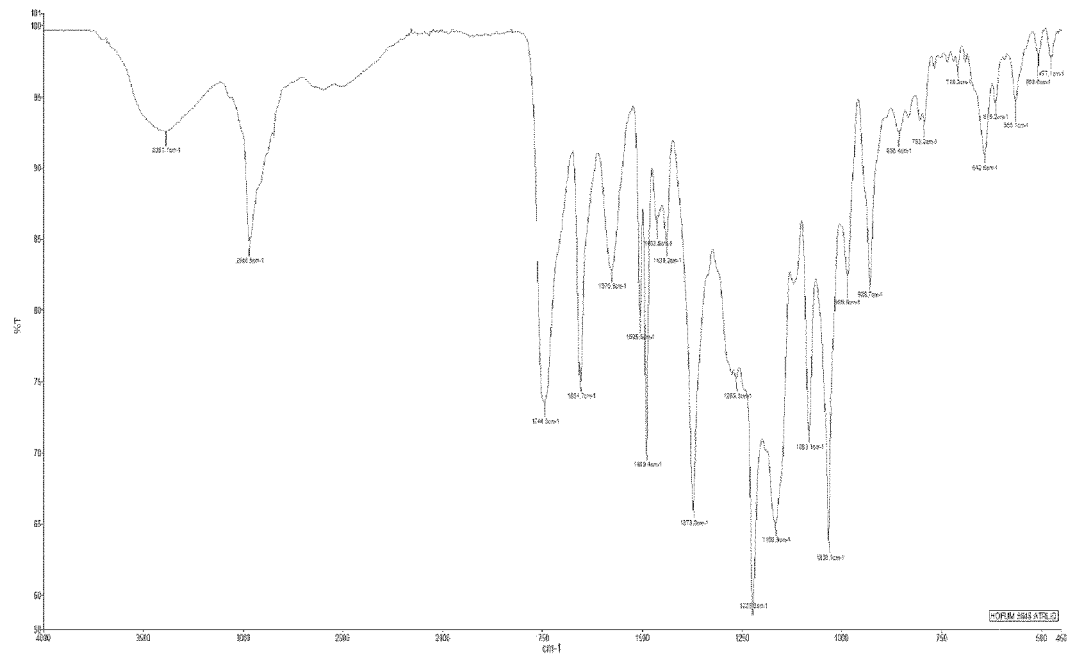

FIGURE 1.11: IR of homoharringtonine hydrogen tartronate in the solid state.
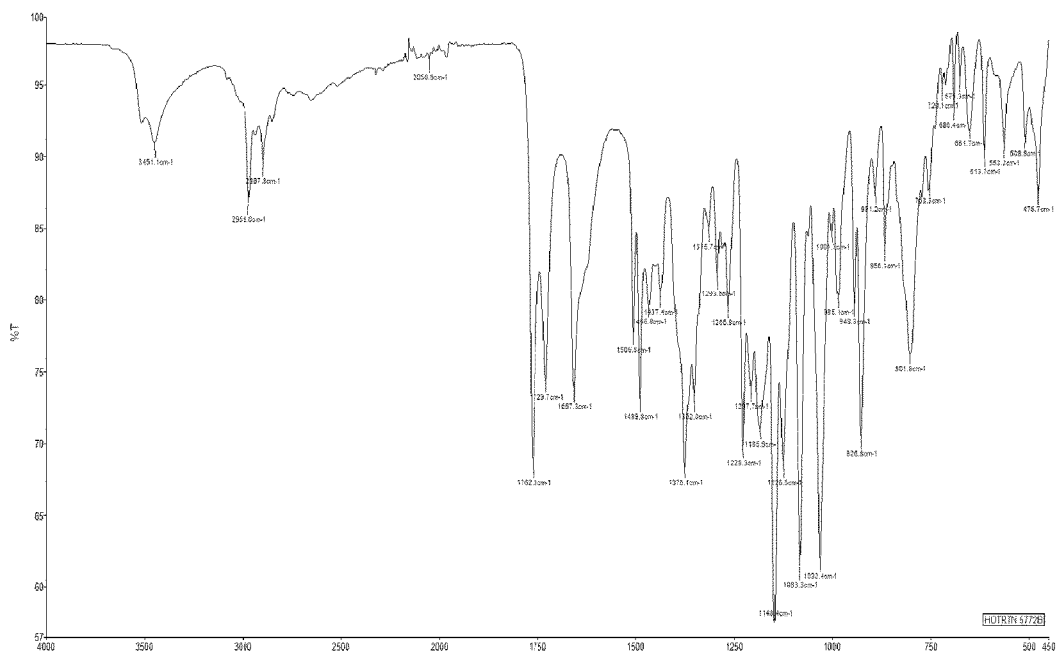
i) IR (ATR) spectrum in the crystalline state
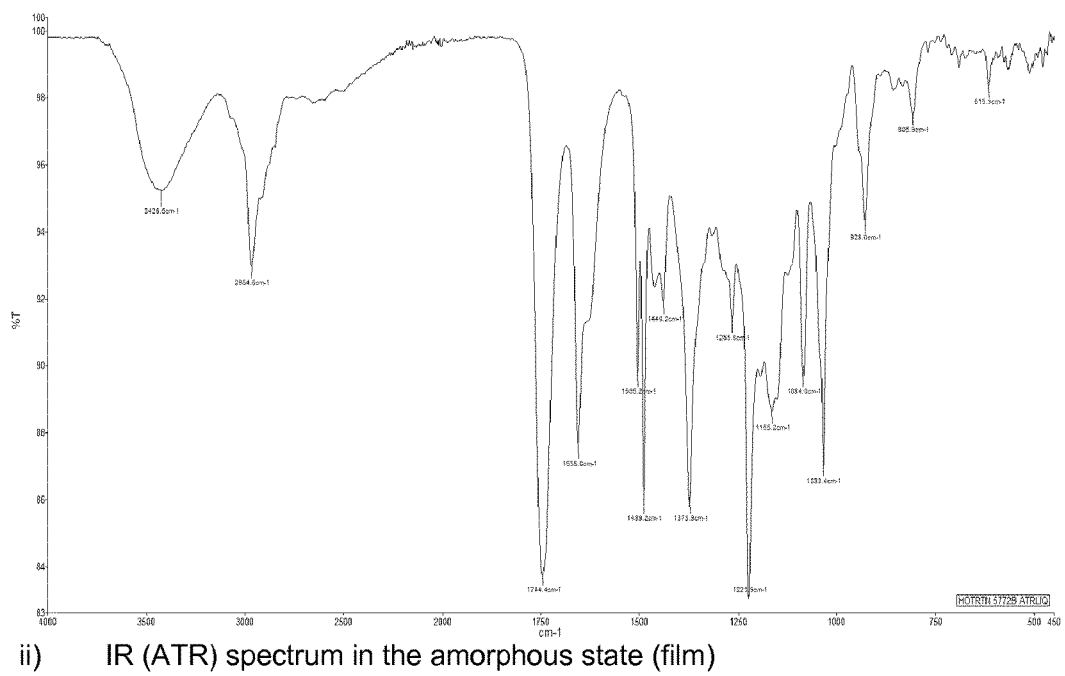
ii) IR (ATR) spectrum in the amorphous state (film)

FIGURE 1.12: IR of homoharringtonine malonate in the solid state.
i) IR (ATR) spectrum in the crystalline state
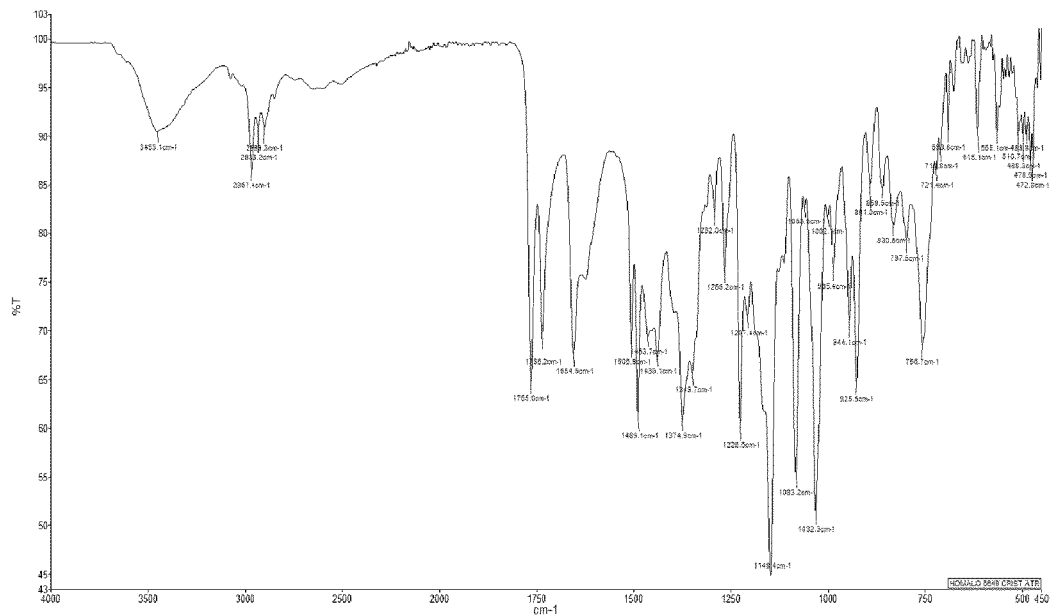
ii) IR (ATR) spectrum in the amorphous state (film)
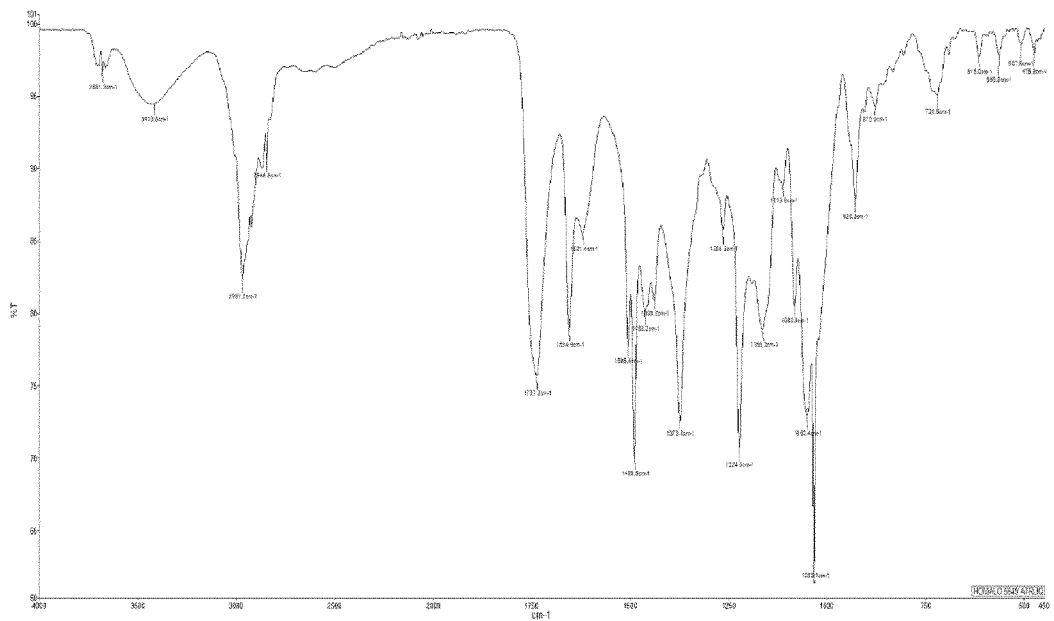

FIGURE 1.13: IR of homoharringtonine dihydrogen citrate in the solid state.
i) IR (ATR) spectrum in the crystalline state
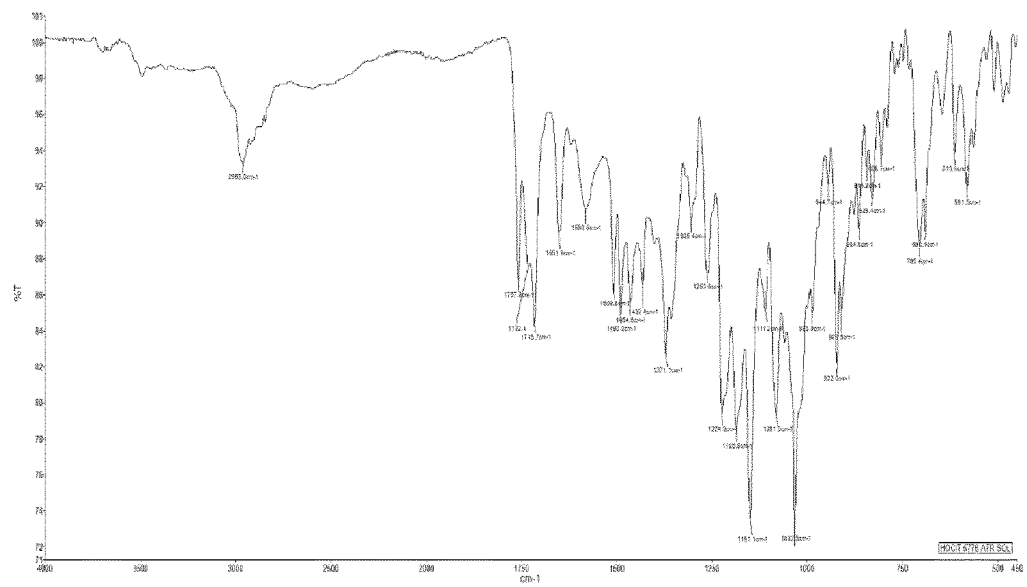
ii) IR (ATR) spectrum in the amorphous state (film)
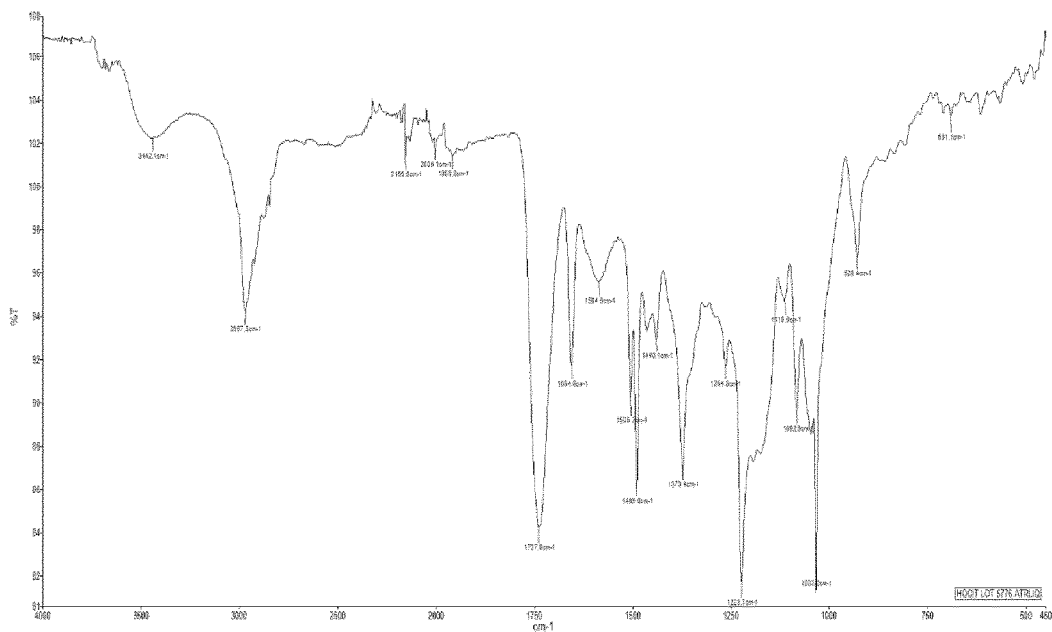

FIGURE 1.14: IR of homoharringtonine salicylate in the solid state.
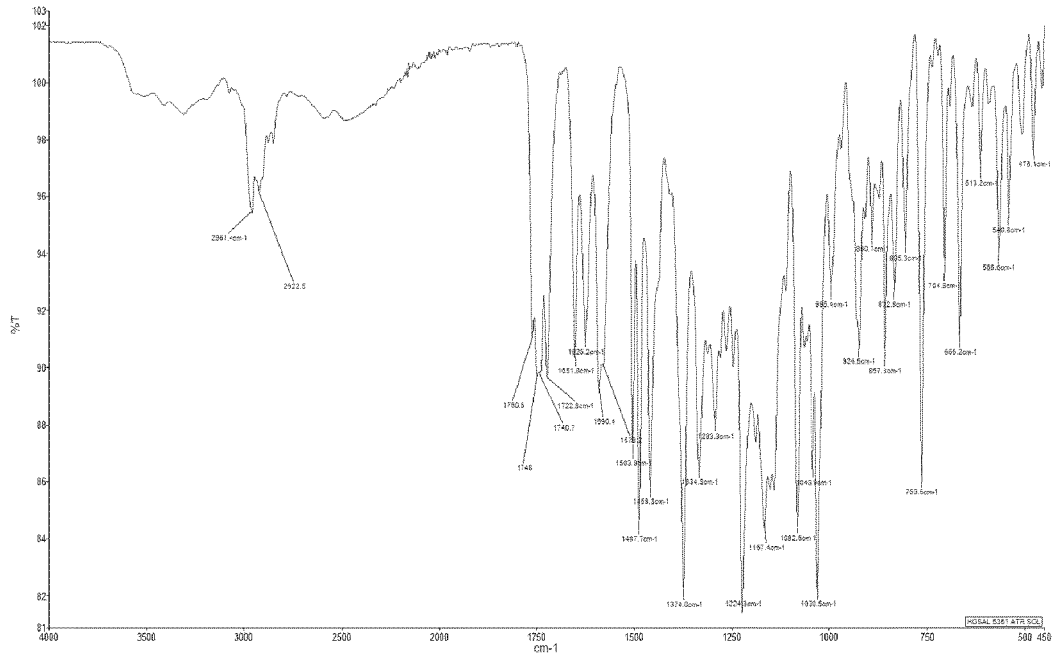
i)     IR (ATR) spectrum in the crystalline state
ii)     IR (ATR) spectrum in the amorphous state (film)
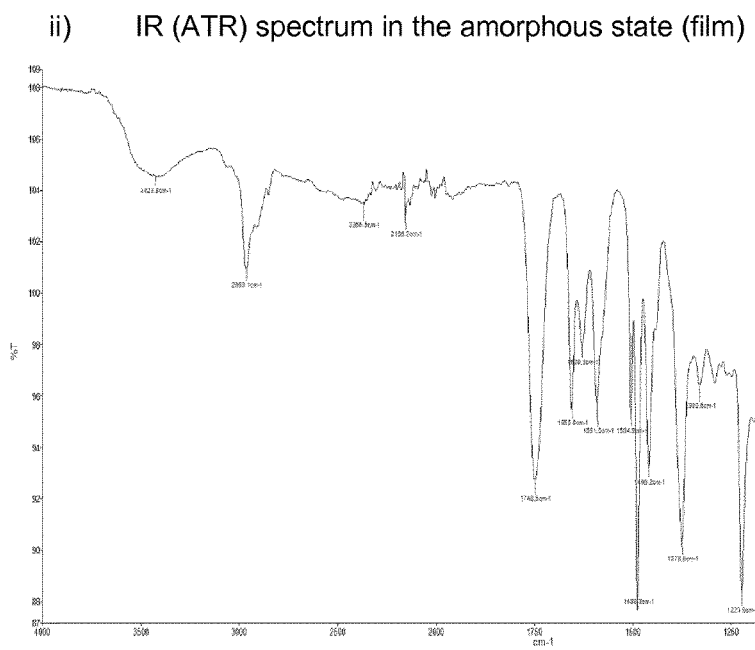

Figure 2.2.1: Single crystal X-ray diffraction of homoharringtonine base, form A (ORTEP-3 software)
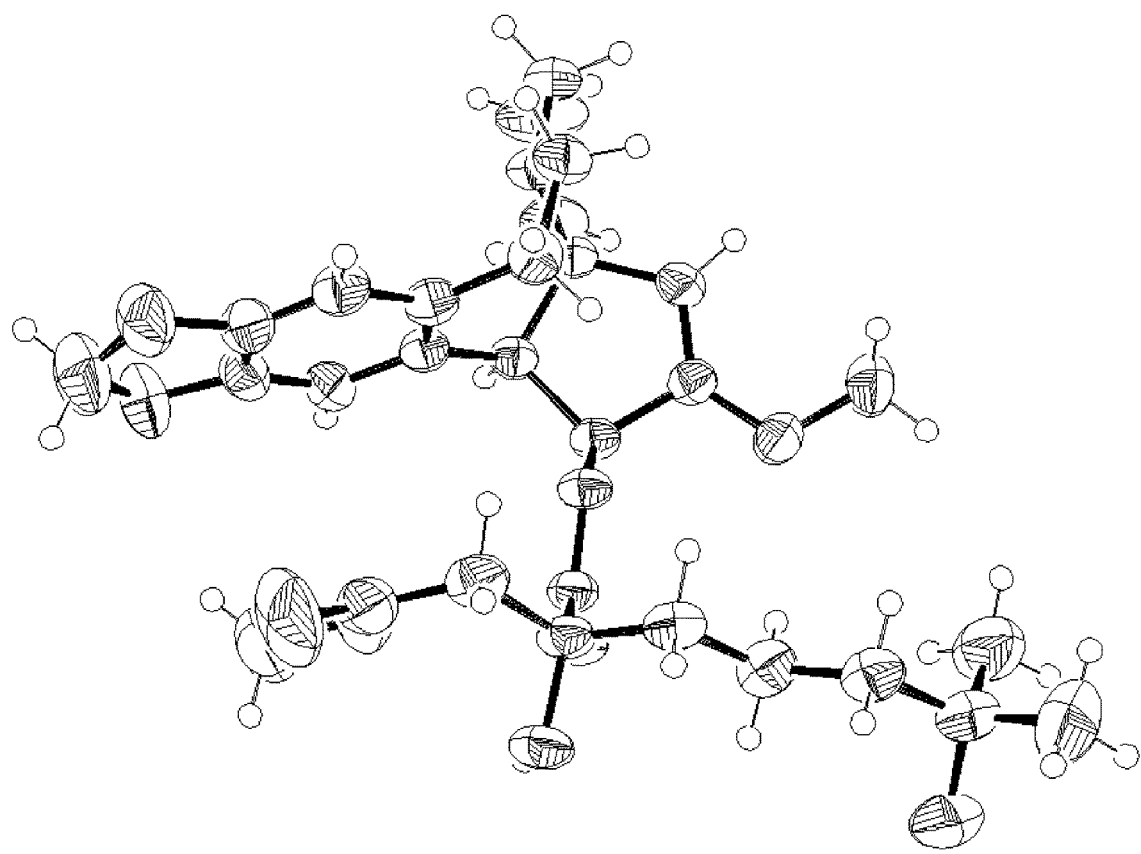

Figure 2.2.2: Single crystal X-ray diffraction of homoharringtonine base, form B (ORTEP-3 software)
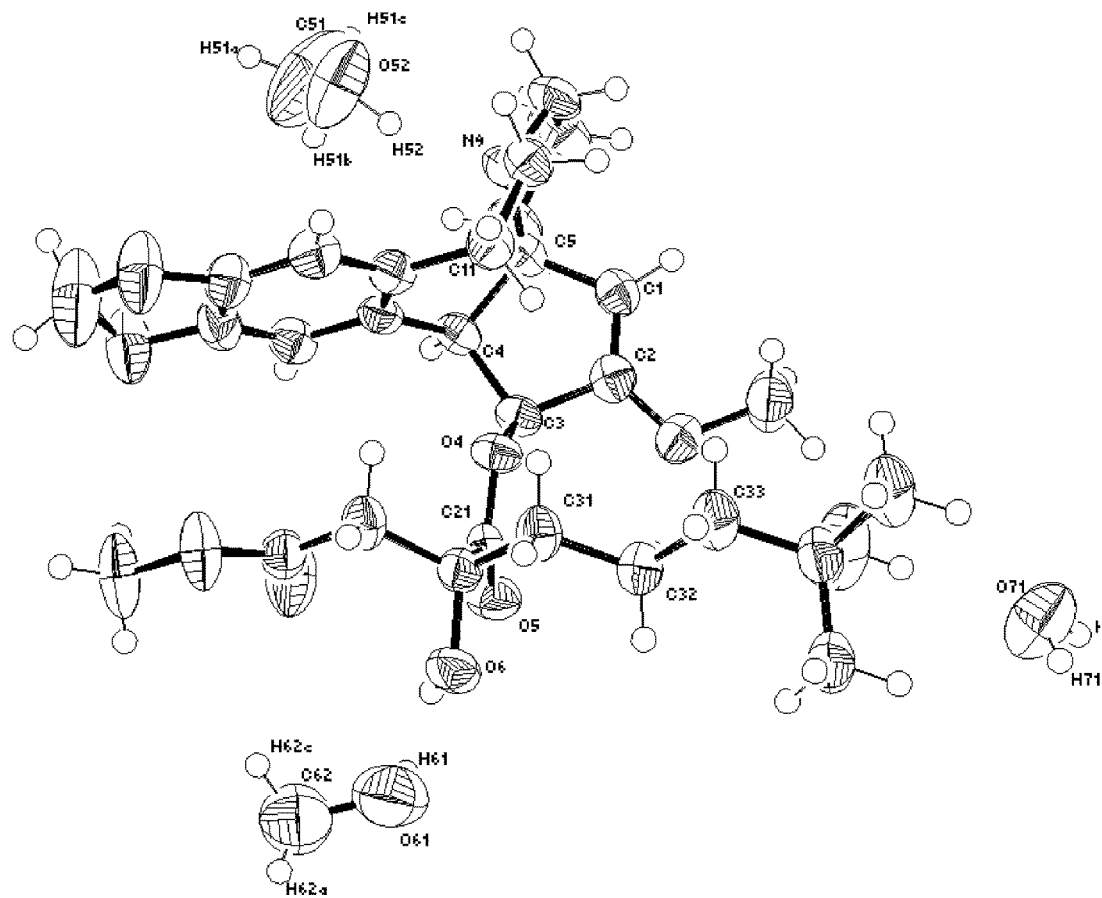
Comments
Shortest distance between H52 of MeOH and Hn9 is 1.835Å (calculated by ORTEP-3). There is two methanol molecule and one mol. of water of crystallization per asymmetric unit.

Figure 2.2.3: Single crystal X-ray diffraction of homoharringtonine base, form B; corresponding packing with unit cell content (PLUTO drawing, ORTEP-3 software)
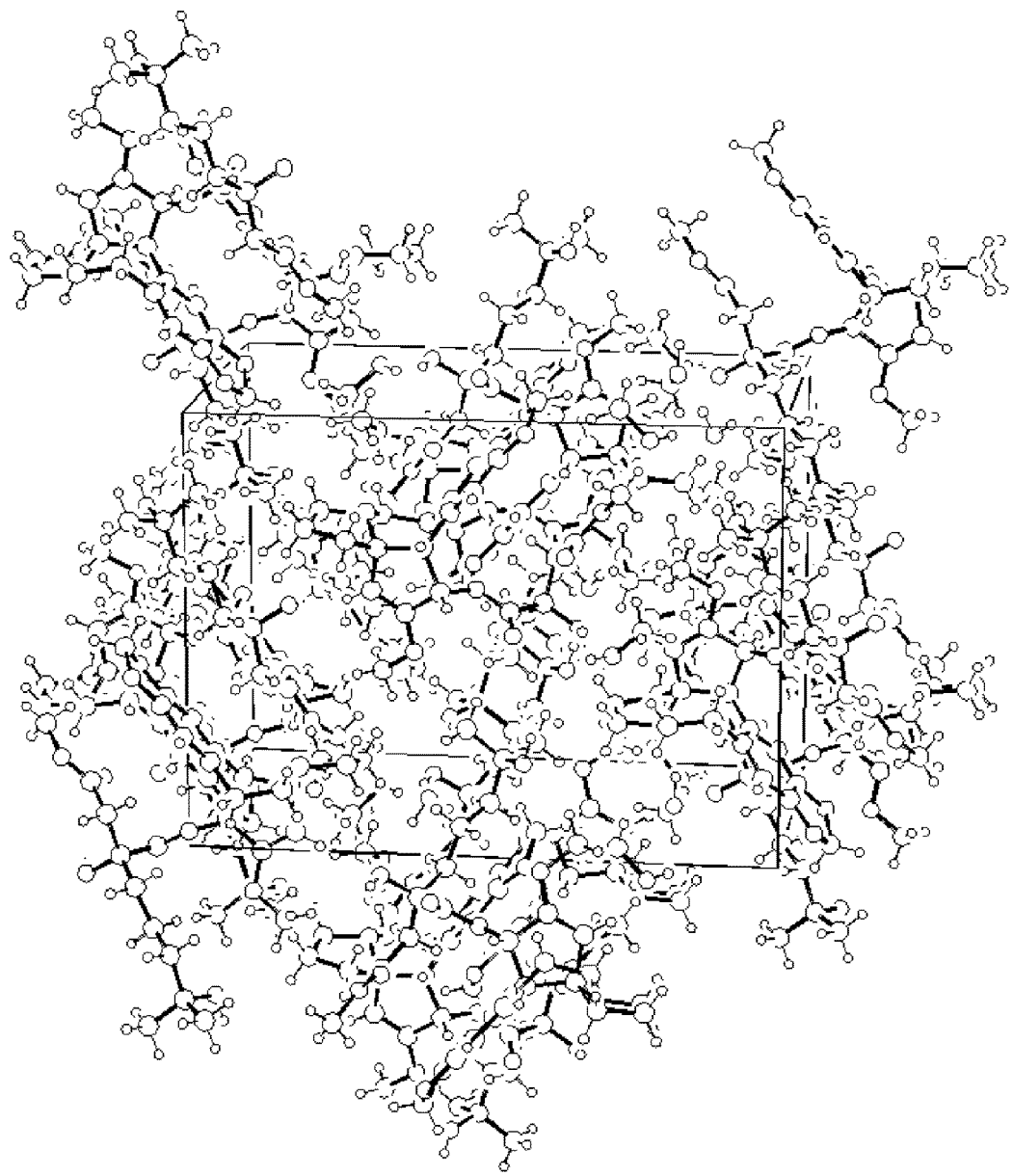

Figure 2.3.1: Single crystal X-ray diffraction of homoharringtonine hydrogen (2S)-(-)-malate (ORTEP-3 software)
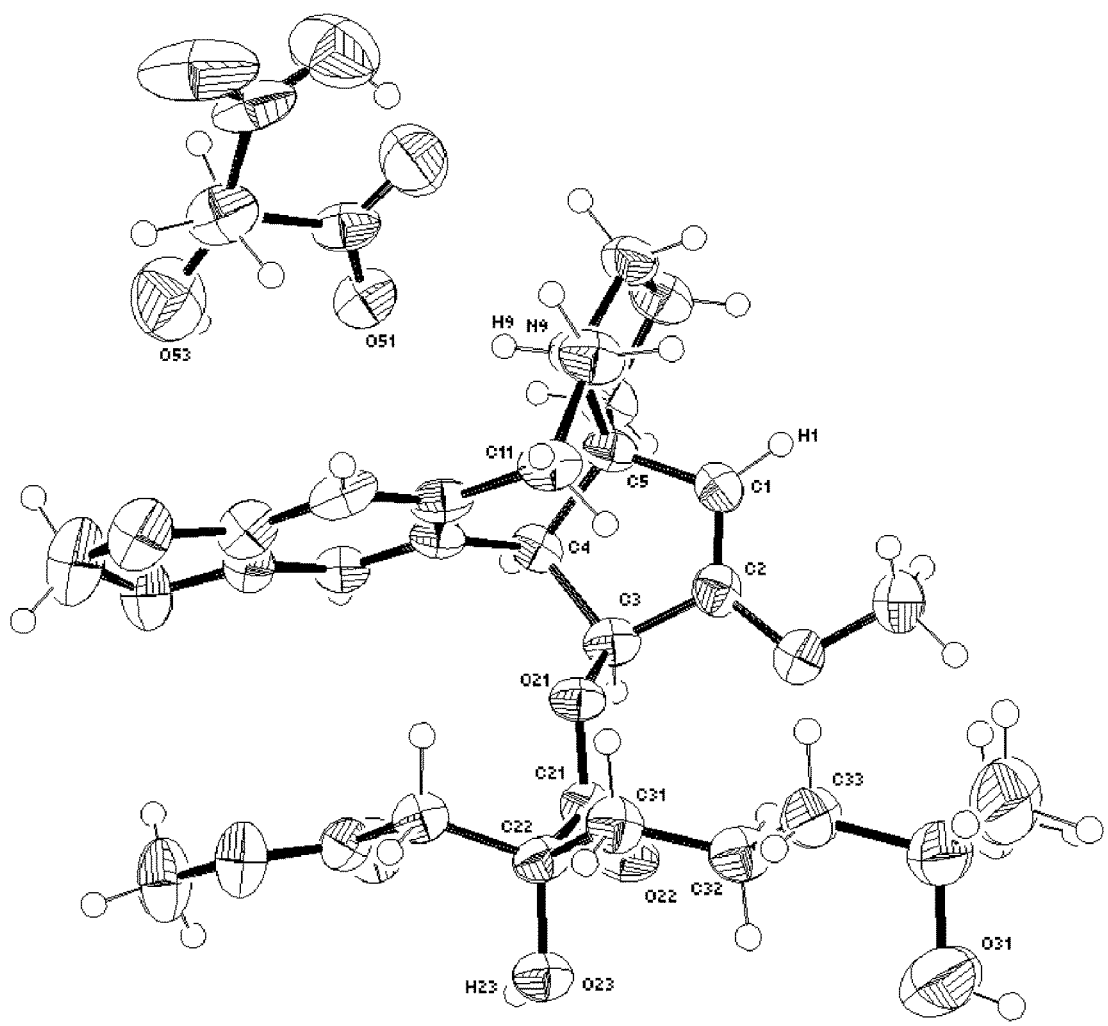
COMMENTS
Shortest distance between anion and cation O51-Hn9 is 1.906Å (calculated by ORTEP-3). O52 is the negative charge oxygen atom of hydrogen (2S)-malate anion and Hn9 is the proton borne by the alkaloid nitrogen. H23-O22 is 2.524 Å. There is no solvent. of crystallization.

Figure 2.3.2: Single crystal X-ray diffraction of homoharringtonine hydrogen (2S)-(-)-malate, corresponding packing with unit cell content (PLUTO, ORTEP-3 software)
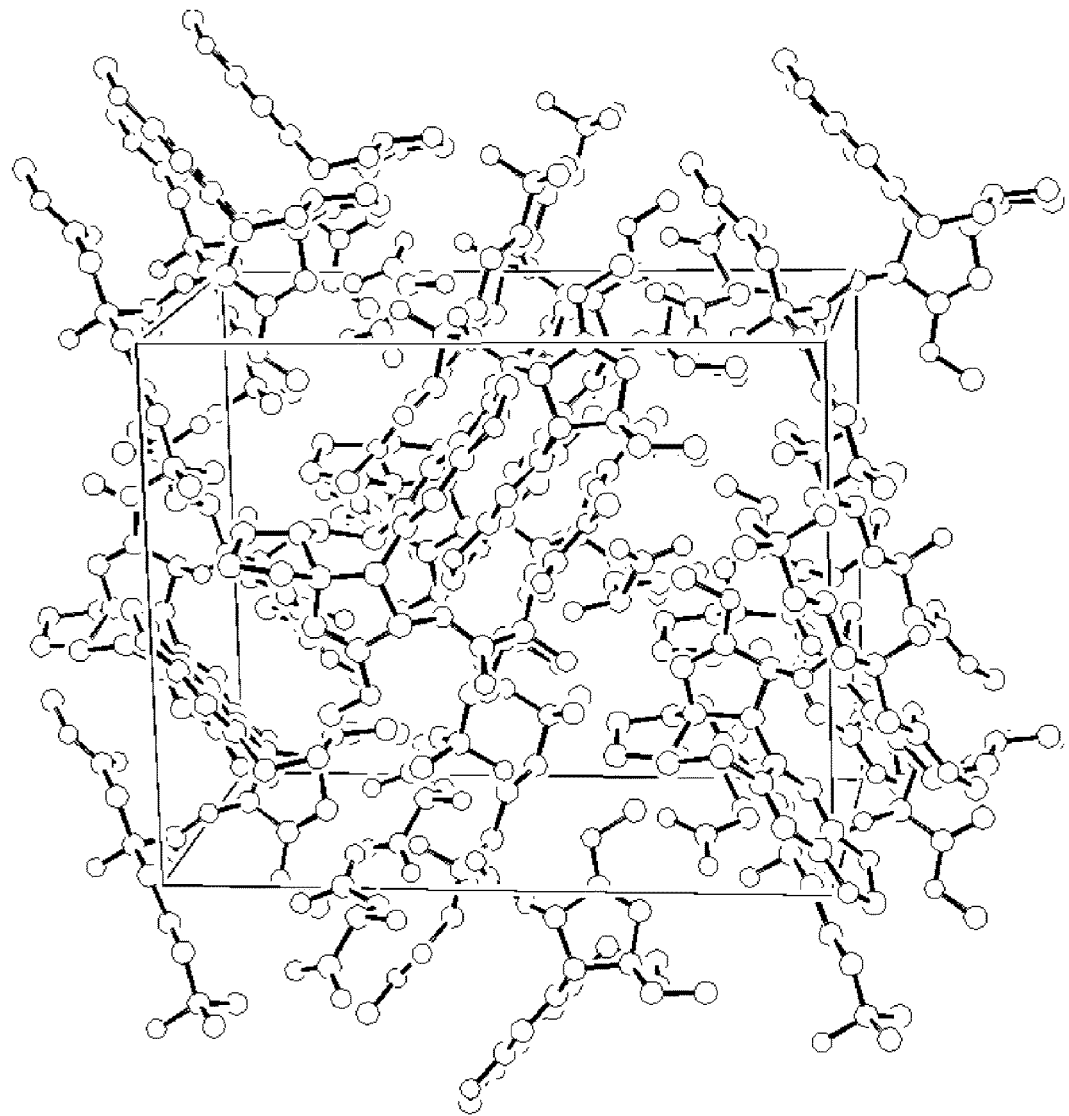

Figure 2.3.3: X-ray powder diffraction (XRPD) of homoharringtonine hydrogen (2S)-(-)-malate
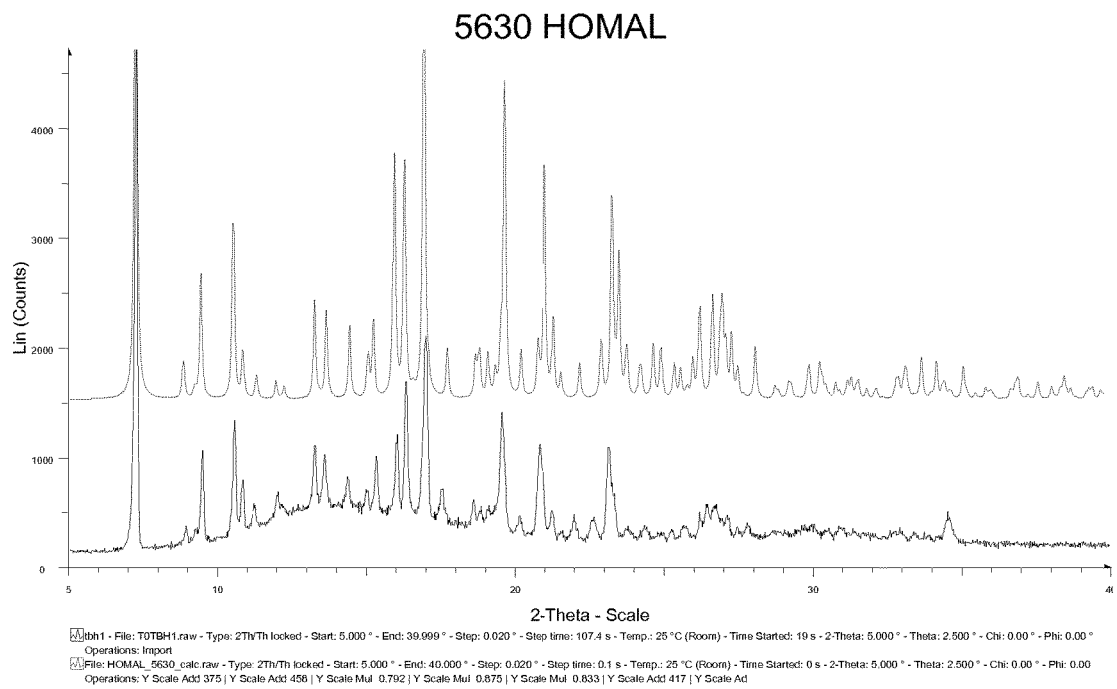

Figure 2.4.1: Single crystal X-ray diffraction of homoharringtonine hydrogen (2R)-(+)-malate (created by ORTEP-3 software)
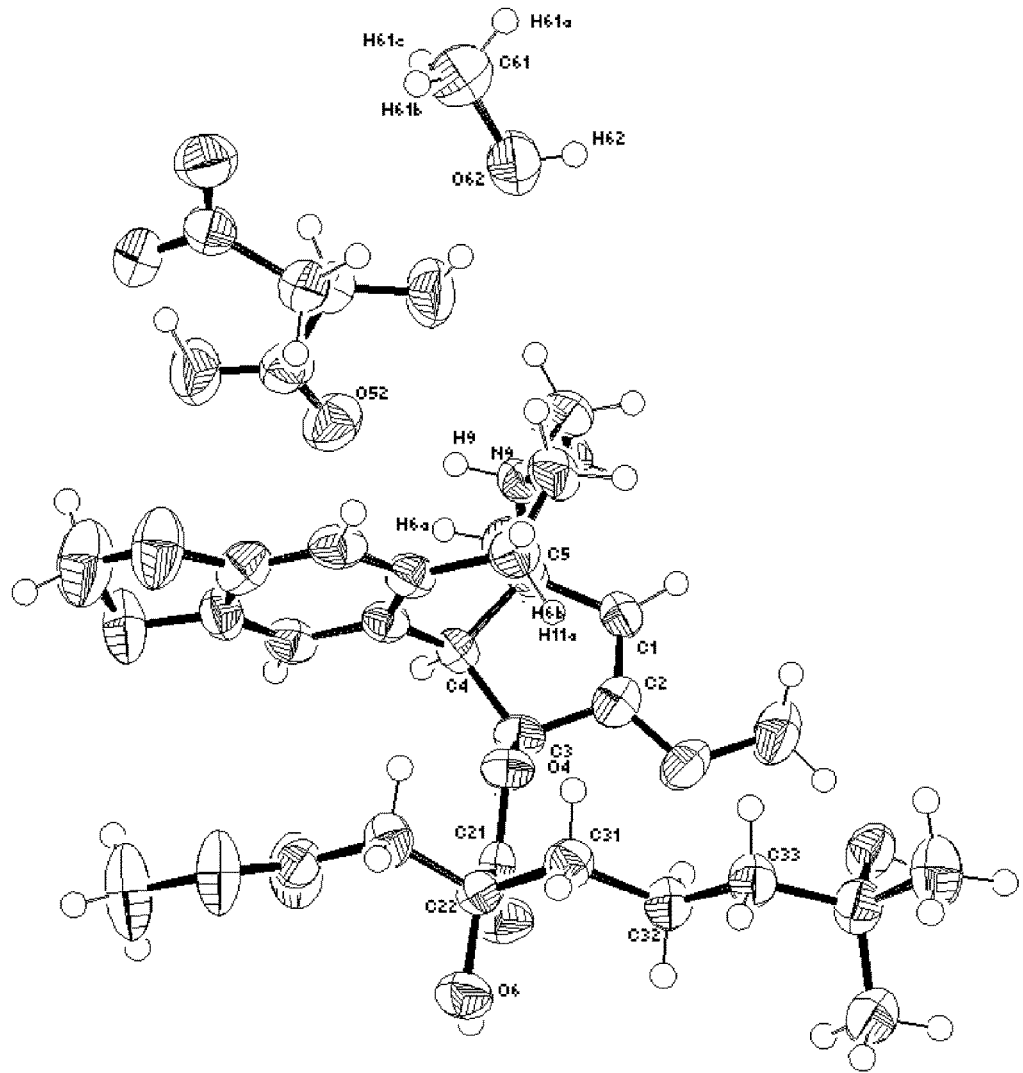
Comments
Shortest distance between anion and cation O52-Hn9 is 1.959Å (calculated by ORTEP-3). Hn9 is the proton borne by the alkaloid nitrogen. There is one methanol mol. of crystallization per asymmetric unit (H61a,H61b,H61c-C61-O62-Ho62).

Figure 2.4.2: Single crystal X-ray diffraction of homoharringtonine hydrogen (2R)-(+)-malate; corresponding packing with unit cell content (PLUTO, ORTEP-3 software)
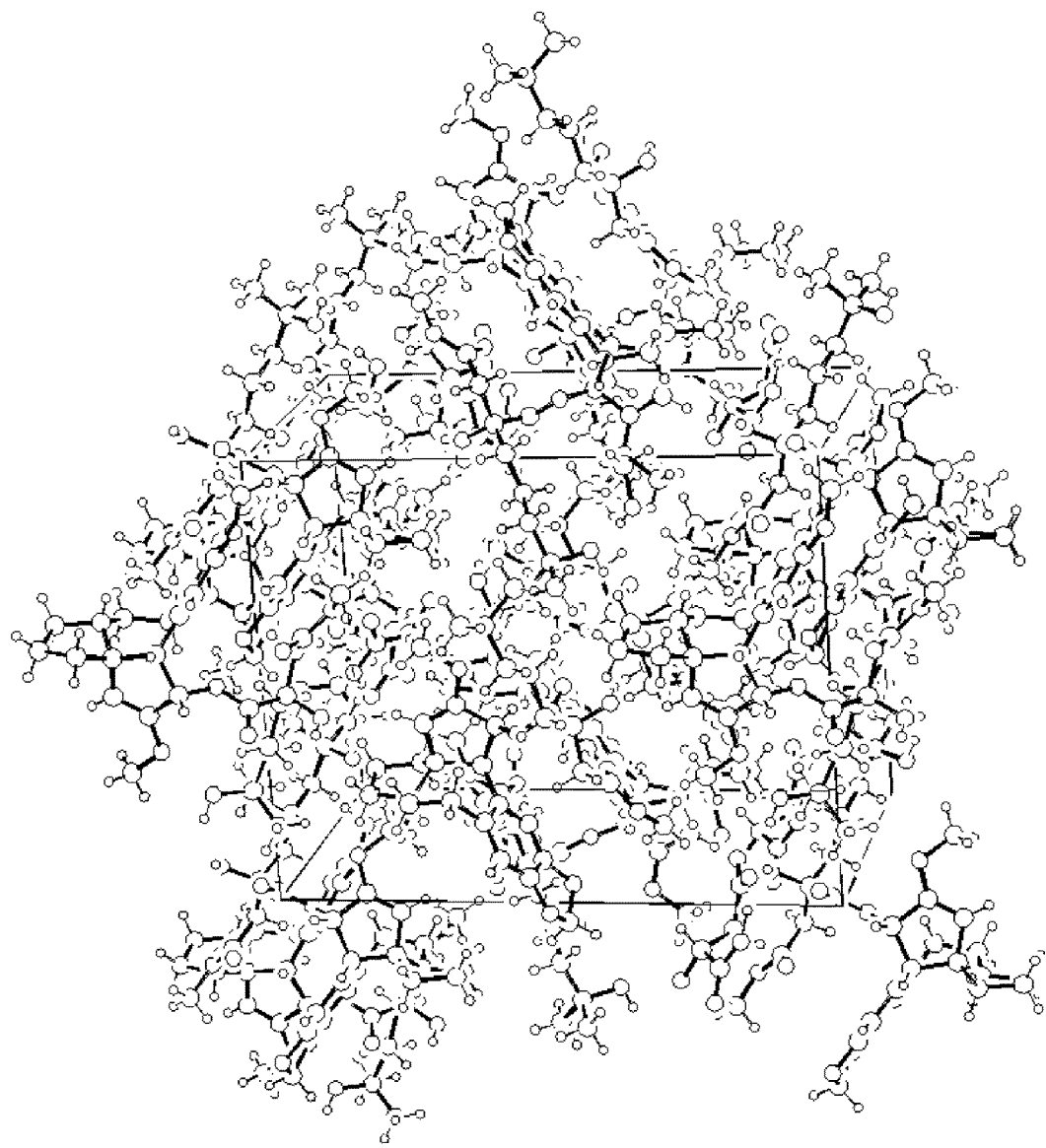

Figure 2.4.3: X-ray powder diffraction (XRPD) of homoharringtonine hydrogen (2R)-(+)-malate
1. 5646 HOMAL
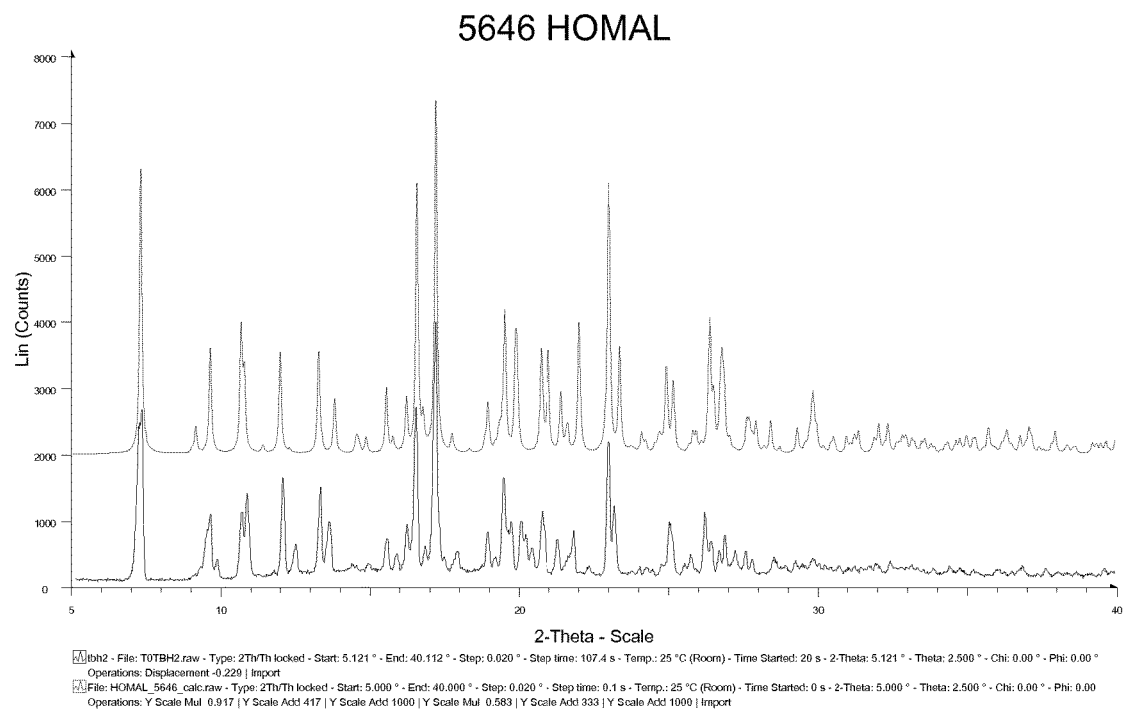

Figure 2.5.1: Single crystal X-ray diffraction of homoharringtonine hydrogen (2S,3S)-(-)-tartrate (calculated by ORTEP-3 software)
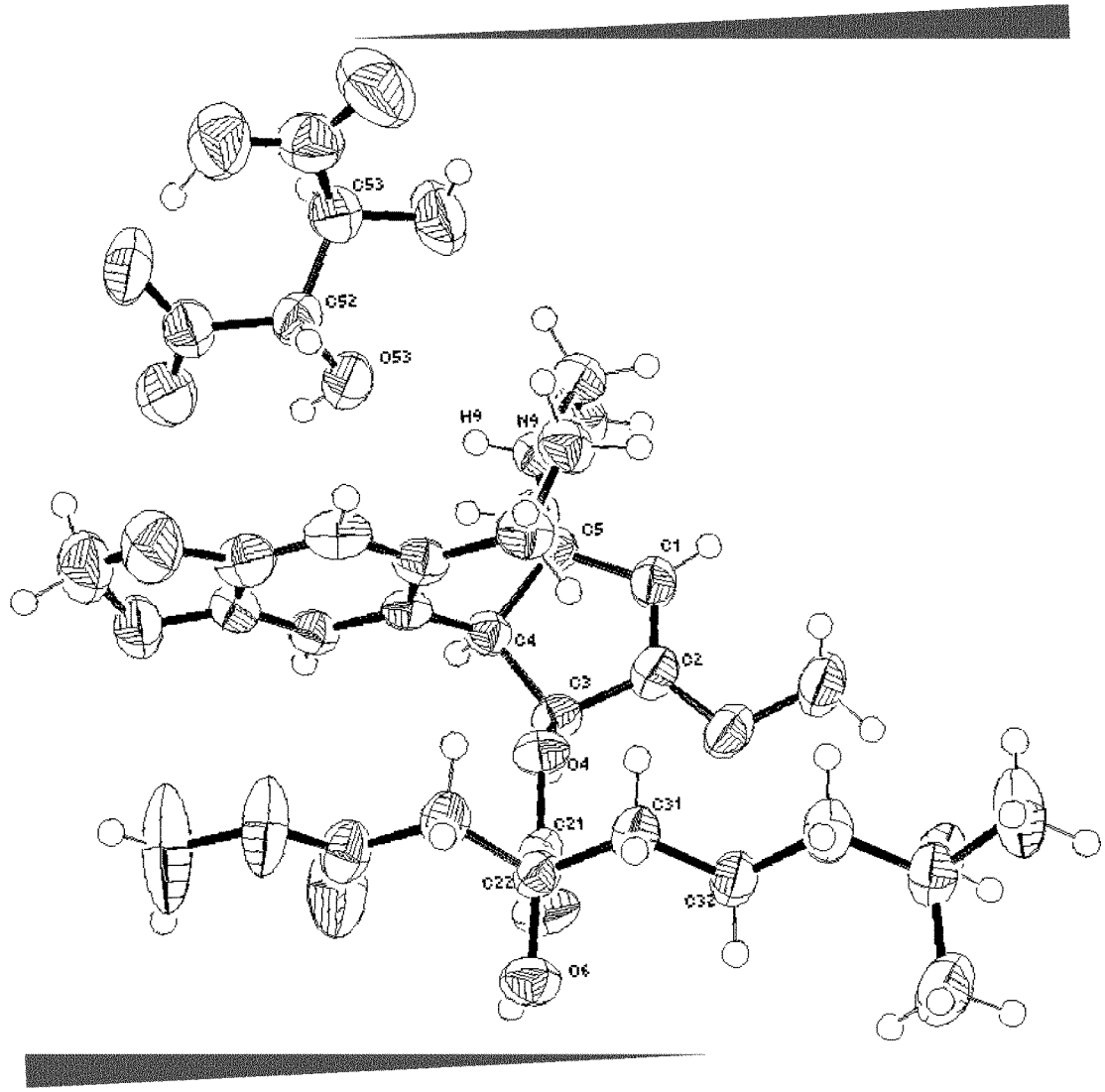
Comments
Shortest distance between anion and cation O53-Hn9 is 1.988Å (calculated by ORTEP-3). Hn9 is the proton borne by the alkaloid nitrogen. There is no solvent of crystallization Figure 2.5.2: Single crystal X-ray diffraction of homoharringtonine hydrogen (2S,3S)-(+)-tartrate; corresponding packing (with unit cell content (PLUTO, ORTEP-3 software)
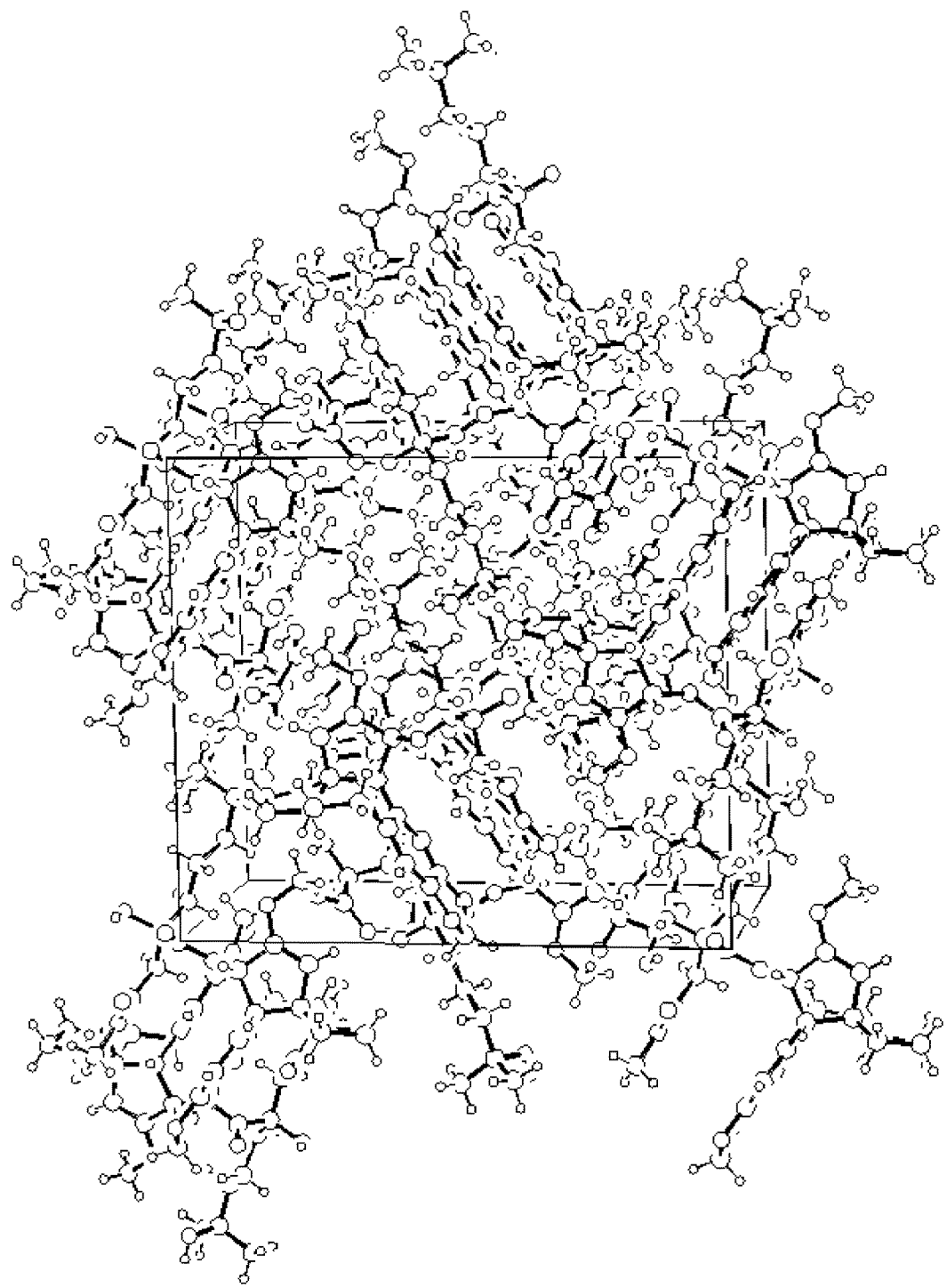

Figure 2.5.3: X-ray powder diffraction (XRPD) of homoharringtonine hydrogen (2S,3S)-(-)-tartrate
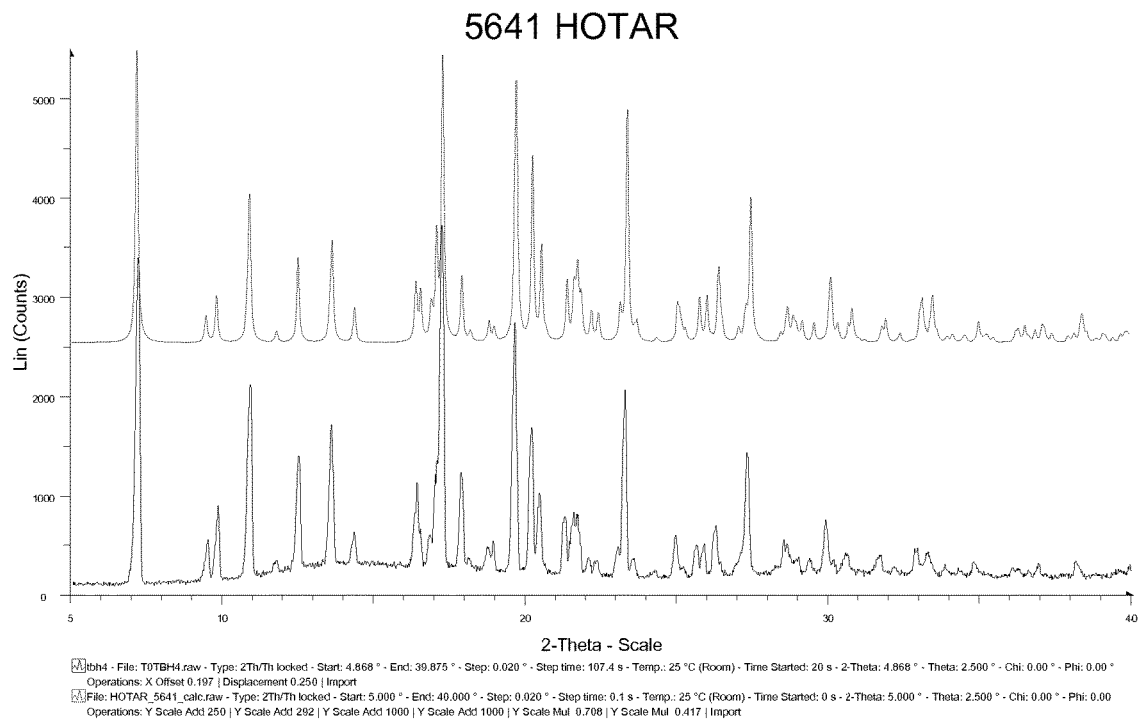

Figure 2.6.1: Single crystal X-ray diffraction of homoharringtonine hydrogen (2R,3R)-(+)-tartrate (ORTEP-3 software)
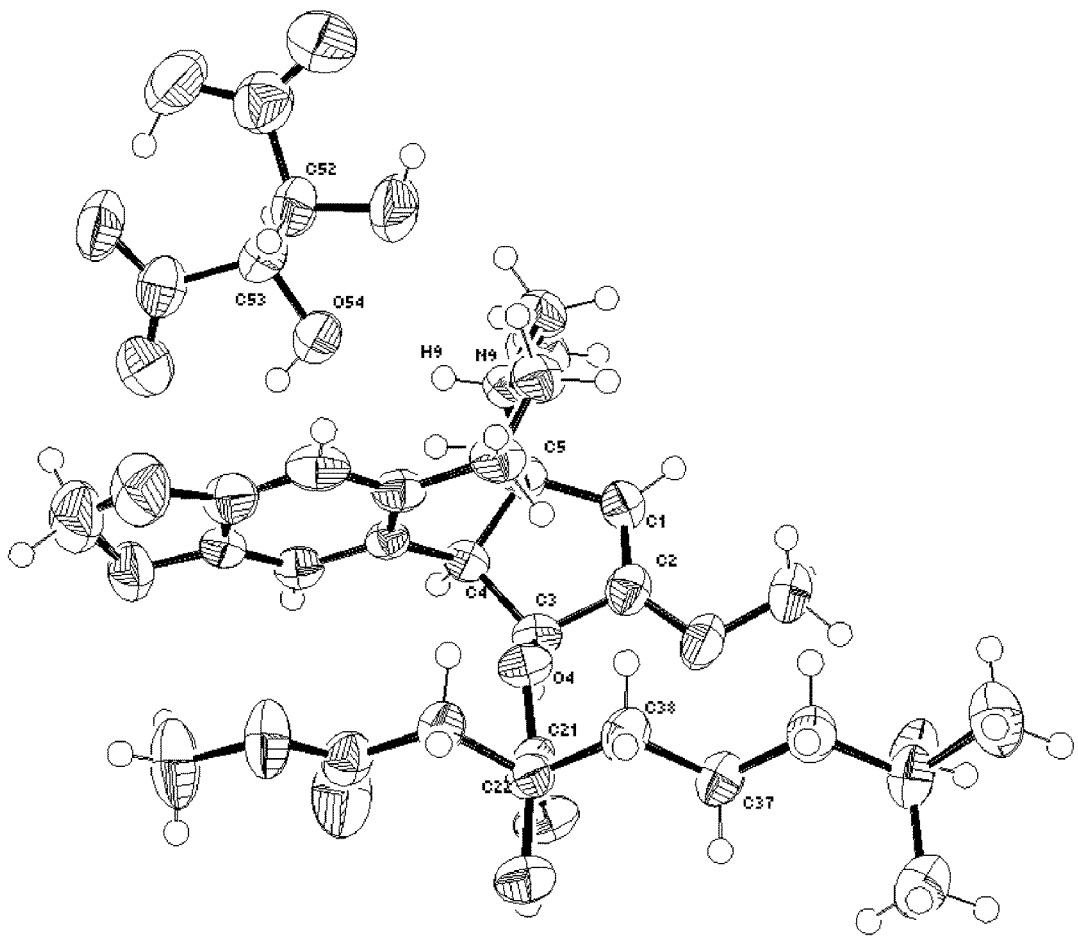
Comments
Shortest distance between anion and cation O54-Hn9 is 1.984 Å (calculated by ORTEP-3). Hn9 is the proton borne by the alkaloid nitrogen. There is solvent of crystallization.

Figure 2.6.2: Single crystal X-ray diffraction of homoharringtonine hydrogen (2R,3R)-(+)-tartrate; corresponding packing with unit cell content (PLUTO, ORTEP-3 software)
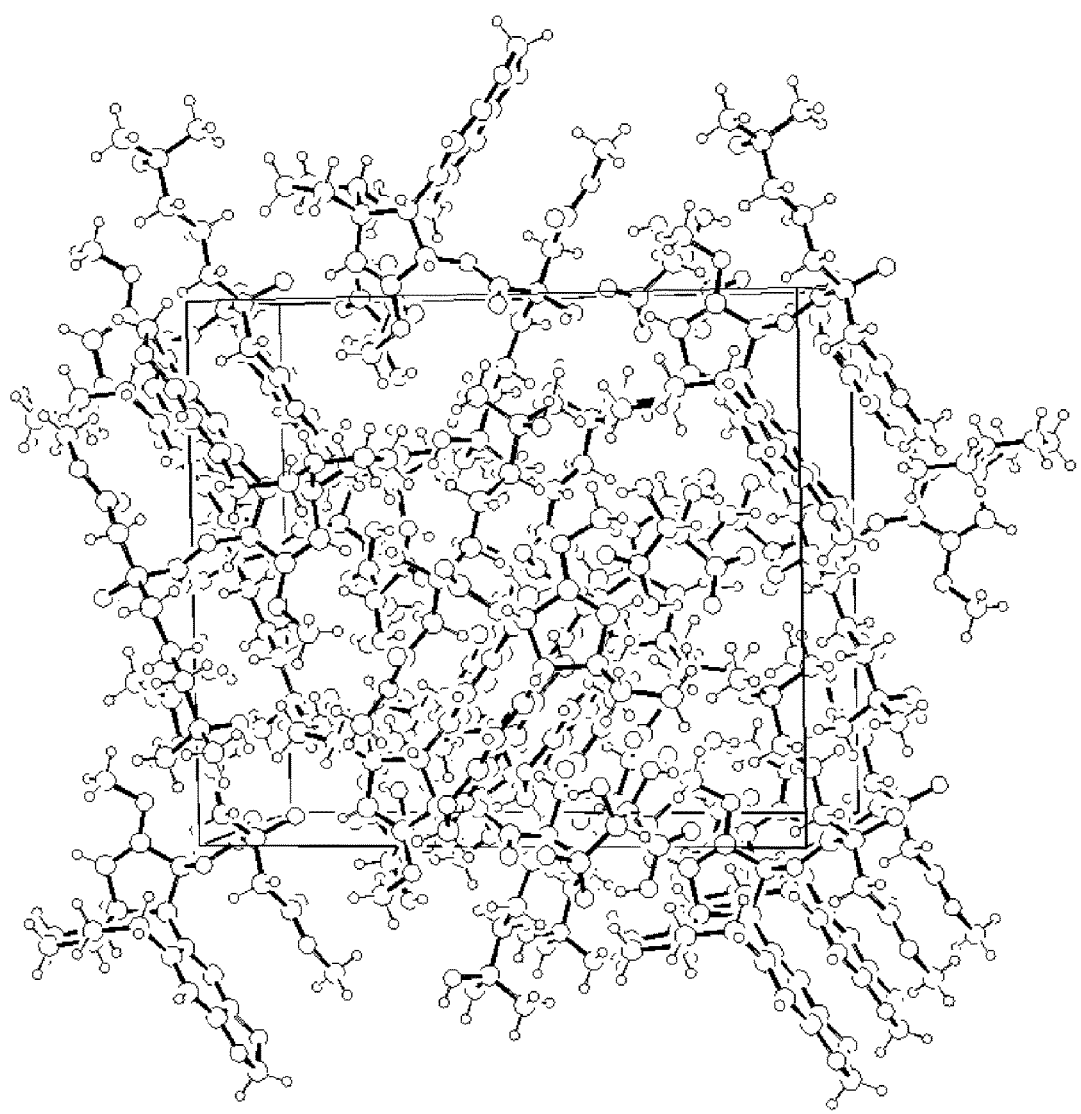

Figure 2.6.3: X-ray powder diffraction (XRPD) of homoharringtonine hydrogen (2R,3R)-(+)-tartrate.
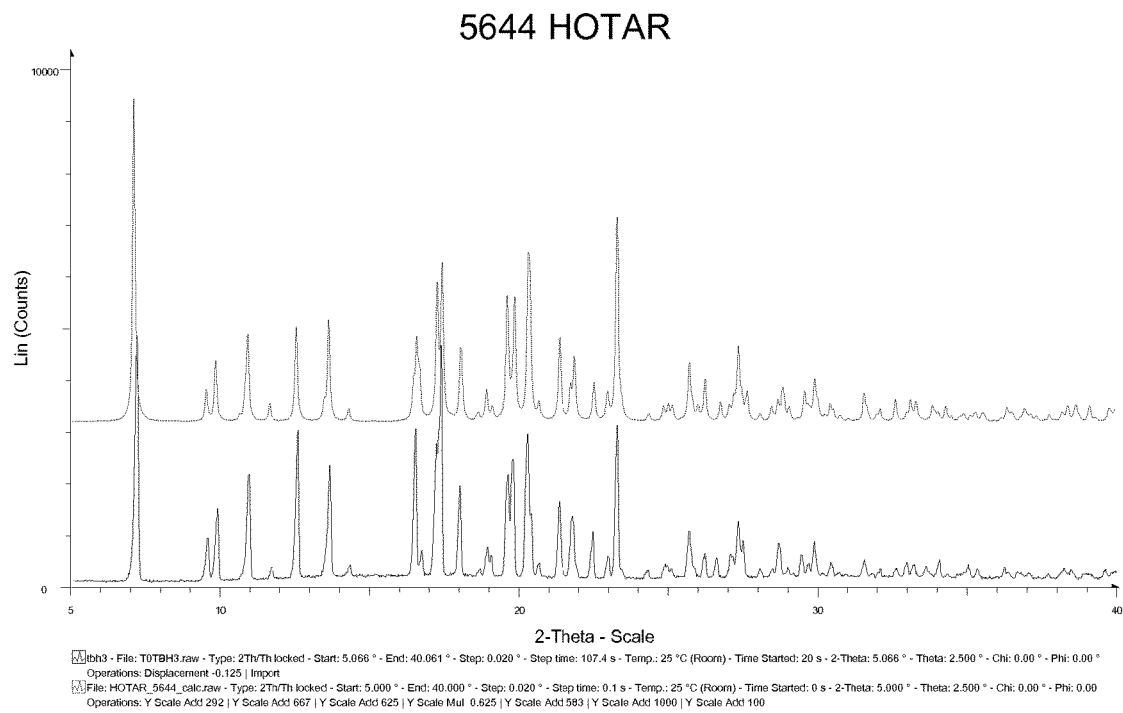

Figure 2.7.1: X-ray powder diffraction (XRPD) of homoharringtonine hydrogen (2'''S)-citramalate.
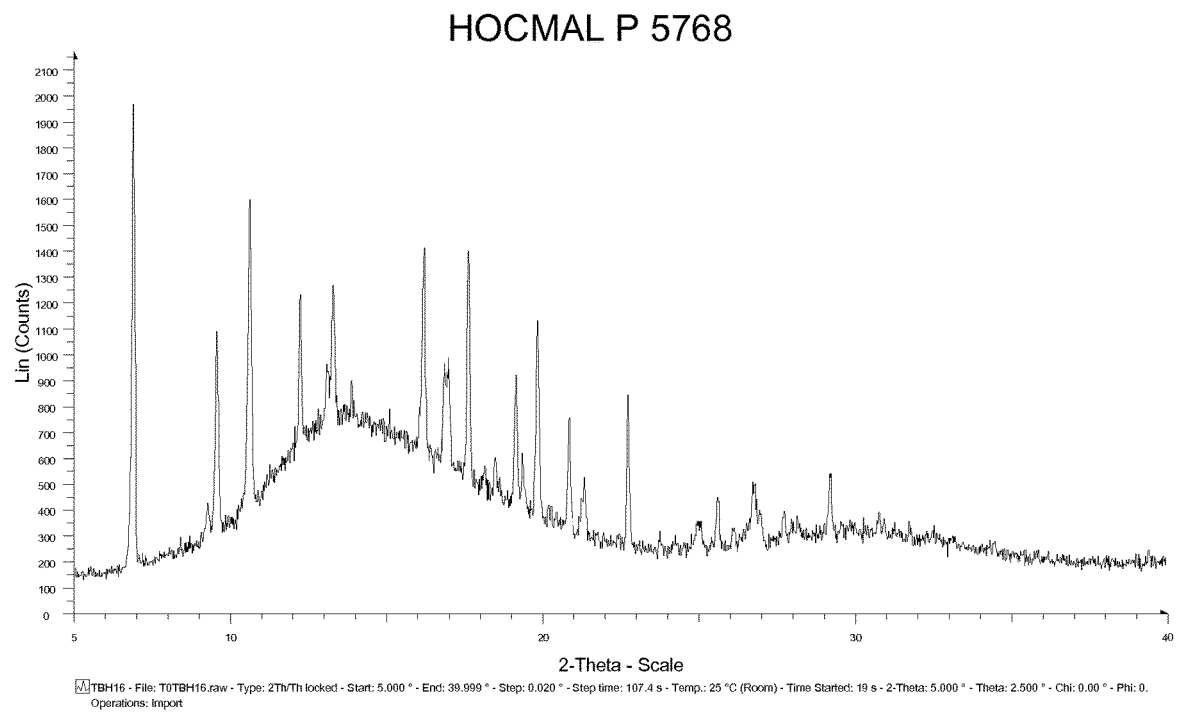

Figure 2.8.1: Single crystal X-ray diffraction of homoharringtonine hydrogen (2R)-(-)-citramalate (ORTEP-3 software)
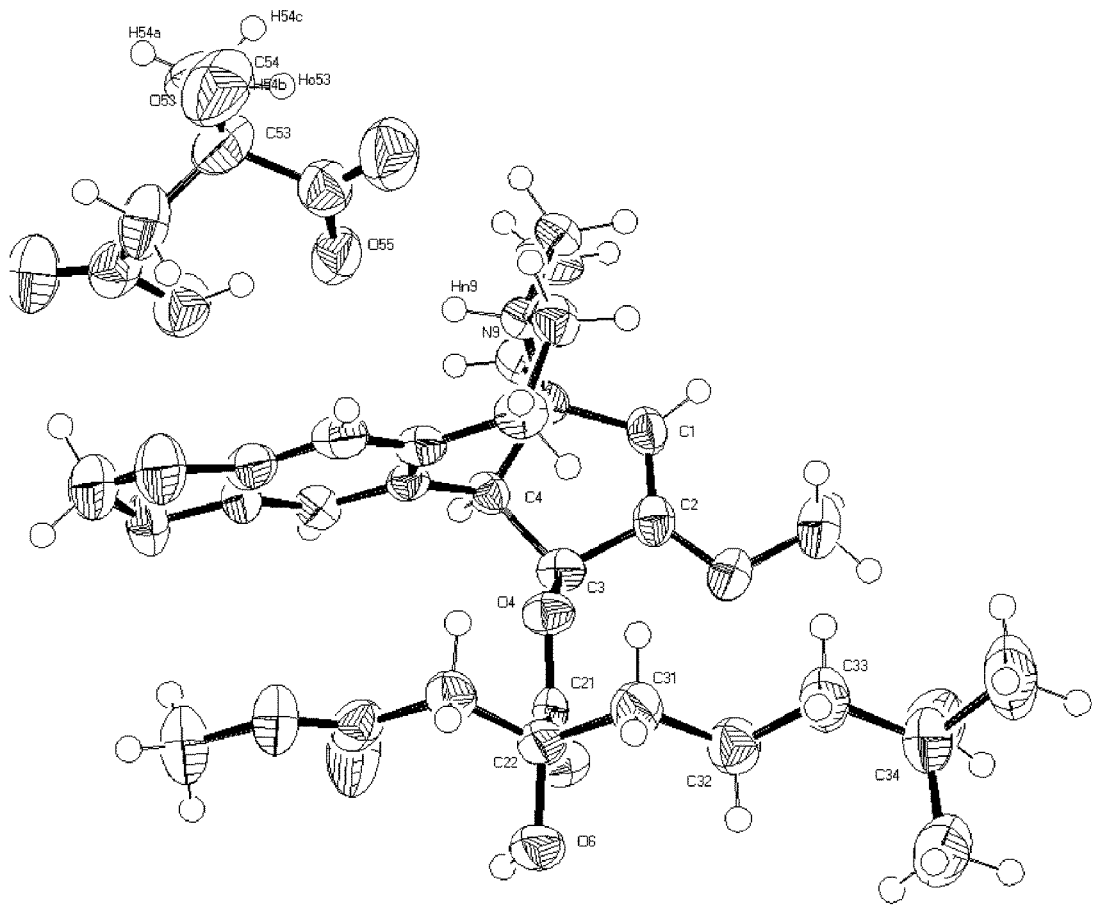
COMMENTS
Shortest distance between anion and cation O52-Hn9 is 1.836Å (calculated by ORTEP-3). O52 is the negative charge oxygen atom of hydrogen citramalate anion (= 2-methylmalate) and Hn9 is the proton borne by the alkaloid nitrogen. There is no solvent. of crystallization.

Figure 2.8.2: Single crystal X-ray diffraction of homoharringtonine hydrogen (2R)-(-)-citramalate; corresponding packing with unit cell content (PLUTO, ORTEP-3 software)
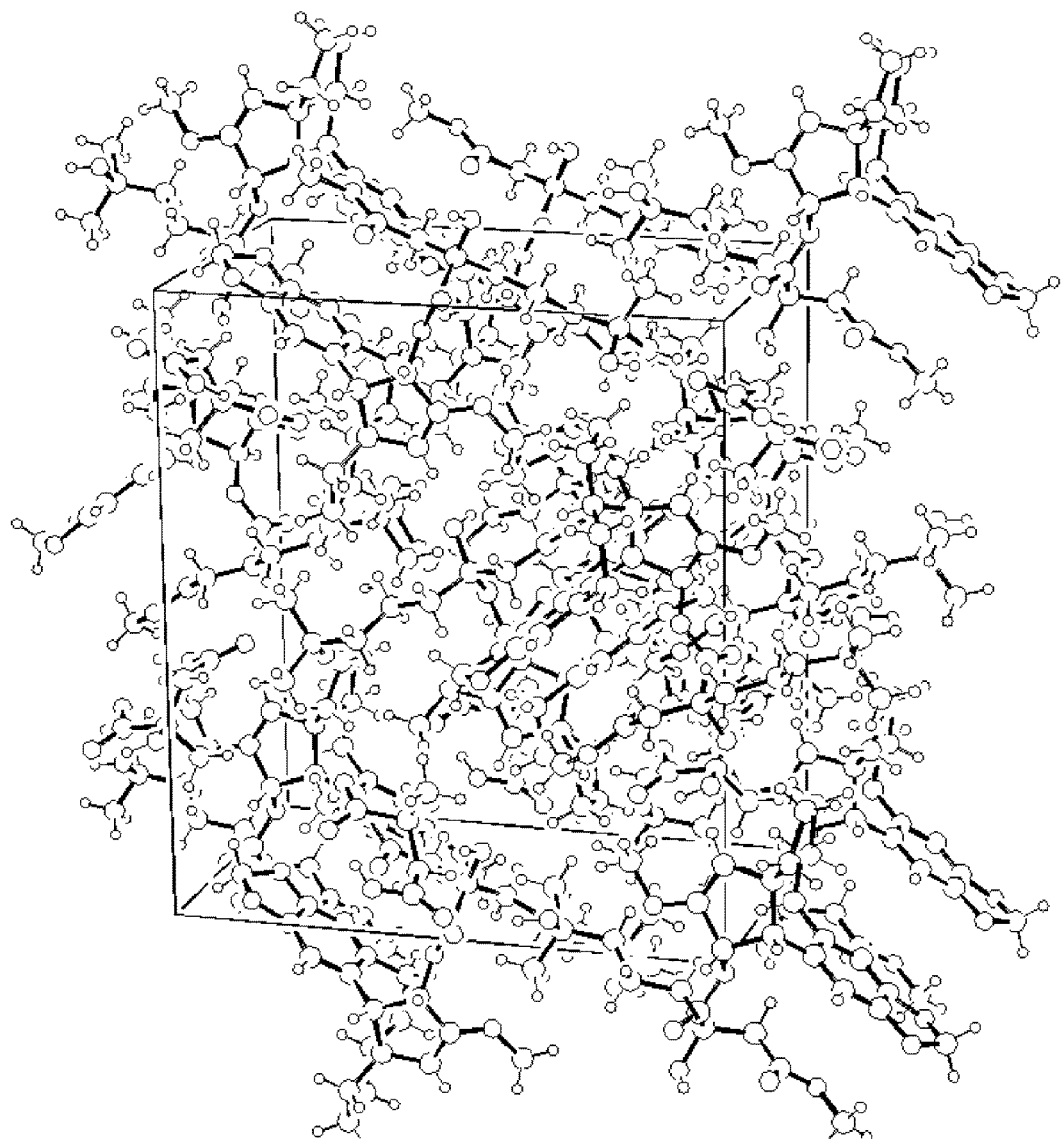

Figure 2.8.3: X-ray powder diffraction (XRPD) of homoharringtonine hydrogen (2R)-(-)-citramalate
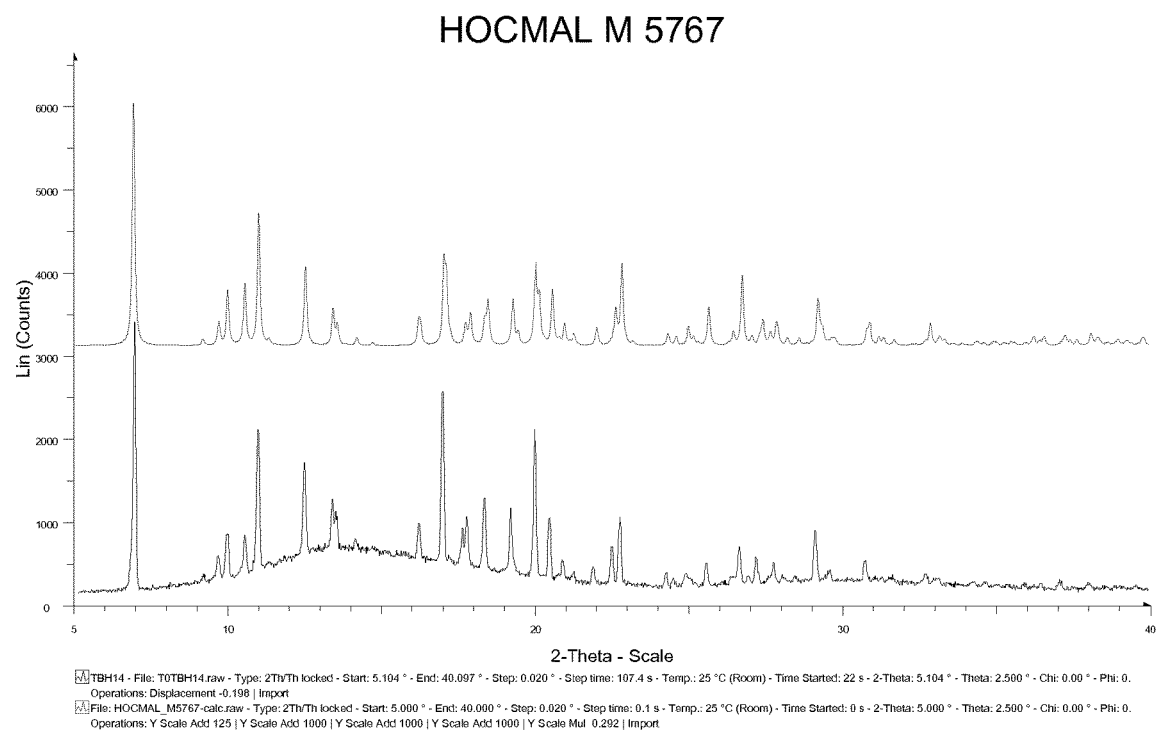

Figure 2.9.1: Single crystal X-ray diffraction of homoharringtonine hydrogen itaconate (ORTEP-3 software)
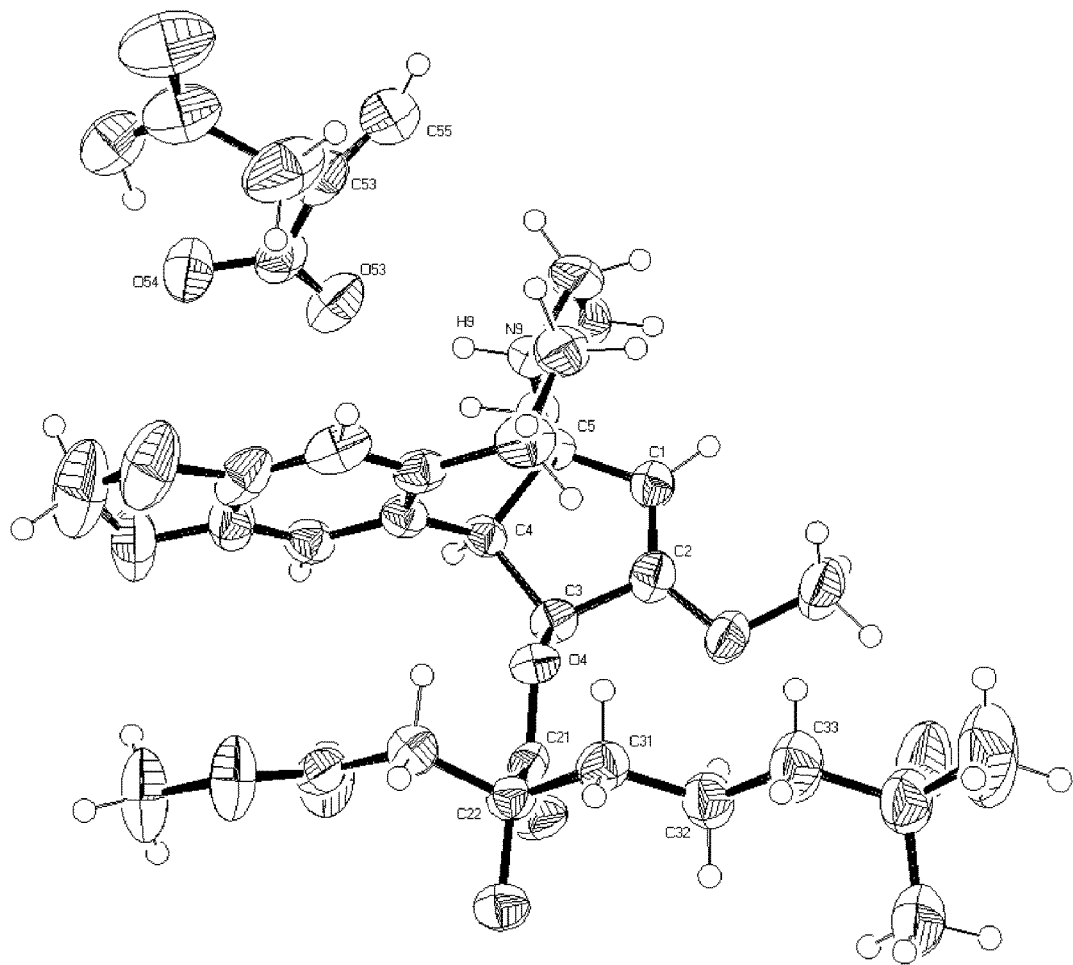
Comments
Shortest distance between anion and cation O53-Hn9 is 1.911Å (calculated by ORTEP-3). O51 is the negative charge oxygen atom of dihydrogen citrate anion and Hn9 is the proton borne by the alkaloid nitrogen. There is no solvent of crystallization.

Figure 2.9.2: Single crystal X-ray diffraction of homoharringtonine hydrogen itaconate; corresponding packing with unit cell content (PLUTO, ORTEP-3 software)
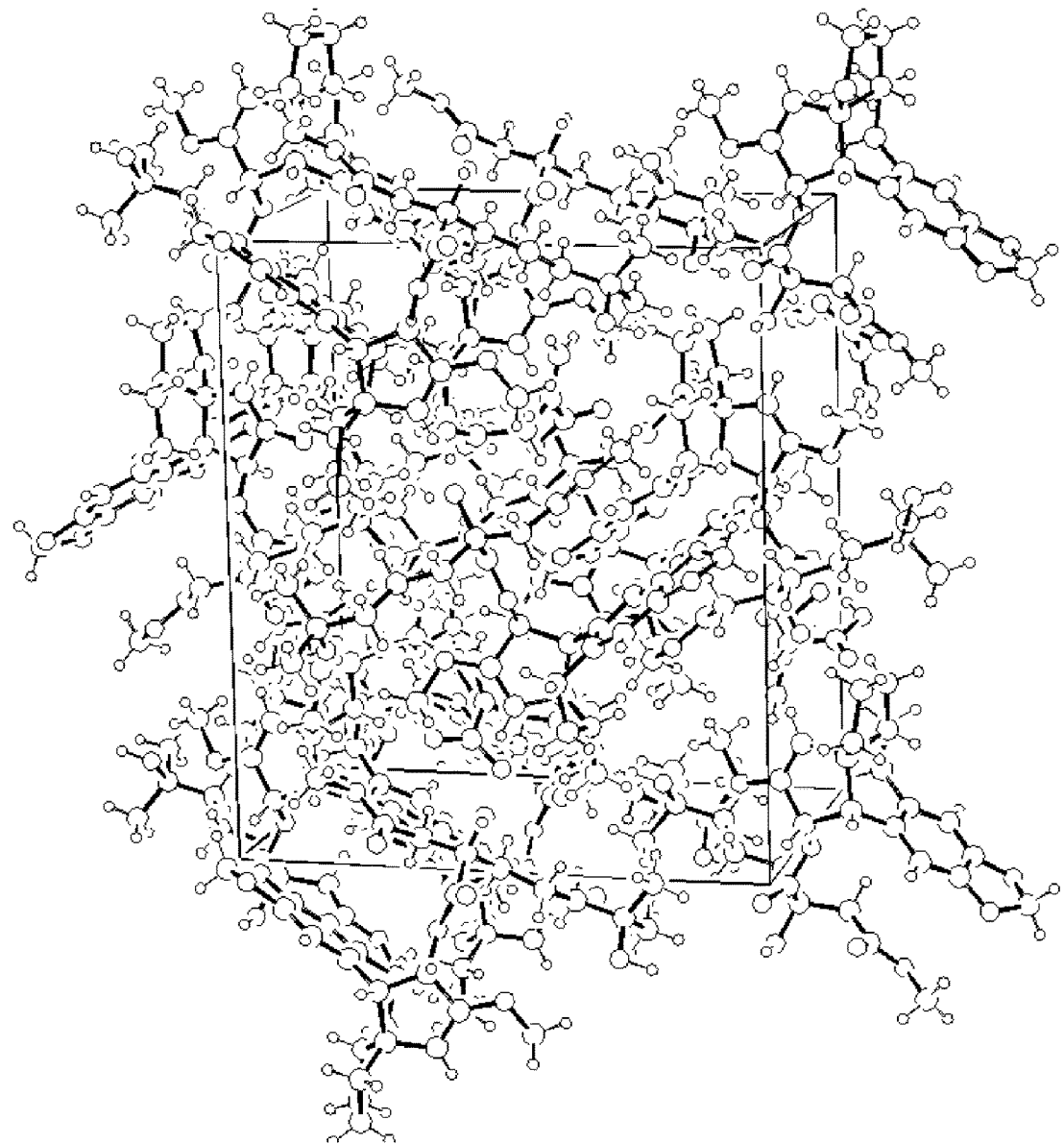

Figure 2.10.1: X-ray powder diffraction (XRPD) of homoharringtonine hydrogen fumarate
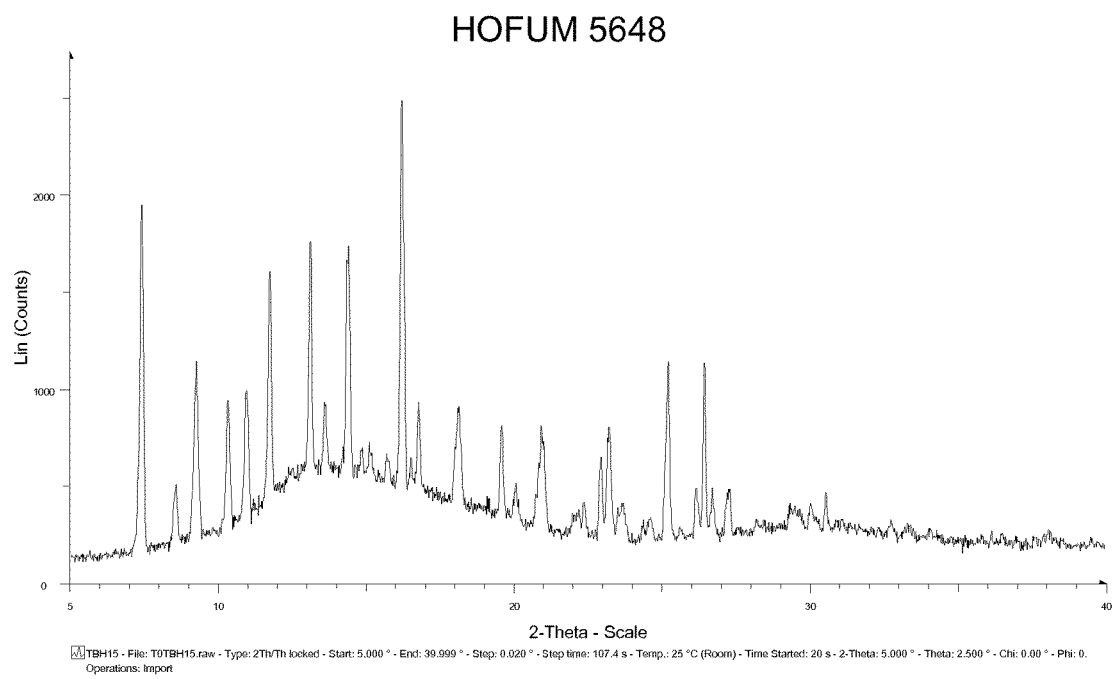

Figure 2.11.1: Single crystal X-ray diffraction of homoharringtonine dihydrogen citrate (ORTEP-3 software)

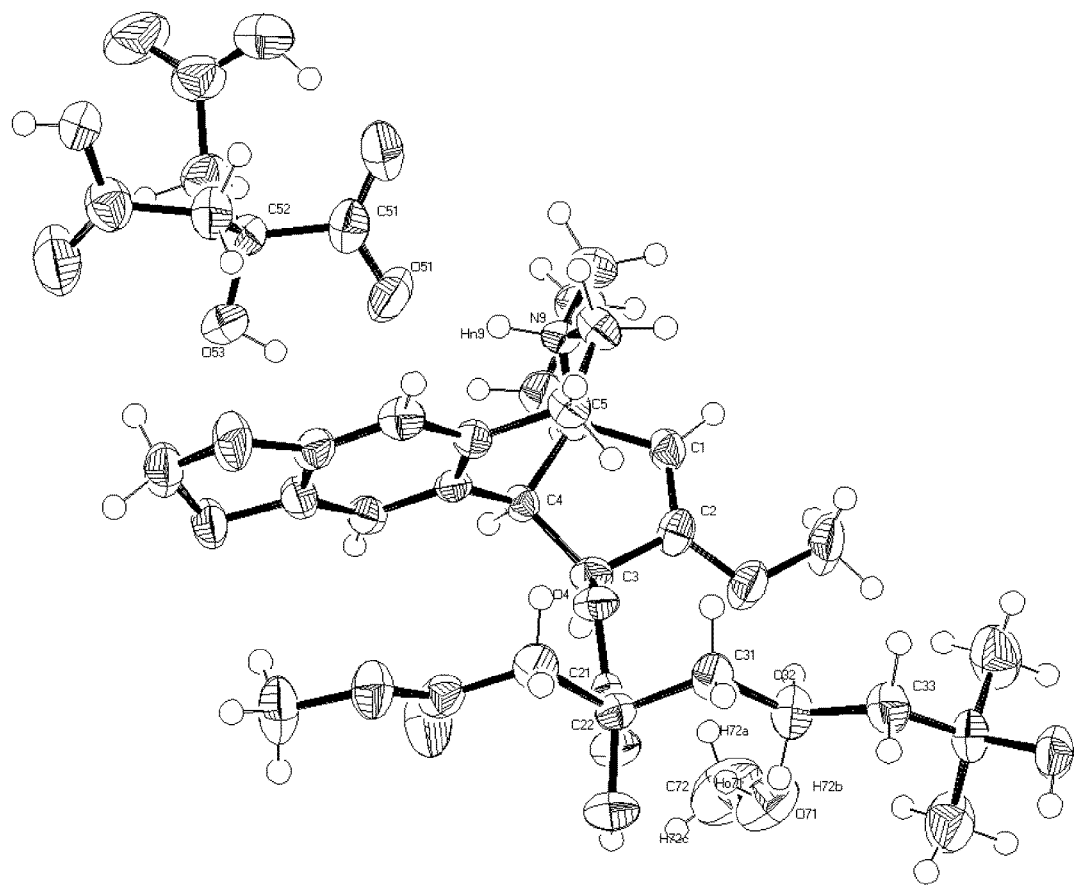

Comments

Shortest distance between anion and cation O51-Hn9 is 1.721Å (calculated by ORTEP-3). O51 is the negative charge oxygen atom of dihydrogen citrate anion and Hn9 is the proton borne by the alkaloid nitrogen. There is one methanol mol. of crystallization per asymmetric unit (H72a,H72b,H72c-C72-O71-Ho71).

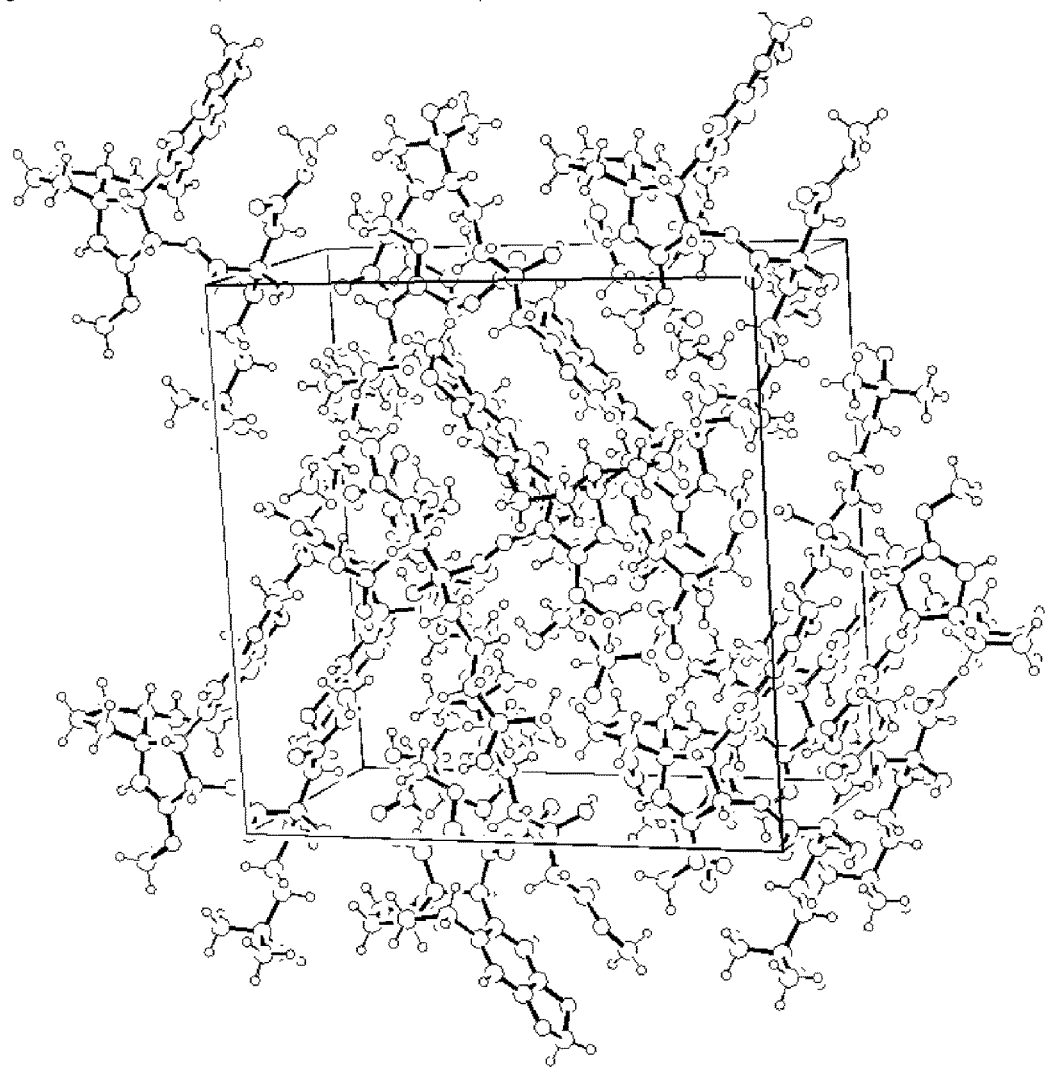
Figure 2.11.2: Single crystal X-ray diffraction of homoharringtonine dihydrogen citrate; corresponding packing with unit cell content (PLUTO, ORTEP-3 software)

Figure 2.11.3: X-ray powder diffraction (XRPD) of homoharringtonine dihydrogen citrate
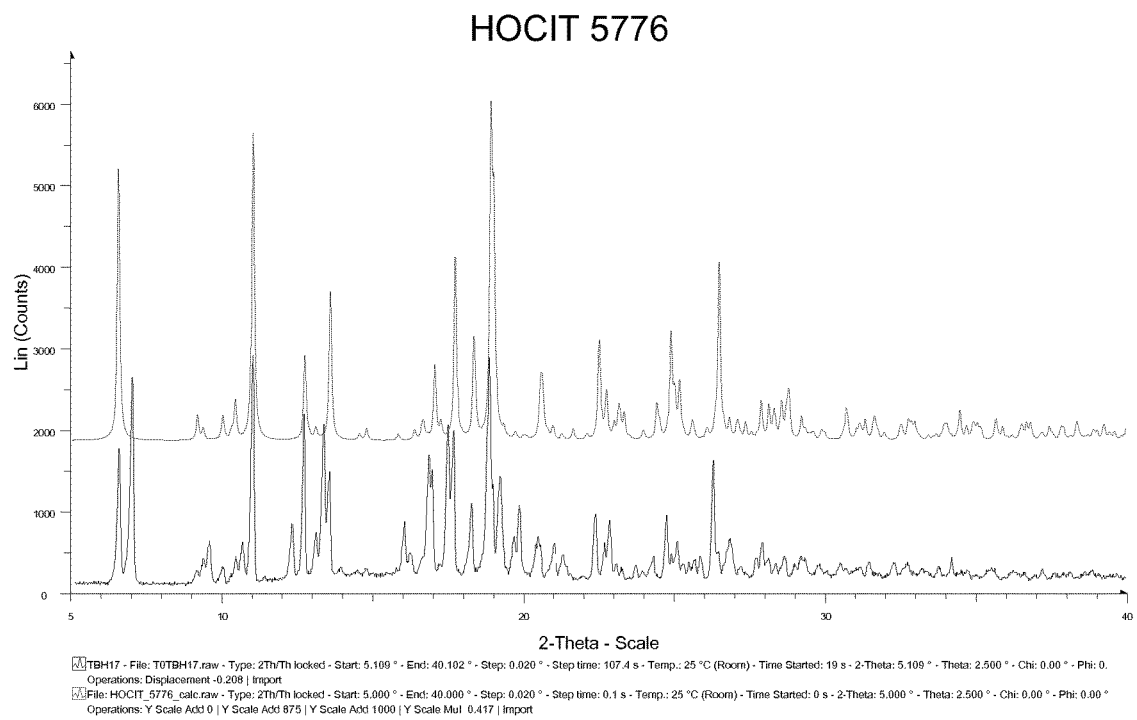

Figure 2.12.1: Single crystal X-ray diffraction of homoharringtonine salicylate (ORTEP-3 software)
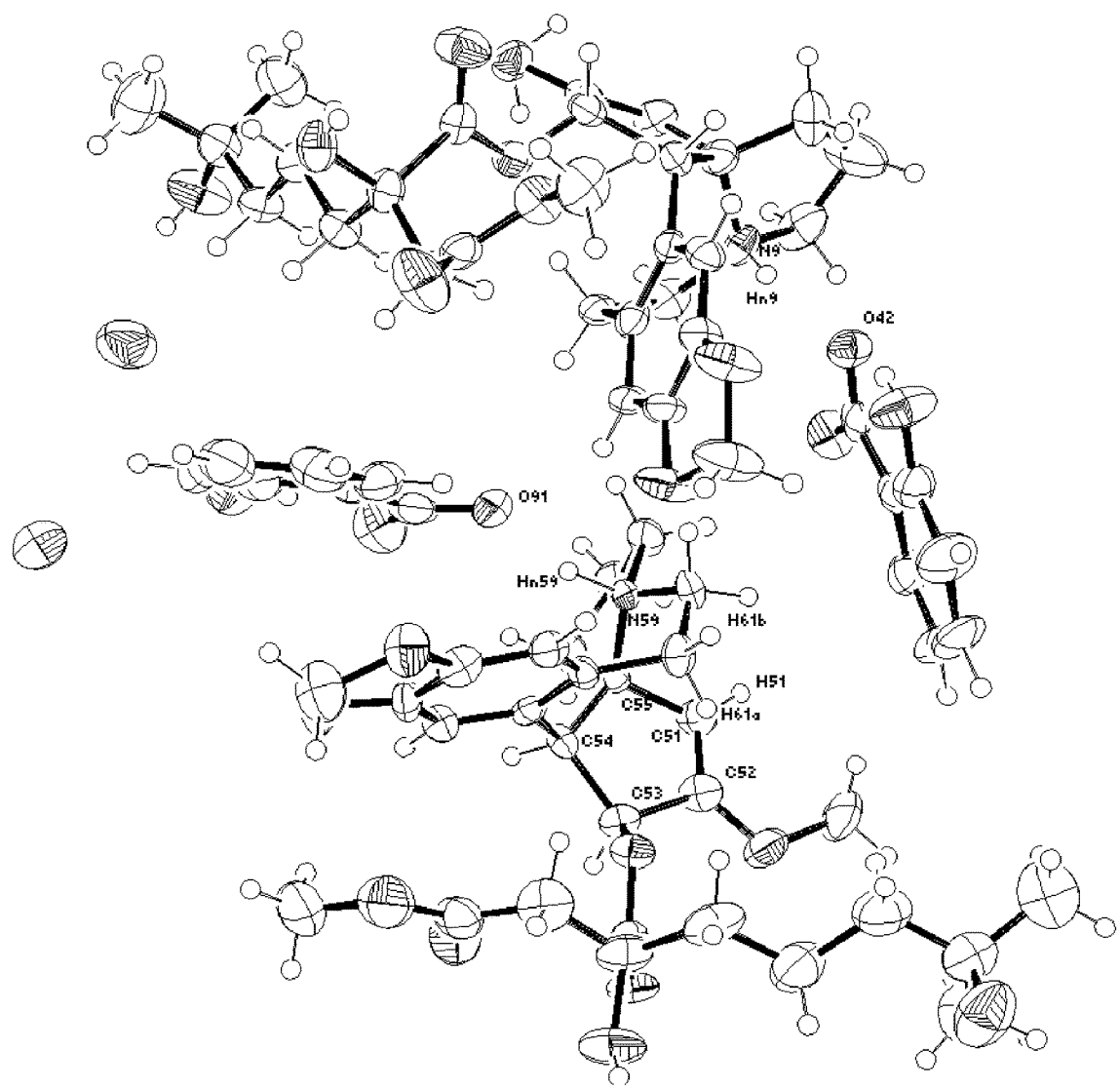

Figure 2.12.2: Single crystal X-ray diffraction of homoharringtonine salicylate (PLUTO drawing)
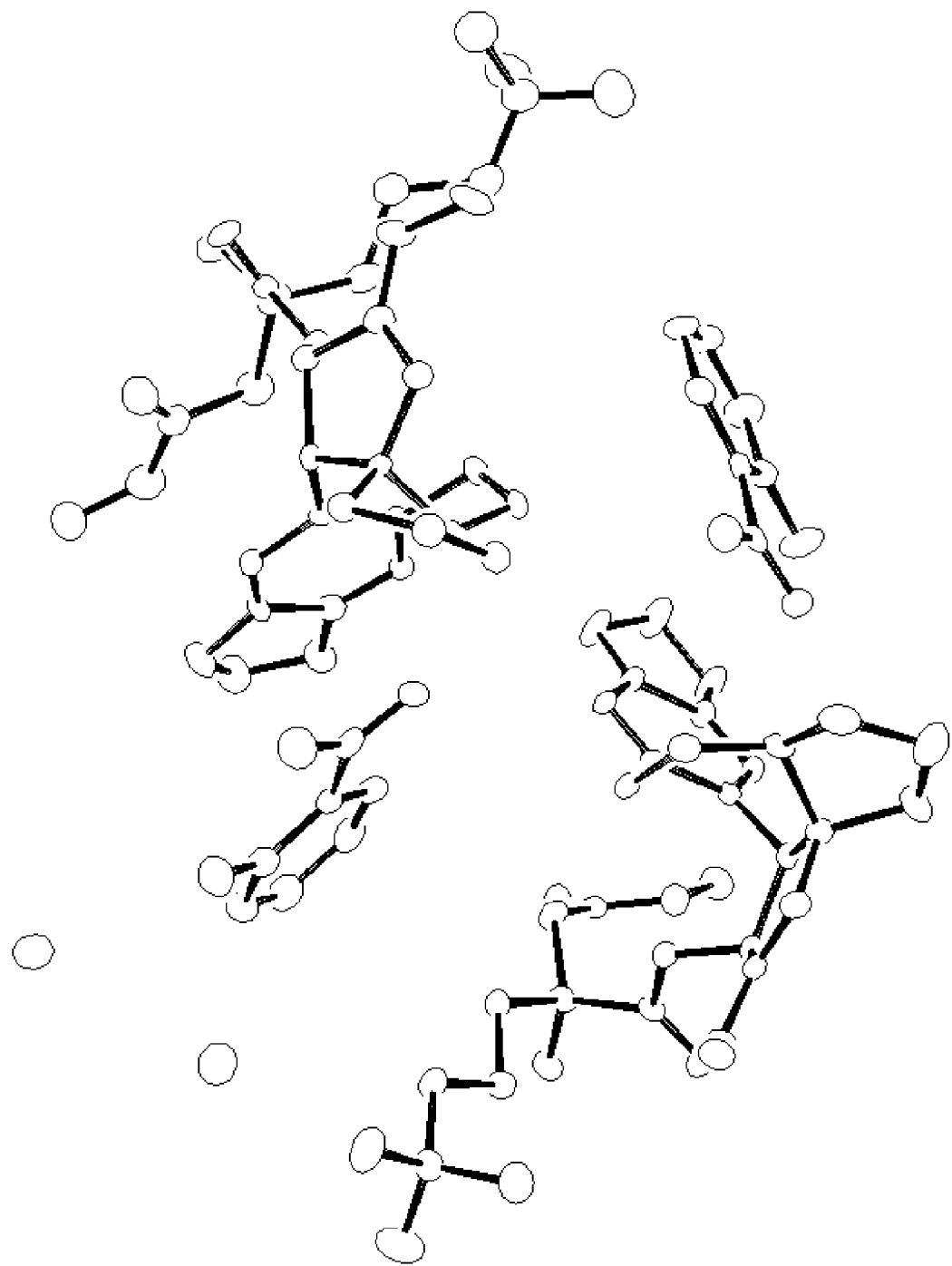

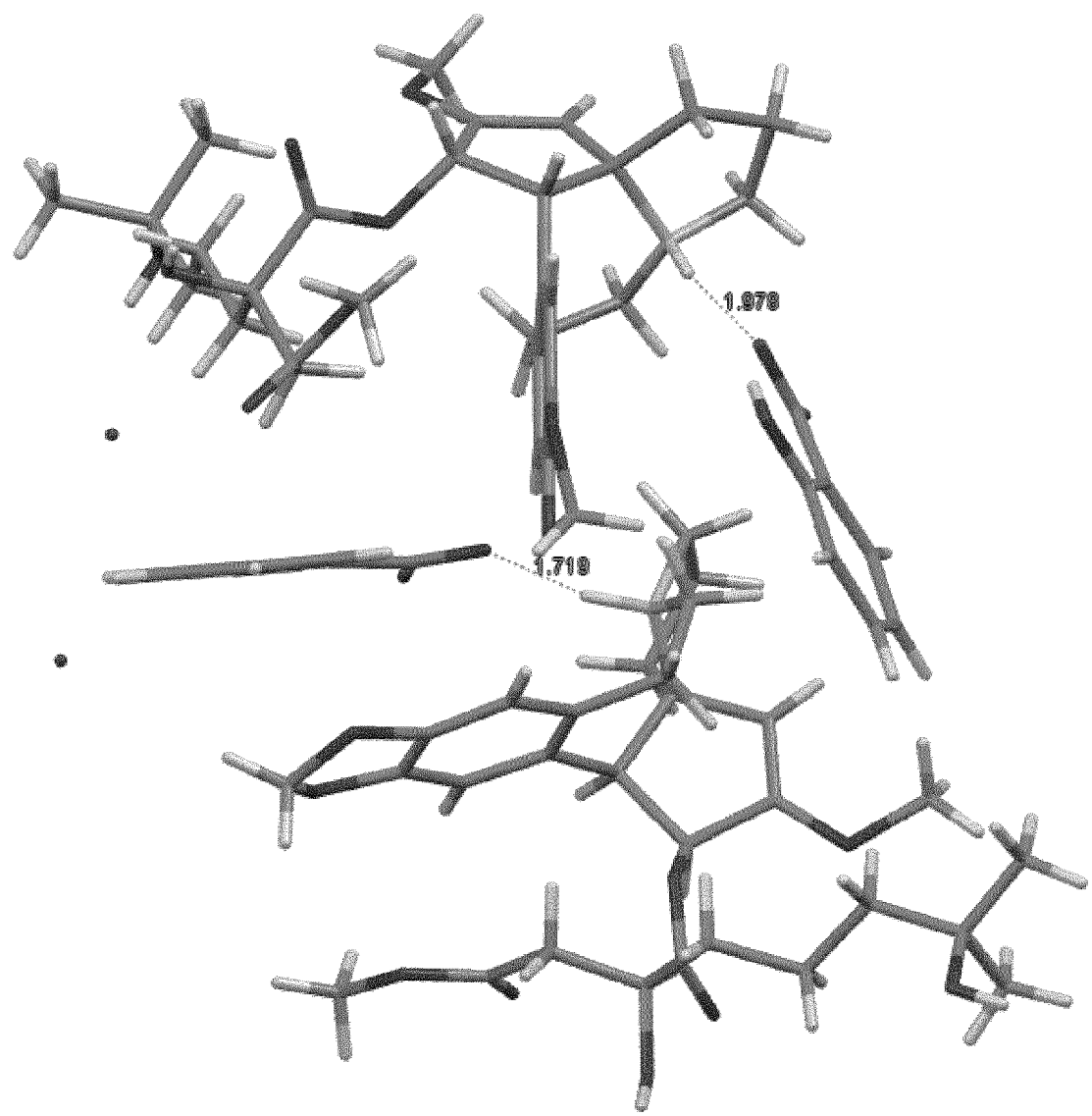
Figure 2.12.3: Single crystal X-ray diffraction of homoharringtonine salicylate (stick drawing)

Figure 2.12.4: Single crystal X-ray diffraction of homoharringtonine salicylate; corresponding packing with unit cell content (PLUTO, ORTEP-3 software)
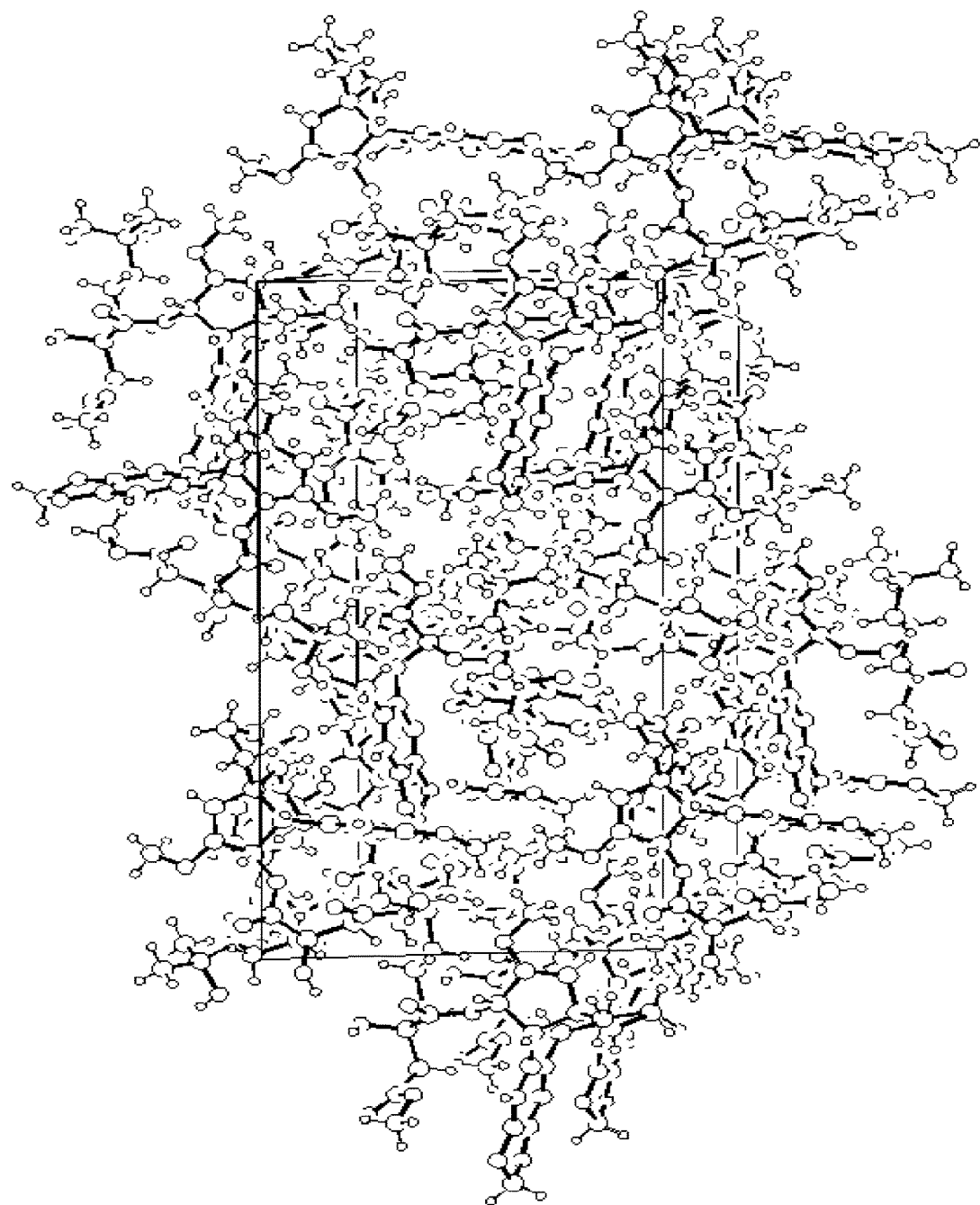

Figure 3.1 DSC pattern of homoharringtonine base
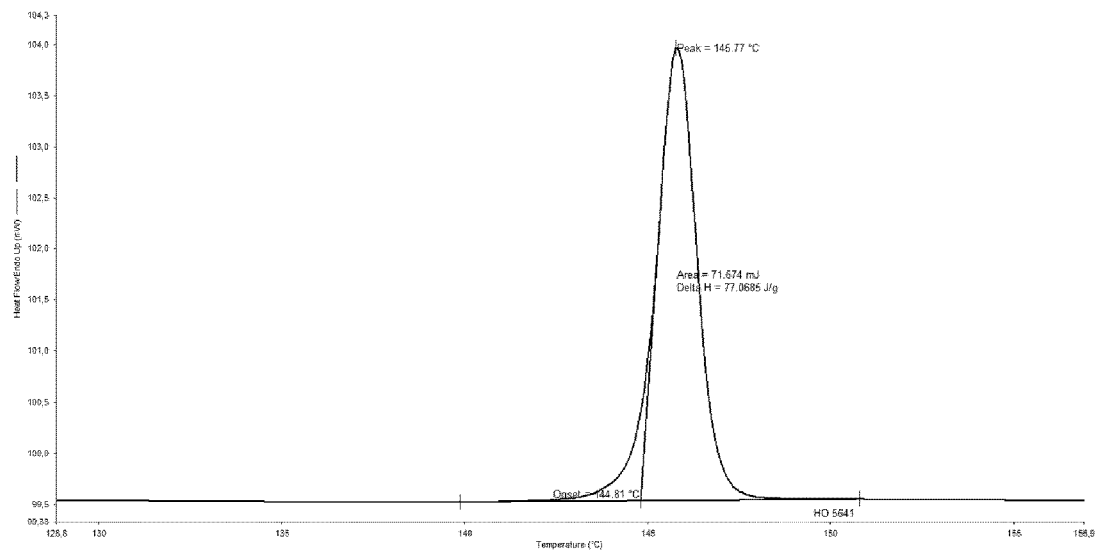
Figure 3.2 DSC pattern of homoharringtonine hydrogen (2S)-malate
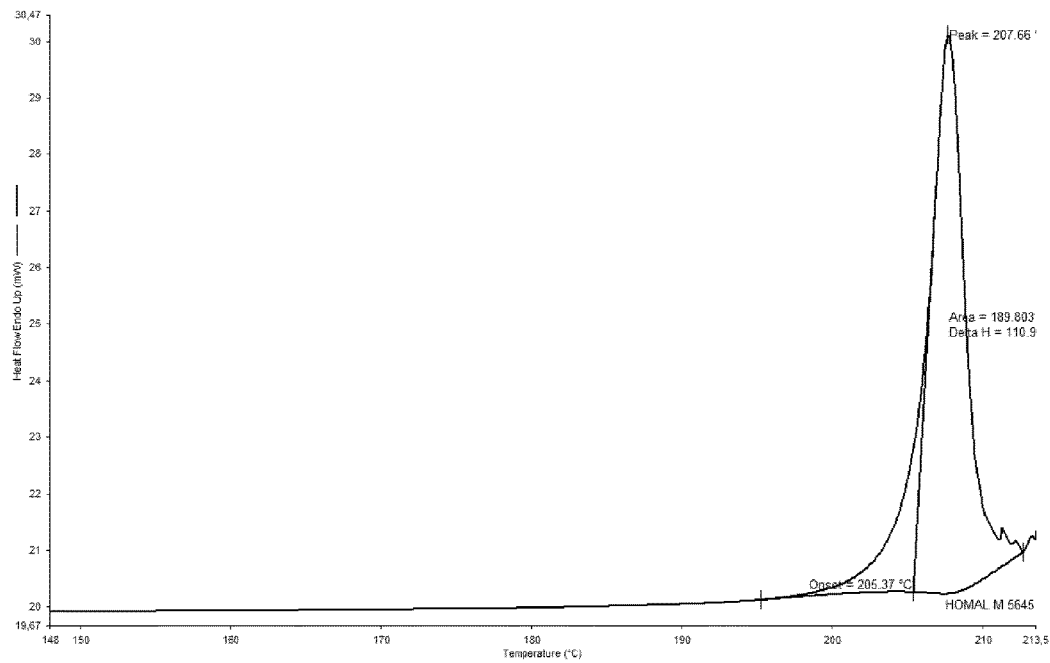

Figure 3.3 DSC pattern of homoharringtonine hydrogen (2R)-malate
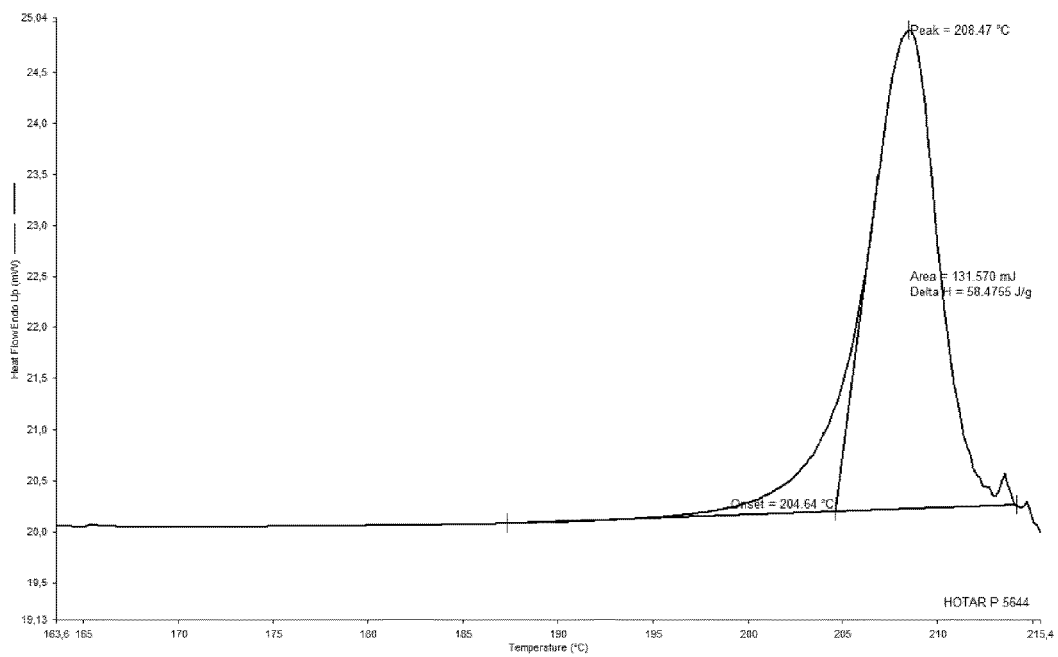
Figure 3.4 DSC pattern of homoharringtonine hydrogen (2S,3S)-tartrate
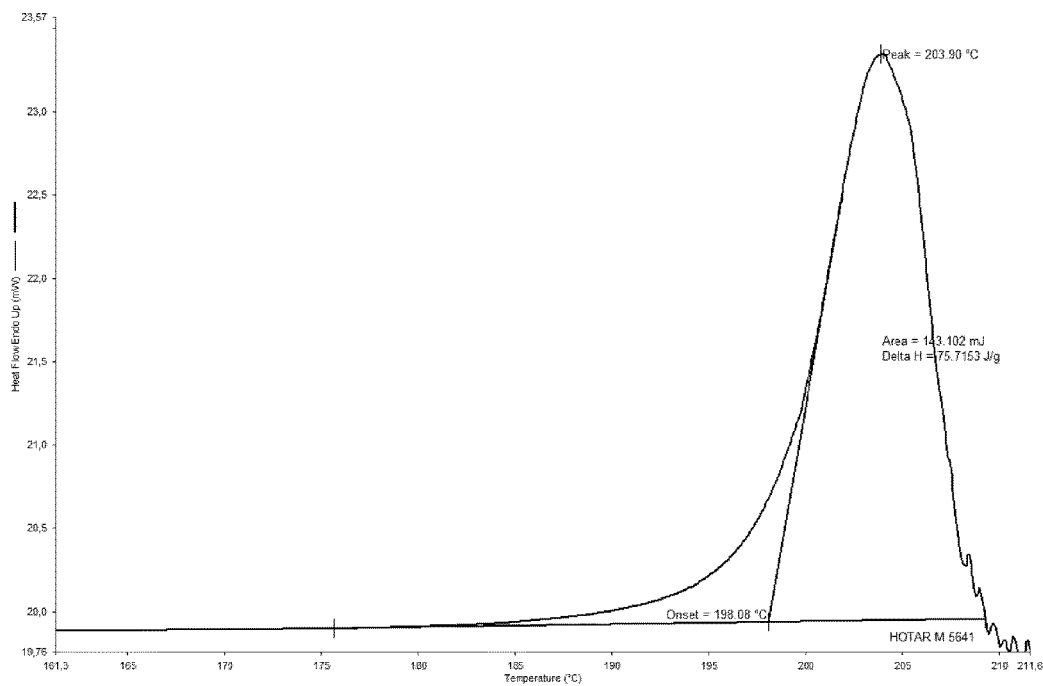

Figure 3.5 DSC pattern of homoharringtonine hydrogen (2R,3R)-tartrate
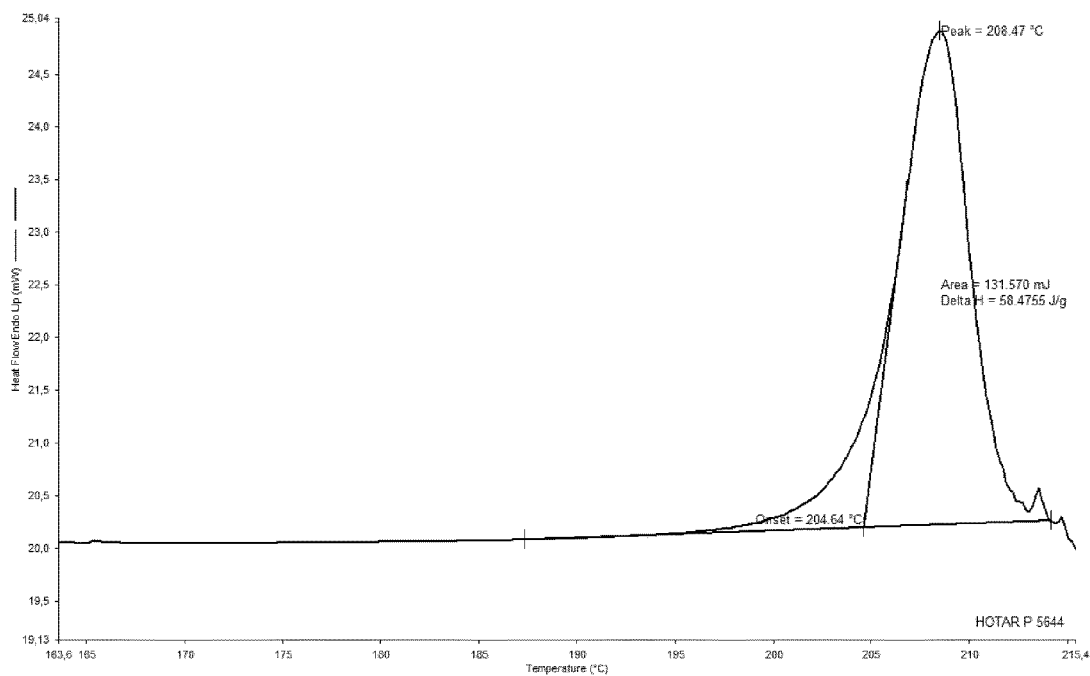
Figure 3.6 DSC pattern of homoharringtonine hydrogen (2S)-citramalate
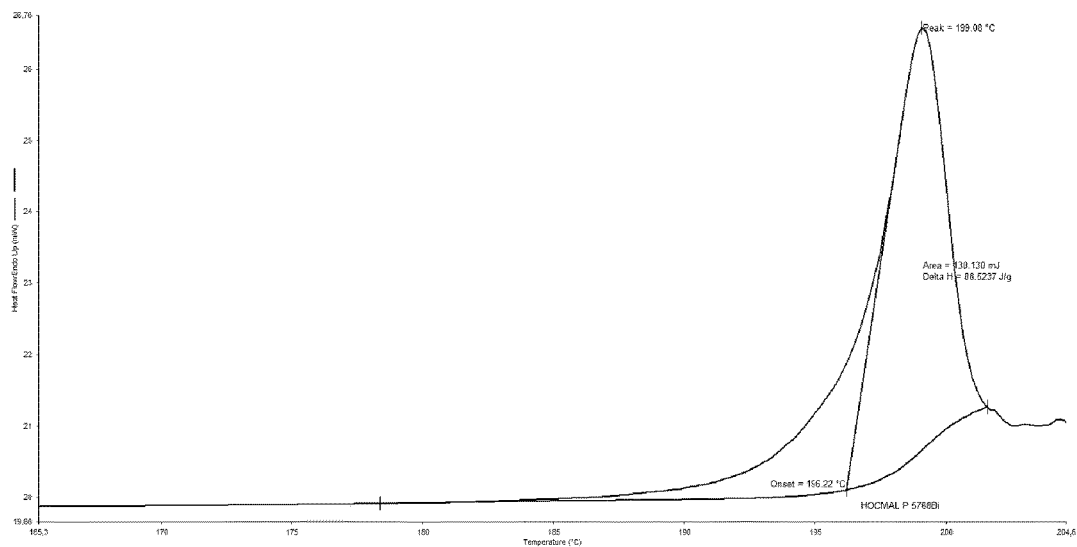

Figure 3.7 DSC pattern of homoharringtonine hydrogen (2R)-citramalate
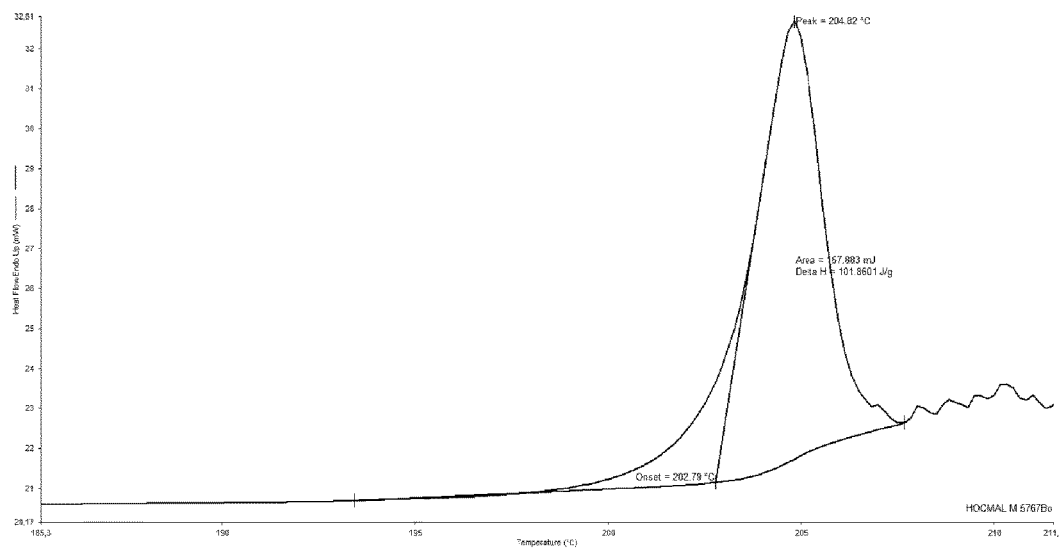
Figure 3.8 DSC pattern of homoharringtonine hydrogen succinate
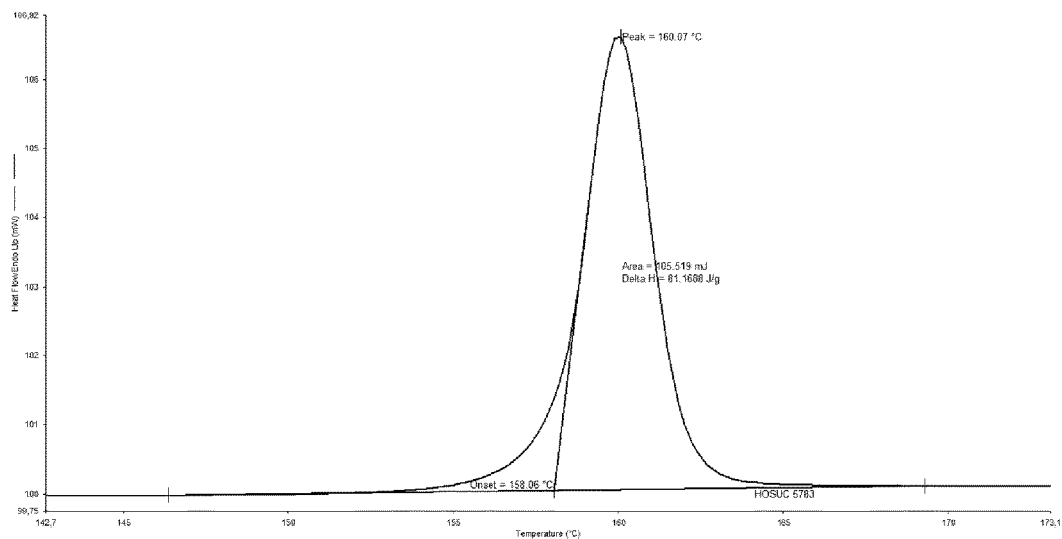

Figure 3.9 DSC pattern of homoharringtonine hydrogen itaconate
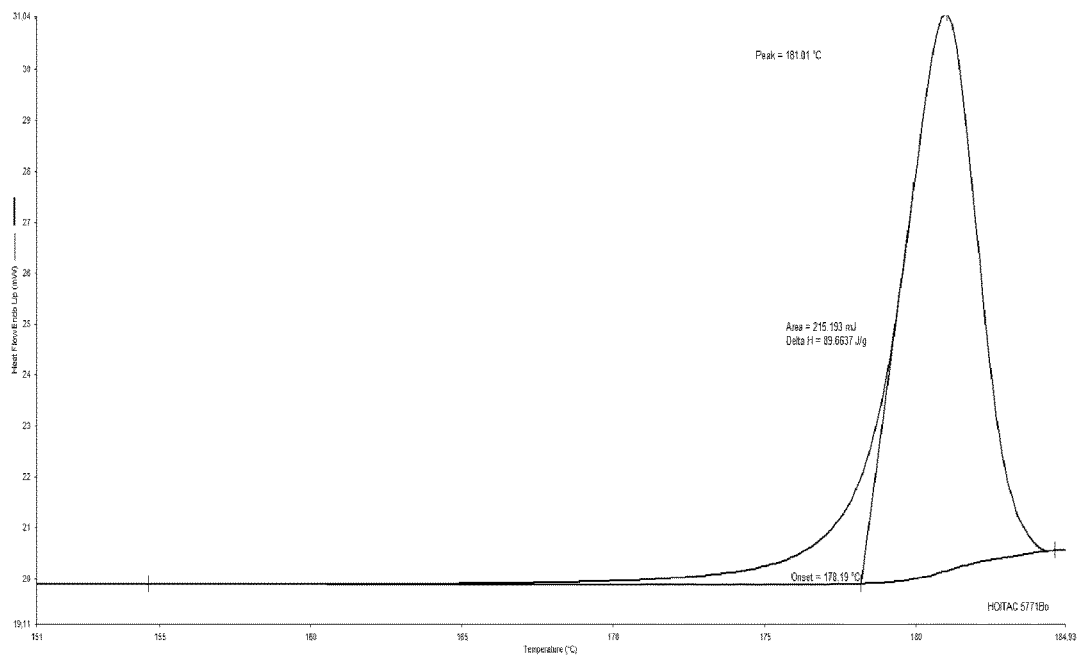
Figure 3.10 DSC pattern of homoharringtonine hydrogen fumarate
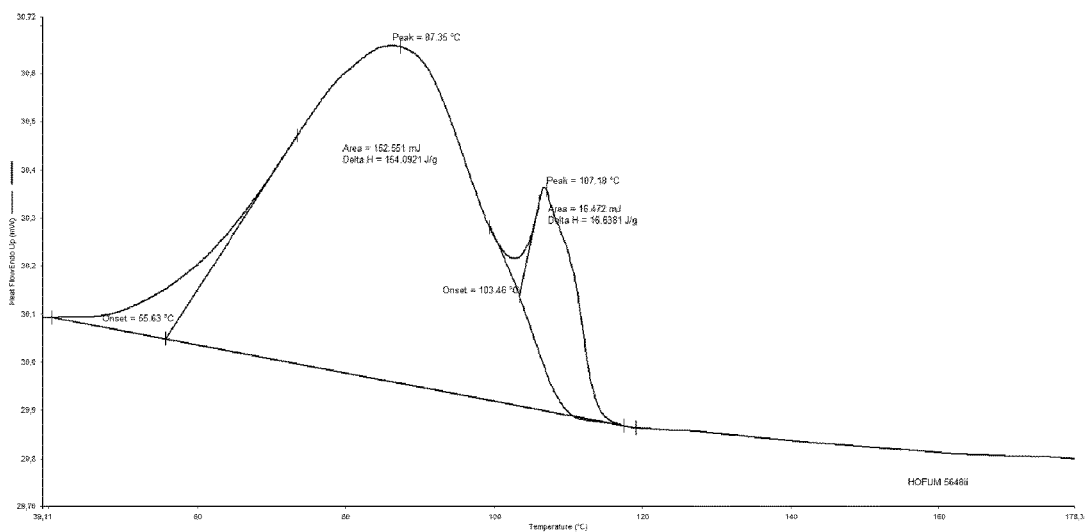

Figure 3.11 DSC pattern of homoharringtonine hydrogen tartronate
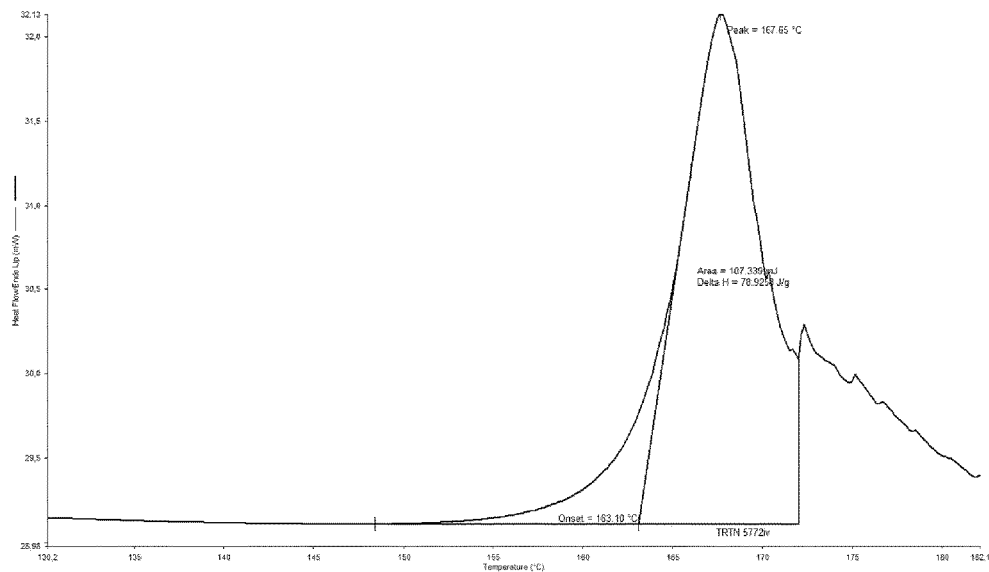
Figure 3.12 DSC pattern of homoharringtonine hydrogen malonate
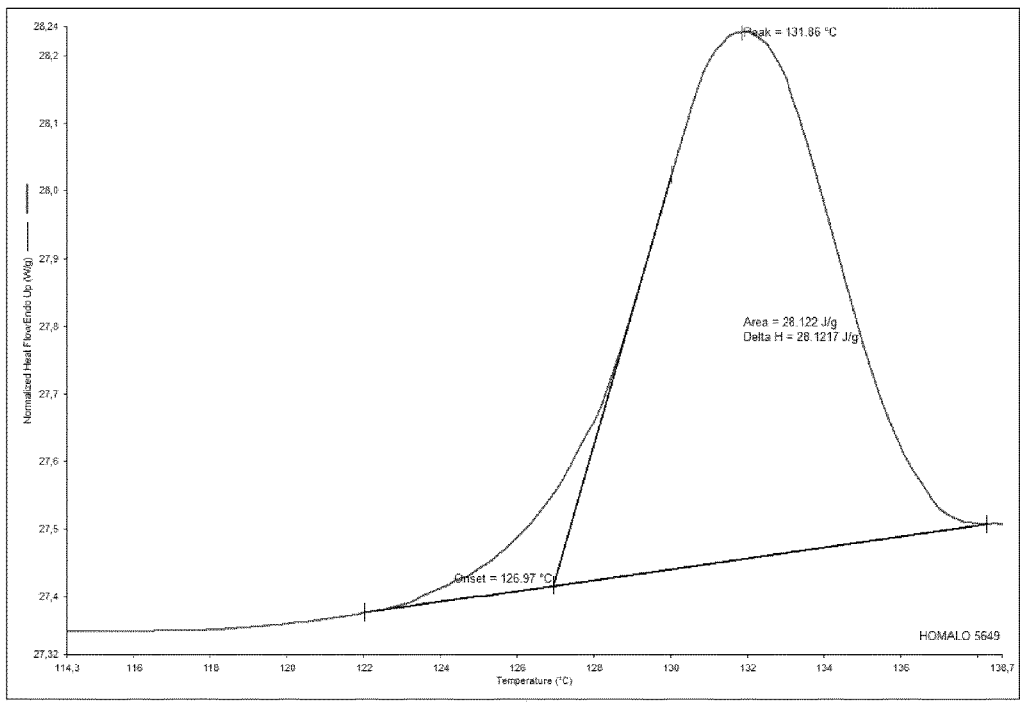

Figure 3.13 DSC pattern of homoharringtonine dihydrogen citrate
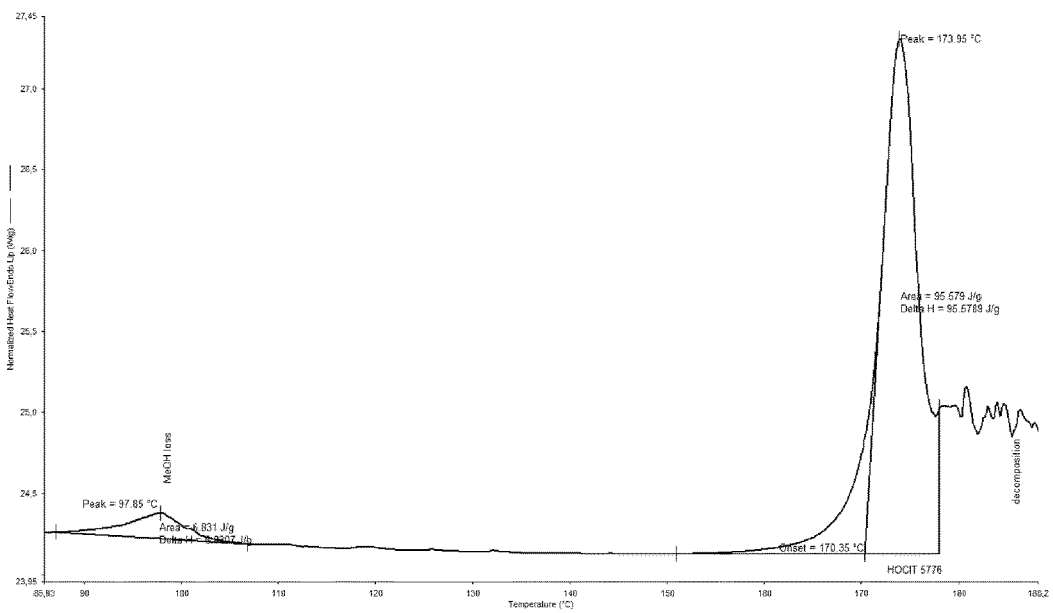
Figure 3.14 DSC pattern of homoharringtonine salicylate
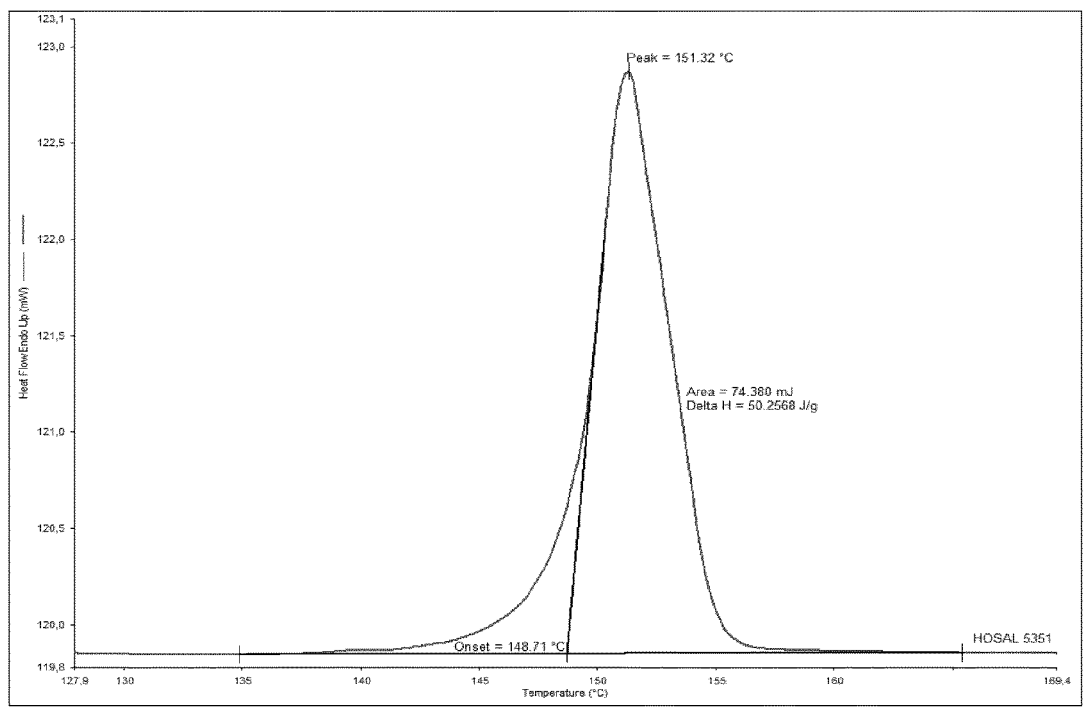

HARRINGTONINES SALTS IN THE CRYSTALLINE STATE AND THEIR USE FOR THE PURIFICATION OF THE CORRESPONDING DRUG SUBSTANCE

CROSS REFERENCE TO RELATED APPLICATIONS

This application is a U.S. National Stage application of PCT/EP2014/079456 filed Dec. 30, 2014, which claims the domestic benefit of filing of U.S. Provisional Application No. 61/941,723 filed Feb. 19, 2014, and U.S. Patent Application No. 61/922,248 filed Dec. 31, 2013, the disclosures of all of these patent applications are incorporated herein by reference in their entirety.

The present invention concerns crystalline salts of harringtonines, protonated on their alkaloid nitrogen, definite by their solid state analysis patterns, their process of preparation allowing their use as drug substance for blending alone or in combination in pharmaceutical composition useful for chemotherapy of cancer, parasit and viral diseases and/or as immunosuppressive agents, particularily in using oral or parentheral modes of administration.

Among harringtonines, omacetaxine D.C.I. (=OMA, formerly homoharringtonine=HHT) is a natural ester of cephalotaxine (see scheme 1 and table 1), an alkaloid of *Cephalotaxus harringtonia*, a rare and endangered Asian conifer belonging to Cephalotaxaceae family. OMA/HHT content in renewable parts of *Cephalotaxus* is about a few dozen of mg only per kilo of dry plant material. This characteristic, in despite of considerable efforts performed by the U.S. National Cancer Institute, hampered clinical development of omacetaxine for more than thirty-years. In 1998, the discovering of a new hemi-synthetic process by one of us (JPR), allowed industrial production of homoharringtonine at the kilo scale [ref TL] and divided by 70 the need of rare plant material [ref Nicolini].

Important Note:

It should be pointed out that chemical structure of hemi-synthetic omacetaxine is strictly identical to the natural one version: omacetaxine is not a semi-synthetic derivative as indicated in some article published in literature (see scheme 1 and table1) [ref]. All denominations of omacetaxine (OMA) or homoharringtonine (HHT) included in this document are strictly equivalent. The sentence "omacetaxine is a semi-synthetic derivative of cephalotaxine" encountered in literature, is totally devoid of scientific significance: the semi-synthetic appellation suggests that a moiety of the molecule (cephalotaxine) would natural and that the other moiety (the side chain) would be unnatural (man designed) while the latter is strictly natural. When only a portion of a molecule was produced by synthesis, the process name is hemi-synthesis and the molecule is sometimes also called hemi-synthetic.

Short History of Recent Development of Homoharringtonine.

Initially, all above esters of cephalotaxine were discovered by U.S. teams [ref powel:] and a large development program was performed by the United States National Cancer Institute [ref suff]. In October 2012, the United States Food and Drug Administration (FDA) granted accelerated approval for omacetaxine mepesuccinate for the treatment of adult patients with chronic or accelerated phase chronic myeloid leukemia (CML) who failed to responde to two or more tyrosine kinase inhibitors (TKIs) [ref fda]. Since this approval, at least a hundred articles or reviews related to OMA/HHT were published in literature [ref pub med]. Definitive approval of OMA/HHT was granted in 2014. This occurred after a very long and tumultuous period of clinical development [kanta], including early clinical development of HHT and, to a lesser extent, its congeners harringtonine (HA) and deoxyharringtonine (DHA) in various institution in the U.S. and in China. Finally the successive involvement of seven pharmaceutical companies (Vivorex/American Bioscience; Oncopharm; Stragen; Chemegenex; Cephalon; TEVA) dispatched in 5 countries occurred before approval of omacetaxine! More than 50 clinical trials in USA, China and France involving more than 2000 patients.

Definition (See Scheme 1 and Table 1)

Homoharringtonine/Omacetaxine Mepesuccinate/Synribo/Myelostat

The INN (International Non-proprietary Name) "omacetaxine mepesuccinate" (OMA) is a name reserved for homoharringtonine HHT drug substance dedicated for pharmaceutical and medicinal use regardless its natural, hemi-synthetic or synthetic origin [formerly named homoharringtonine]. Synribo (TEVA) and Myelostat (Oncopharm corporation) are trademark (Ref the Oncologist).

Cephalotaxanes Including Numbering

Cephalotaxanes are particular alkaloids to date exclusively extracted from the

Cephalotaxaceae family which exhibit the structural formula 1. Several substituants may be encountered on this core structure: hydroxyl, ether, acyloxy etc. The eventual presence of some additional double bound or intramolecular bridge achieve to definite cephalotaxanes. Cephalotaxines 2 are cephalotaxanes without acyloxy side-chain.

Cephalotaxine 2a and drupacine 2b are example of cephalotaxines. Harringtonines 5 are particular cephalotaxanes formed by attachment of a branched α-hydroxyacyloxy side-chain at the 3-position of various cephalotaxines moieties. Cephalotaxines 2 and harringtonines 5, are examples of cephalotaxanes. Several dozen of cephalotaxanes have been isolated from various *Cephalotaxus* species. 4 is the generic formula of cephalotaxine esters [ref Takano].

Harringtonines 5 (i.e. harringtonine=HA and homoharringtonine=HHT) are particular cephalotaxine esters. Cephalotaxine and its natural ester are gathered under the generic term of cephalotaxane.

Harringtoids are semi-synthetic derivatives of harrintonines.

Harringtonic acids are side-chain of harringtonines

TABLE 1

NATURAL AND SEMI-SYNTHETIC ESTERS OF CEPHALOTAXINE

| # | Trivial name | $R_2$ | $R_3$ | $R_4$ | Note # | Activity* |
|---|---|---|---|---|---|---|
| 5a | harringtonine | $(CH_3)_2COH-(CH_2)_2-$ | Me | H | (1) | anticancer |
| 5b | homoharringtonine | $(CH_3)_2COH-(CH_2)_3-$ | Me | H | (2) | anticancer |
| 5c | norharringtonine | $(CH_3)_2COH-CH_2-$ | Me | H | (3) | none |
| 5d | deoxyharringtonine | $(CH_3)_2CH-(CH_2)_2-$ | Me | H | (4) | anticancer |
| 5e | bishomoharringtonine | $(CH_3)_2COH-(CH_2)_4-$ | Me | H | (5) | none |
| 5f | isoharringtonine | $(CH_3)_2CH(CH_2)_2-$ | Me | OH | (6) | none |

TABLE 1-continued

NATURAL AND SEMI-SYNTHETIC ESTERS OF CEPHALOTAXINE

| # | Trivial name | $R_2$ | $R_3$ | $R_4$ | Note # | Activity* |
|---|---|---|---|---|---|---|
| 5g | neoharringtonine | $C_6H_5$—$CH_2$— | Me | H | (7) | cytotoxic |
| 5h | harringtonines | $R_2$— | Me | $R_4$ | (8) | N/A |
| 5i | harringtoids | $R_2$— | $R_3$ | $R_4$ | (9) | cytotoxic |

*In cancer area, for definition of term see [Suffness et al in Journal of Natural Products 1982 p 1 Current Status of the NCI Plant and Animal Product Program] CYTOTOXICITY is toxicity to tumor cells in culture; ANTITUMOR is in vivo activity in experimental systems; ANTINEOPLASTIC or ANTICANCER iare the reserved terms for reportied clinical trials data.
(1) The first cephatotaxine ester isolated from *cephalotaxus harringtonia*
(2) "Homo" means one more carbone than harringtonine; Named omacetaxine (D.C.I.) as active pharmaceutical ingredient
(3) "nor" means one more less carbone

SCHEME 1: DEFINITION NOMENCLATURE AND NUMBERING OF CEPHALOTAXANES

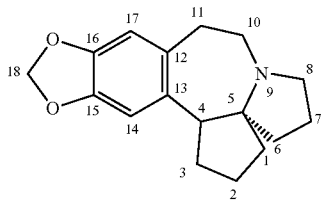

1
CEPHALOTAXANES skelton

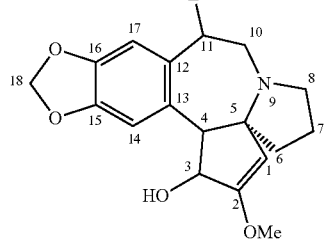

2
CEPHALOTAXINES
for example: cephalotaxine Z = H;
11-hydroxy-cephalotaxine Z = OH

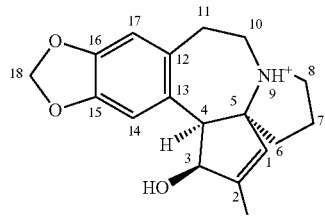

3
CEPHALOTAXINE CATION = cephalotaxinium ion

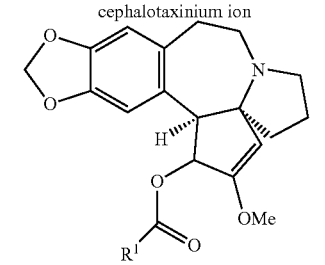

4
simple cephalotaxine esters
i.e. acetates, itaconate, pivalate etc

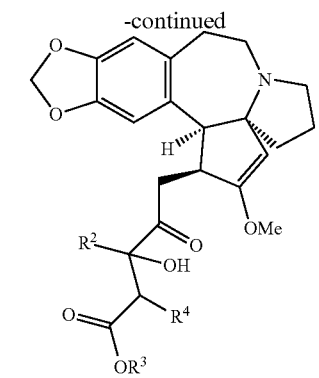

5
harringtonines and examples of semi-synthetic derivatives
see table 1

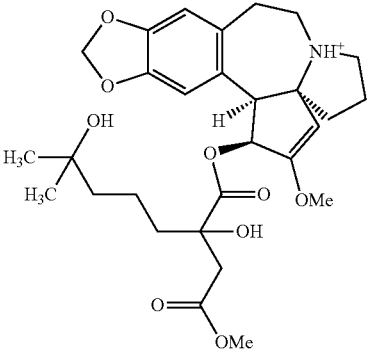

6
The homoharringtonine cation:
this patent salts

Two harringtonines are very promising drugs in the treatment of certain leukemia such as Chronic Myelogenous Leukemia (CML). Both homoharringtonine and harringtonine were used in human chemotherapy of leukemia for 30 years.

We described here new highly purified cristallin forms of certain harrintonines [ref] but, surprisingly, never crystalline salts of harringtonines have been isolated and described in literature However, in spite of the progress recorded in production, purification and therapeutic use of homoharringtonine, several disadvantages persist.

i) The cost of treatment for omacetaxine (Synribo) is prohibitive: $28,000 for induction, $14,000 for monthly treatments), this give about 180.000 $ per year, per patient [Kantarjian et al. Journal of Clinical Oncology, 2013, p3600; Hagop Kantarjian, personal communication]

ii) The use of the parenteral route of administration even retards the development of this drug iii) Preparation of formulations for parenteral use is complicated by the use of lyophilization iv) Formation of non crystalline salts of harrintonines give not as accurately definited compound as crystalline salts v) There is some local intolerance to this product when administered subcutaneously vi) On the other hand, although it has been known for almost 40 years, there is still a slight doubt regarding the absolute configuration of this series of natural product Recent scientific discovering regarding mechanism of activity of harringtonines The team Steitz [Journal of Molecular Biology (2009), 389(1), 146-156] recently demonstrated that homoharringtonine when in place in its active site was protonated in a neutral media, implying that alkaloid nitrogen protonation is imperative condition for the manifestation of the activity of this ligand.

In addition, the team of Takano et al [J. Org. Chem. 8251 (1997)] demonstrated experimentally that when the nitrogen lone pair of homoharringtonine was occupied by an oxygen atom, the cytotoxic activity was divided by a factor of at least 50. The authors conclude that "the nitrogen lone pair on the cephalotaxine skeleton appears to be essential for its activity".

The above mentioned team of Steitz showed that the absolute configuration of homoharringtonine deposited in the Cambridge Structural Database seems to be the opposite of that commonly adopted in the literature.

The present invention relates to overcome the problems mentioned above. It also demonstrated that the absolute configuration in the deposited homoharringtonine Cambridge Structural Database seems to be the opposite of that commonly retained in the literature.

The eight example of single crystal X-ray diffraction of homoharringtonine salt exhibited in FIGS. 2.3.1, 2.4.1, 2.5.1, 2.6.1, 2.8.1, 2.9.1, 2.11.1 and 2.12.1 clearly indicates that the alkaloid moiety was efficiently protonated by the processes described in the present invention. Moreover, the shortest distance between said proton carried by the nitrogen is close to two angstroms, showing the reality of the formation of a salt and not a mere co-crystal.

SCHEME 2: EXAMPLE OF ANION MOEITIES CITED IN THIS INVENTION

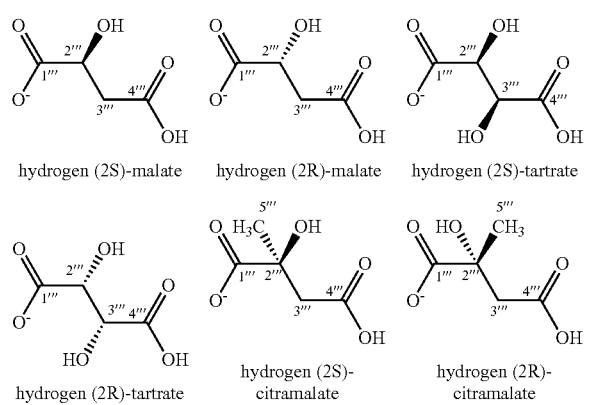

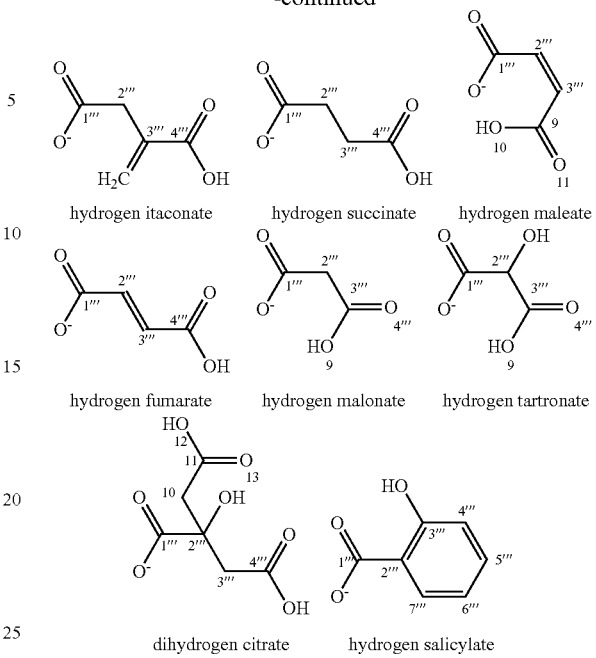

The present invention relates to overcome the problems mentioned above, namely:
raise doubt on the absolute configuration of harringtonines
provide a method of administration of harringtonines protonated on their nitrogen atom As detailed above, the fact that the real active form of harringtonines would be their nitrogen-protonated version was recently supported by the work of Seitz et al. and, indirectly by the work of Takano et al.

The present invention concerns novel water soluble crystalline salts of homoharringtonine and their use as new chemical entities for the formulation of new cancer chemotherapeutic agents, or immunosuppressive or antiparasitic and to implement new processes for purification including enantiomeric and determine the absolute configuration of the series.

The present invention describes the preparation of crystalline salts of harringtonines as nitrogen-protonated form, stable and soluble in water and their use for the manufacture of pharmaceutical composition useful in the treatment of cancers, leukemias, immune disease and as reversal agents.

The present invention describes a unambiguously proved method of protonation of harringtonine nitrogen.

The present invention provides salts of harringtonines in the solid state, protonated on their alkaloid nitrogen, definite by their solid state analysis patterns, their process of preparation from harringtonines and commercial organic acid allowing their use as drug substance for blending alone or in combination in pharmaceutical composition particularly useful for treatment of cancer in using oral mode of administration.

BRIEF DESCRIPTION OF DRAWINGS

FIG. 1.1 is infra-red (IR) spectrum of Homoharringtonine (base alkaloid). FIG. 1.1 (i) is IR(ATR) spectrum in the crystalline state. FIG. 1.1 (ii) is IR(ATR) spectrum in the amorphous state.

FIG. 1.2 is infra-red (IR) spectrum of Homoharringtonine hydrogen (S)-malate in the solid state. FIG. 1.2 (i) is IR(ATR) spectrum in the crystalline state. FIG. 1.2 (ii) is IR(ATR) spectrum in the amorphous state (film).

FIG. 1.3 is infra-red (IR) spectrum of Homoharringtonine hydrogen (R)-malate in the solid state. FIG. 1.3 (i) is IR(ATR) spectrum in the crystalline state. FIG. 1.3 (ii) is IR(ATR) spectrum in the amorphous state (film).

FIG. 1.4 is infra-red (IR) spectrum of Homoharringtonine hydrogen (2S,3S)-tartrate in the solid state. FIG. 1.4 (i) is IR(ATR) spectrum in the crystalline state. FIG. 1.4 (ii) is IR(ATR) spectrum in the amorphous state (film).

FIG. 1.5 is infra-red (IR) spectrum of Homoharringtonine hydrogen (2R,3R)-tartrate in the solid state. FIG. 1.5 (i) is IR(ATR) spectrum in the crystalline state. FIG. 1.5 (ii) is IR(ATR) spectrum in the amorphous state (film).

FIG. 1.6 is infra-red (IR) spectrum of Homoharringtonine hydrogen (2′′′S)-citramalate in the solid state. FIG. 1.6 (i) is IR(ATR) spectrum in the crystalline state. FIG. 1.6 (ii) is IR(ATR) spectrum in the amorphous state (film).

FIG. 1.7 is infra-red (IR) spectrum of Homoharringtonine hydrogen (2′′′R)-citramalate in the solid state. FIG. 1.7 (i) is IR(ATR) spectrum in the crystalline state. FIG. 1.7 (ii) is IR(ATR) spectrum in the amorphous state (film).

FIG. 1.8 is infra-red (IR) spectrum of Homoharringtonine succinate. FIG. 1.8 (i) is IR(ATR) spectrum in the crystalline state. FIG. 1.8 (ii) is IR(ATR) spectrum in the amorphous state (film).

FIG. 1.9 is infra-red (IR) spectrum of Homoharringtonine hydrogen itaconate in the solid state. FIG. 1.9 (i) is IR(ATR) spectrum in the crystalline state. FIG. 1.9 (ii) is IR(ATR) spectrum in the amorphous state (film).

FIG. 1.10 is infra-red (IR) spectrum of salt named homoharringtonine hydrogen fumarate in the solid state. FIG. 1.10 (i) is IR(ATR) spectrum in the crystalline state. FIG. 1.10 (ii) is IR(ATR) spectrum in the amorphous state (film).

FIG. 1.11 is infra-red (IR) spectrum of Homoharringtonine hydrogen tartronate in the solid state. FIG. 1.11 (i) is IR(ATR) spectrum in the crystalline state. FIG. 1.11 (ii) is IR(ATR) spectrum in the amorphous state (film).

FIG. 1.12 is infra-red (IR) spectrum of Homoharringtonine malonate in the solid state. FIG. 1.12 (i) is IR(ATR) spectrum in the crystalline state. FIG. 1.12 (ii) is IR(ATR) spectrum in the amorphous state (film).

FIG. 1.13 is infra-red (IR) spectrum of Homoharringtonine dihydrogen citrate in the solid state. FIG. 1.13 (i) is IR(ATR) spectrum in the crystalline state. FIG. 1.13 (ii) is IR(ATR) spectrum in the amorphous state (film).

FIG. 1.14 is infra-red (IR) spectrum of Homoharringtonine salicyclate in the solid state. FIG. 1.14 (i) is IR(ATR) spectrum in the crystalline state. FIG. 1.14 (ii) is IR(ATR) spectrum in the amorphous state (film).

FIG. 2.2.1 is single crystal x-ray diffraction of homoharringtonine base, form A (ORTEP-3 software).

FIG. 2.2.2 is single crystal x-ray diffraction of homoharringtonine base, form B (ORTEP-3 software).

FIG. 2.2.3 is single crystal x-ray diffraction of homoharringtonine base, form B with corresponding packing with unit cell content (PLUTO drawing, ORTEP-3 software).

FIG. 2.3.1 is single crystal x-ray diffraction of homoharringtonine hydrogen (2S)-(−)-malate (ORTEP-3 software).

FIG. 2.3.2 is single crystal x-ray diffraction of homoharringtonine hydrogen (2S)-(−)-malate with corresponding packing with unit cell content (PLUTO drawing, ORTEP-3 software).

FIG. 2.3.3 is x-ray powder diffraction (XRPD) of homoharringtonine hydrogen (2S)-(−)-malate.

FIG. 2.4.1 is single crystal X-ray diffraction of homoharringtonine hydrogen (2R)-(+)-malate (created by ORTEP-3 software).

FIG. 2.4.2 is single crystal X-ray diffraction of homoharringtonine hydrogen (2R)-(+)-malate with corresponding packing with unit cell content (PLUTO drawing, ORTEP-3 software).

FIG. 2.4.3 is X-ray powder diffraction (XRPD) of homoharringtonine hydrogen (2R)-(+)-malate.

FIG. 2.5.1 is single crystal X-ray diffraction of homoharringtonine hydrogen (2S,3S)-(−)-tartarate (created by ORTEP-3 software).

FIG. 2.5.2 is single crystal X-ray diffraction of homoharringtonine hydrogen (2S,3S)-(+)-tartarate with corresponding packing with unit cell content (PLUTO drawing, ORTEP-3 software).

FIG. 2.5.3 is X-ray powder diffraction (XRPD) of homoharringtonine hydrogen (2S,3S)-(−)-tartarate.

FIG. 2.6.1 is single crystal X-ray diffraction of homoharringtonine hydrogen (2R,3R)-(+)-tartarate (created by ORTEP-3 software).

FIG. 2.6.2 is single crystal X-ray diffraction of homoharringtonine hydrogen (2R,3R)-(+)-tartarate with corresponding packing with unit cell content (PLUTO drawing, ORTEP-3 software).

FIG. 2.6.3 is X-ray powder diffraction (XRPD) of homoharringtonine hydrogen (2R,3R)-(+)-tartarate.

FIG. 2.7.1 is X-ray powder diffraction (XRPD) of homoharringtonine hydrogen (2′′′S)-citramalate.

FIG. 2.8.1 is single crystal X-ray diffraction of homoharringtonine hydrogen (2R)-(−)-citramalate (created by ORTEP-3 software).

FIG. 2.8.2 is single crystal X-ray diffraction of homoharringtonine hydrogen (2R)-(−)-citramalate with corresponding packing with unit cell content (PLUTO drawing, ORTEP-3 software).

FIG. 2.8.3 is X-ray powder diffraction (XRPD) of homoharringtonine hydrogen (2R)-(−)-citramalate.

FIG. 2.9.1 is single crystal X-ray diffraction of homoharringtonine hydrogen itaconate (created by ORTEP-3 software).

FIG. 2.9.2 is single crystal X-ray diffraction of homoharringtonine hydrogen itaconate with corresponding packing with unit cell content (PLUTO drawing, ORTEP-3 software).

FIG. 2.10.1 is X-ray powder diffraction (XRPD) of homoharringtonine hydrogen fumarate.

FIG. 2.11.1 is single crystal X-ray diffraction of homoharringtonine dihydrogen citrate (created by ORTEP-3 software).

FIG. 2.11.2 is single crystal X-ray diffraction of homoharringtonine dihydrogen citrate with corresponding packing with unit cell content (PLUTO drawing, ORTEP-3 software).

FIG. 2.11.3 is X-ray powder diffraction (XRPD) of homoharringtonine dihydrogen citrate.

FIG. 2.12.1 is single crystal X-ray diffraction of homoharringtonine salicyclate (created by ORTEP-3 software).

FIG. 2.12.2 is single crystal X-ray diffraction of homoharringtonine salicyclate (PLUTO drawing).

FIG. 2.12.3 is single crystal X-ray diffraction of homoharringtonine salicyclate (stick drawing).

FIG. 2.12.4 is single crystal X-ray diffraction of homoharringtonine salicyclate with corresponding packing with unit cell content (PLUTO drawing, ORTEP-3 software).

FIG. 3.1 is DSC pattern of homoharringtonine base.

FIG. 3.2 is DSC pattern of homoharringtonine hydrogen (2S)-malate.

FIG. 3.3 is DSC pattern of homoharringtonine hydrogen (2R)-malate.

FIG. 3.4 is DSC pattern of homoharringtonine hydrogen (2S,3S)-tartrate.

FIG. 3.5 is DSC pattern of homoharringtonine hydrogen (2R,3R)-tartrate.

FIG. 3.6 is DSC pattern of homoharringtonine hydrogen (2S)-citramalate.

FIG. 3.7 is DSC pattern of homoharringtonine hydrogen (2R)-citramalate.

FIG. 3.8 is DSC pattern of homoharringtonine hydrogen succinate.

FIG. 3.9 is DSC pattern of homoharringtonine hydrogen itaconate.

FIG. 3.10 is DSC pattern of homoharringtonine hydrogen fumarate.

FIG. 3.11 is DSC pattern of homoharringtonine hydrogen tartronate.

FIG. 3.12 is DSC pattern of homoharringtonine hydrogen malonate.

FIG. 3.13 is DSC pattern of homoharringtonine dihydrogen citrate.

FIG. 3.14 is DSC pattern of homoharringtonine salicylate.

DETAILED DESCRIPTION

A preferred embodiment of the invention is a crystalline homoharringtonine hydrogen 2S-malate having substantially the same IR spectrum, in the solid state as set out in FIG. 1.2, the same single crystal X-ray diffractogram as set out in FIGS. 2.3.1 and 2.3.2, the same X-ray powder pattern as set out in FIG. 2.3.3 and the same DSC curve as set out in FIG. 3.2.

A further preferred embodiment of the invention provides a crystalline homoharringtonine hydrogen 2R-malate having substantially the same IR spectrum, in the solid state as set out in FIG. 1.3, the same single crystal X-ray diffractogram as set out in FIGS. 2.4.1 and 2.4.2, the same X-ray powder pattern as set out in FIG. 2.4.3 and the same DSC curve as set out in FIG. 3.3.

A further preferred aspect of the invention is a crystalline homoharringtonine hydrogen (2S,3S)-tartrate having substantially the same IR spectrum, in the solid state as set out in FIG. 1.4, the same single crystal X-ray diffractogram as set out in FIGS. 2.5.1 and 2.5.2, the same X-ray powder pattern as set out in FIG. 2.5.3 and the same DSC curve as set out in FIG. 3.4.

Yet, a further embodiment of the invention is a crystalline homoharringtonine hydrogen (2R,3R)-tartrate having substantially the same IR spectrum, in the solid state as set out in FIG. 1.5, the same single crystal X-ray diffractogram as set out in FIGS. 2.6.1 and 2.6.2, the same X-ray powder pattern as set out in FIG. 2.6.3 and the same DSC curve as set out in FIG. 3.5.

Yet, another embodiment of the invention provides a crystalline homoharringtonine hydrogen (2S)-citramalate having substantially the same IR spectrum, in the solid state as set out in FIG. 1.6, the same X-ray powder pattern as set out in FIG. 2.7.1 and the same DSC curve as set out in FIG. 3.6.

Yet, a preferred aspect of this invention is a crystalline homoharringtonine hydrogen (2R)-citramalate having substantially the same IR spectrum, in the solid state as set out in FIG. 1.7, the same single crystal X-ray diffractogram as set out in FIGS. 2.8.1 and 2.8.2, the same X-ray powder pattern as set out in FIG. 2.8.3 and the same DSC curve as set out in FIG. 3.7.

Yet, another preferred aspect of this invention provides a crystalline homoharringtonine hydrogen succinate having substantially the same IR spectrum, in the solid state as set out in FIG. 1.8, and the same DSC curve as set out in FIG. 3.8.

Yet, a further preferred aspect of this invention is a crystalline homoharringtonine hydrogen itaconate having substantially the same IR spectrum, in the solid state as set out in FIG. 1.9, the same single crystal X-ray diffractogram as set out in FIGS. 2.9.1 and 2.9.2 and the same DSC curve as set out in FIG. 3.9.

Yet, a preferred aspect of this invention provides a crystalline homoharringtonine hydrogen fumarate having substantially the same IR spectrum, in the solid state as set out in FIG. 1.10, the same X-ray powder pattern as set out in FIG. 2.10.1 and the same DSC curve as set out in FIG. 3.10

Yet, an another aspect of the invention provides a crystalline homoharringtonine hydrogen tartronate having substantially the same IR spectrum, in the solid state as set out in FIG. 1.11 and the same DSC curve as set out in FIG. 3.11.

In addition, another embodiment provides a crystalline homoharringtonine hydrogen malonate having substantially the same IR spectrum, in the solid state as set out in FIG. 1.12 and the same DSC curve as set out in FIG. 3.12.

Moreover, a preferred embodiment of this invention provides a crystalline homoharringtonine dihydrogen citrate having substantially the same IR spectrum, in the solid state as set out in FIG. 1.13, the same single crystal X-ray diffractogram as set out in FIGS. 2.11.1 and 2.11.2, the same X-ray powder pattern as set out in FIG. 2.11.3 and the same DSC curve as set out in FIG. 3.13

Also, a preferred aspect of this invention provides a crystalline homoharringtonine hydrogen salicylate having substantially the same IR spectrum, in the solid state as set out in FIG. 1.14, the same single crystal X-ray diffractogram as set out in FIGS. 2.12.1, 2.12.2, 2.12.3 and 2.12.4 and the same DSC curve as set out in FIG. 3.14.

Yet, a preferred aspect of this invention provides a pharmaceutical composition comprising an effective amount of one of the salts of this invention, together with one or more pharmaceutical acceptable inactive components such as carriers, excipients, adjuvants or diluents.

Yet, a preferred aspect of this invention provides a pharmaceutical dosage form dedicated to an oral mode of administration selected among, for example, capsules, dragees, emulsions, granules, pills, powders, solutions, suspensions, tablets, microemulsions, elixirs, syrups, tea or powders for reconstitution Yet, a another aspect of this invention provides a pharmaceutical dosage form dedicated to a subcutaneous mode of administration in non-acidic condition allowing a good locale tolerance Another aspect of the invention is the use of at least the solid form of one salt described in the invention for preparing the above pharmaceutical composition as (i) chemotherapeutic agent, (ii) enhancer of other chemotherapeutic agents (iii) after failure of other agents (iv) for inhibiting tumors growth in animal, (v) for inhibiting mammalian parasites, (vi) as immunosuppressive agent, or (vii) as reversal agent.

A preferred embodiment of the invention describes a method for treating mammalian tumors which comprises oral administering to a mammal an antitumor effective amount of the solid form of one salt described in this invention.

A further preferred embodiment of the invention describes a method for treating mammalian tumors which comprises implantable pharmaceutical preparation administering to a mammal an antitumor effective amount of the solid form of at least one salt described in this invention.

Yet, invention is also concerned with the use of solid form as defined above, for the preparation of pharmaceutical compositions for the treatment of cancer particularly, ovarian serous high-grade carcinoma including those resistant to existing therapy, breast cancer including triple negative breast carcinoma and eventually their metastasis, pancreatic cancer including ductal adenocarcinoma.

Finally, the invention is also concerned with the use of solid form as defined above, for the preparation of pharmaceutical compositions for the treatment of leukemias particularly acute myelod leukemia (AML), myelodysplastic syndrome (MDS) and myeloproliferative disorders including chronic myelogenous leukemia, polycythemia vera, essential thrombocythemia, myelosclerosis.

EXAMPLE 1: GENERAL PROCEDURE FOR EXPERIMENTAL METHODS 1.1 General Procedures for Salts Preparation Cation and anion components are dissolved separately in a solvent at a concentration close of saturation and at a temperature close of boiling then both solutions are mixed under stirring then slowly cooled and evaporated. After a period ranging from a few minutes up to several days, crystal salt is collected. A sample of the batch of crystals is kept suspended in its mother liquors for the subsequent X-ray diffraction analysis. The remainder of the batch was dried under vacuum for further solid characterisation, comparative stability studies and drug formulation.

1.2 General Procedures for Solid State Characterization

Single Crystal X-Ray Diffractions Material and Methods

KappaCCD, Nonius diffractometer, Mo-Kα radiation ($\lambda=0.71073$ Å). The structure was solved by direct methods using the SHELXS-97 program [Sheldrick G. M., Acta Cryst. A64 (2008), 112-122], and then refined with full-matrix least-square methods based on $F^2$ (SHELXL-2013) [Sheldrick G. M., (2013)] with the aid of the WINGX [L. J. Farrugia, J. Appl. Cryst., 2012, 45, 849-854] program. All non-hydrogen atoms were refined with anisotropic atomic displacement parameters. Except nitrogen and oxygen linked hydrogen atoms that were introduced in the structural model through Fourier difference maps analysis, H atoms were finally included in their calculated positions.

Collected information: atomic positions; unit cell composition; crystal packing anisotropic displacement parameters; bond lengths, dihedral and torsion angles, hydrogen bounding.

Original files with all parameters are includes on a CD and may be visualized and handled in using ORTEP-3 software (ORTEP=Oak Ridge Thermal-Ellipsoid Plot Program) available free of charge on the Internet:

http://www.chem.gla.ac.uk/~louis/software/ortep3/

X-Ray Diffraction Powder

Diagrams were measured on a Bruker AXS D8 Advance diffractometer, Bragg-Brentano geometry (θ-2 θ), CuK α=1.5406 Å, 600 ms/pixel, rotation: 0.25/sec. For each chart, the calculated pattern from the single crystal structure, when available, is upped mentioned.

Differential Scanning Calorimetry (DSC)

The DSC analysis was performed using a Perkin Elmer DSC 4000 apparatus. The scan rate was 5° C./min and the scanning range of temperature 40 to 230° C. The accurately weighed quantity was ranged from 1 to 3 mg. All operations were performed under nitrogen atmosphere. The measured values were the Onset, the Peak and the value of the free enthalpy variation. The eventual product decomposition and the vaporization of solvent crystallization (methanol and/or water) were recorded. The value of the change in free energy, was given only as a guideline to assess the endothermicity or exothermicity of the transition.

Melting Point Checking

Melting points were measured manually for visual checking of the one determined with DSC. A Bücchi B-545 melting point apparatus was used and mp are uncorrected.

Infrared Spectra

All vibrational spectra were recorded on a Perkin Elmer IR FT Spectrum 2 apparatus equipped with diamond ATR accessory that is to say using Attenuated Total Reflection technique. The crystalline solids were crushed directly by in situ compression on the diamond window and the amorphous state has been demonstrated by dissolving the product in deuterated methanol then generating the film by in situ evaporation on the diamond window.

1.3 General Procedures for Liquid State and Solution Characterizations

Nuclear Magnetic Resonance

NMR spectra were recorded automatically on a Bruker Avance III spectrometer NanoBay-400 MHz (9.4 Tesla magnet) with a BBFO+ probe and sampler 120 positions, allows for automatic mode NMR experiments one and two dimensions mainly for nuclei: 1H, 2H, 11B, 13C, 15N, 19F, 27Al, 31P, 119Sn or on Bruker Avance III-600 MHz spectrometer.

Dissolving Salts for $^{13}$C NMR:

30 mg of compound were dissolved in 600 μL (5% m/V) of methanol $D_4$ or deuterium oxyde (or both if specified)

Water Suppression:

The irradiation technique known as 'watergate' (Selective pulse flanked by gradient pulses) was used for proton NMR in the presence of $D_2O$ and/or $MOD_4$ as solvents.

High Performance Liquid Chromatography

Routine experiments were performed on a Waters HPLC-MS-DAD coupled system (3100 pump, DAD 996 detector, 3100 mass detector).

Solubility Determination

Solubility in water at 25° C. was measured semi-quantitatively at a threshold of 5 g per 100 mL. All the homoharringtonine salts described in the below examples, unless otherwise stated, are soluble at this threshold. Homoharringtonine base itself is soluble at a threshold lower than 0.1 g per mL

EXAMPLE 2: ANALYSES OF HOMOHARRINGTONINE BASE FOR COMPARISON WITH ITS SALTS

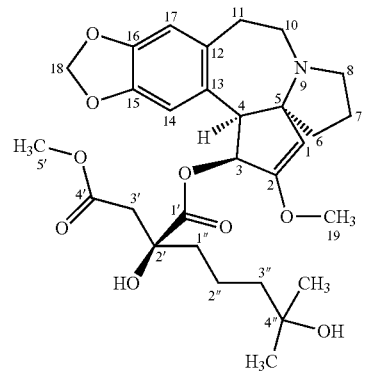 [SMILES: COC(=O)C[C@@](O)(CCCC(C)(C)O)C(=O)O[C@@H]1C(OC)=C[C@]23CCCN2CCc2cc4c(cc2[C@H]13)OCO4]

2.1 Analysis of Homoharringtonine Base Alkaloid

Bath #: 51H0092 from SIGMA

NMR spectra were performed in deuterated methanol for comparison with salt in the same solvent.

By methanol recrystallisation of a commercial alkaloid from natural source, it results fine white prisms (mp 145-146°, by DSC, see FIG. 3.1) used for all experiences.

$^1$H NMR (400 MHz, Benzene-d$_6$) δ 6.54 (s, 1H), 6.46 (s, 1H), 6.21-6.12 (m, 1H), 5.47 (d, J=1.4 Hz, 1H), 5.33 (d, J=1.4 Hz, 1H), 4.67 (s, 1H), 3.43 (d, J=9.8 Hz, 1H), 3.34 (s, 3H), 3.28 (s, 3H), 2.83 (td, J=8.5, 4.5 Hz, 1H), 2.75 (dd, J=11.5, 4.5 Hz, 1H), 2.55 (dd, J=10.8, 7.5 Hz, 1H), 2.41 (dd, J=16.2, 6.9 Hz, 2H), 2.23-2.11 (m, 2H), 1.78 (m, 1H), 1.67-1.56 (m, 2H), 1.48 (m, 5H), 1.34-1.19 (m, 2H), 1.04 (d, J=6.7 Hz, 6H).

$^1$H NMR (300 MHz, Chloroform-d) δ 6.62 (s, 1H), 6.54 (s, 1H), 6.00 (d, J=9.8 Hz, 1H), 5.87 (s, 2H), 5.05 (s, 1H), 3.78 (d, J=9.8 Hz, 1H), 3.68 (s, 3H), 3.57 (s, 3H), 3.52 (s, 1H), 3.20-3.04 (m, 2H), 3.01-2.88 (m, 1H), 2.60 (t, J=7.2 Hz, 1H), 2.38 (dd, J=13.7, 6.3 Hz, 1H), 2.26 (d, J=16.5 Hz, 1H), 2.10-1.97 (m, 1H), 1.91 (d, J=16.5 Hz, 1H), 1.75 (s, OH), 1.39 (dd, J=13.5, 6.4 Hz, 5H), 1.19 (s, 7H).

$^1$H NMR (400 MHz, Methanol-d$_4$)* δ 6.7 (s, 1H), 6.59 (s, 1H), 5.98 (dd, J=9.8, 0.8 Hz, 1H), 5.89 (d, J=1.2 Hz, 1H), 5.85 (d, J=1.2 Hz, 1H), 5.22 (d, J=0.8 Hz, 1H), 3.89 (d, J=9.8 Hz, 1H), 3.70 (s, 3H), 3.55 (s, 3H), 3.20 (ddd, J=14.1, 12.4, 7.9 Hz, 1H), 2.96 (m, 1H), 2.88 (m, 1H), 2.64 (dd, J=11.4, 7.6 Hz, 1H), 2.44 (dd, J=14.3, 6.8 Hz, 1H), 2.17 (d, J=16.1 Hz, 1H), 2.03 (m, 1H), 1.95 (m, 1H), 1.90 (d, J=16.1 Hz, 1H), 1.49-1.30 (m, 5H), 1.25 (d, J=9.8, 5.8 Hz, 1H), 1.17 (s, 3H), 1.16 (s, 3H).

*Partial presuppression of water signal using 'watergate' irradiation $^{13}$C NMR (101 MHz, MeOD) δ 174.68, 171.76, 159.97, 148.21, 147.32, 134.49, 129.88, 114.02, 110.86, 102.10, 100.74, 76.03, 75.52, 72.14, 71.35, 58.04, 56.48, 54.60, 52.00, 49.64, 44.89, 44.15, 43.86, 40.87, 32.08, 29.27, 29.01, 20.82, 19.19.

IR (KBr, solid), cm$^{-1}$ 3551.9, 3412.3, 3000.4, 2976.1, 2966.0, 2958.6, 2911.4, 2876.0, 2814.4, 2740.8, 1743.0, 1653.5, 1624.7, 1505.3, 1488.1, 1454.8, 1436.1, 1411.2, 1392.8, 1377.7, 1367.2, 1346.3, 1306.4, 1274.3, 1261.5, 1230.0, 1190.8, 1162.1, 1135.3, 1119.9, 1082.0, 1027.9, 1000.5, 932.1, 900.6, 879.3, 854.2, 827.3, 804.9, 795.2, 772.4, 762.9, 738.3, 705.7, 674.0, 661.4, 610.8, 556.7, 540.9, 522.1, 512.8, 503.3. See FIG. 1.1

A) Single Crystal X Ray Diffraction of Homoharringtonine Base (Form A)

See Corresponding FIG. 2.2.1

From a suspension in its mother liquor, a suitable single crystal of size 0.5×0.4×0.4 mm was finally selected and implemented on the diffractometer.

| Structural data: | |
|---|---|
| Empirical formula | C$_{29}$H$_{39}$N$_1$O$_9$ |
| Formula weight | 545.61 |
| Temperature | 293(2) K |
| Wavelength | 0.71073 Å |
| Crystal system, space group | orthorhombic, P 2$_1$ 2$_1$ 2$_1$ |
| Unit cell dimensions | a = 11.9512(2) Å, α = 90° |
|  | b = 15.2211(2) Å, β = 90° |
|  | c = 15.9670(2) Å, γ = 90° |
| Volume | 2904.56(7) Å$^3$ |
| Z, Calculated density | 4, 1.248 (g · cm$^{-1}$) |
| Absorption coefficient | 0.092 mm$^{-1}$ |
| F(000) | 1168 |
| Crystal size | 0.5 × 0.4 × 0.4 mm |
| Crystal color | colourless |
| Theta range for data collection | 2.881 to 29.046° |
| h_min, h_max | −16, 16 |
| k_min, k_max | −20, 20 |
| l_min, l_max | −21, 21 |

| Structural data: | |
|---|---|
| Reflections collected/unique | 35627/7642 [$^a$R(int) = 0.049] |
| Reflections [I > 2σ] | 5925 |
| Completeness to theta_max | 0.99 |
| Absorption correction type | none |
| Refinement method | Full-matrix least-squares on F$^2$ |
| Data/restraints/parameters | 7642/0/352 |
| $^b$Goodness-of-fit | 1.034 |
| Final R indices [I > 2σ] | $^c$R$_1$ = 0.0495, $^d$wR$_2$ = 0.1256 |
| R indices (all data) | $^c$R$_1$ = 0.0719, $^d$wR$_2$ = 0.1411 |
| Largest diff. peak and hole | 0.284 and −0.203 e · Å$^{-3}$ |

Atomic coordinates, site occupancy (%) and equivalent isotropic displacement parameters (Å$^2$×10$^3$).

U(eq) is defined as one third of the trace of the orthogonalized Uij tensor.

Atom numbering of FIG. 2.2.1 corresponds to below table.

| Atom | x | y | z | occ. | U(eq) |
|---|---|---|---|---|---|
| C1 | 0.9387(2) | 0.25439(15) | 0.89639(14) | 1 | 0.0374(5) |
| H1 | 1.0075 | 0.2226 | 0.8823 | 1 | 0.045 |
| C2 | 0.9724(2) | 0.34995(16) | 0.90497(14) | 1 | 0.0390(5) |
| C3 | 1.0805(2) | 0.37308(17) | 0.87926(17) | 1 | 0.0442(5) |
| H3 | 1.1276 | 0.3319 | 0.8546 | 1 | 0.053 |
| C4 | 1.1150(2) | 0.45761(19) | 0.89130(17) | 1 | 0.0494(6) |
| C5 | 1.2096(4) | 0.5829(2) | 0.8960(3) | 1 | 0.0862(12) |
| H5A | 1.2163 | 0.6192 | 0.8463 | 1 | 0.103 |
| H5B | 1.2695 | 0.5986 | 0.9342 | 1 | 0.103 |
| C6 | 1.0469(3) | 0.51945(17) | 0.92762(18) | 1 | 0.0528(6) |
| C7 | 0.9399(2) | 0.49967(18) | 0.95274(17) | 1 | 0.0498(6) |
| H7 | 0.8939 | 0.5421 | 0.9765 | 1 | 0.06 |
| C8 | 0.9026(2) | 0.41337(17) | 0.94127(15) | 1 | 0.0434(5) |
| C9 | 0.7884(2) | 0.38828(18) | 0.97226(17) | 1 | 0.0493(6) |
| H9A | 0.7497 | 0.3553 | 0.9291 | 1 | 0.059 |
| H9B | 0.7455 | 0.4411 | 0.9836 | 1 | 0.059 |
| C10 | 0.7951(3) | 0.33282(2) | 1.05191(18) | 1 | 0.0569(7) |
| H10A | 0.8046 | 0.3714 | 1.0997 | 1 | 0.068 |
| H10B | 0.7251 | 0.3014 | 1.0592 | 1 | 0.068 |
| C11 | 0.8990(3) | 0.2199(3) | 1.12687(17) | 1 | 0.0648(8) |
| H11A | 0.8277 | 0.1965 | 1.1455 | 1 | 0.078 |
| H11B | 0.9302 | 0.256 | 1.1711 | 1 | 0.078 |
| C12 | 0.9767(5) | 0.1482(3) | 1.1039(2) | 1 | 0.1012(16) |
| H12A | 1.0519 | 0.162 | 1.1227 | 1 | 0.121 |
| H12B | 0.9536 | 0.0937 | 1.1303 | 1 | 0.121 |
| C13 | 0.9745(3) | 0.1391(2) | 1.0129(2) | 1 | 0.0677(9) |
| H13A | 0.949 | 0.0808 | 0.9975 | 1 | 0.081 |
| H13B | 1.0488 | 0.148 | 0.99 | 1 | 0.081 |
| C14 | 0.8927(2) | 0.20973(17) | 0.97856(14) | 1 | 0.0426(5) |
| C15 | 0.7844(2) | 0.16871(17) | 0.95088(16) | 1 | 0.0457(5) |
| H15 | 0.7362 | 0.1387 | 0.9865 | 1 | 0.055 |
| C16 | 0.7655(2) | 0.18031(16) | 0.86960(15) | 1 | 0.0407(5) |
| C17 | 0.8541(2) | 0.23162(15) | 0.82622(14) | 1 | 0.0374(5) |
| H17 | 0.8905 | 0.1948 | 0.7839 | 1 | 0.045 |
| C18 | 0.8201(2) | 0.31714(16) | 0.70344(14) | 1 | 0.0415(5) |
| C19 | 0.7614(2) | 0.39953(17) | 0.67082(15) | 1 | 0.0470(6) |
| C20 | 0.7996(3) | 0.48109(18) | 0.71967(18) | 1 | 0.0574(7) |
| H20A | 0.7501 | 0.5295 | 0.7059 | 1 | 0.069 |
| H20B | 0.7916 | 0.4693 | 0.7791 | 1 | 0.069 |
| C21 | 0.9168(4) | 0.5087(2) | 0.7031(2) | 1 | 0.0712(10) |
| C22 | 1.1000(4) | 0.4595(4) | 0.6716(3) | 1 | 0.1074(16) |
| H22A | 1.1041 | 0.4831 | 0.6159 | 1 | 0.161 |
| H22B | 1.1425 | 0.4061 | 0.6745 | 1 | 0.161 |
| H22C | 1.1301 | 0.5014 | 0.7106 | 1 | 0.161 |
| C23 | 0.6346(2) | 0.38782(19) | 0.67748(17) | 1 | 0.0525(6) |
| H23A | 0.6135 | 0.3894 | 0.7361 | 1 | 0.063 |
| H23B | 0.5983 | 0.4369 | 0.6499 | 1 | 0.063 |
| C24 | 0.5914(3) | 0.3023(2) | 0.6389(2) | 1 | 0.0590(7) |
| H24A | 0.6233 | 0.2952 | 0.5834 | 1 | 0.071 |
| H24B | 0.6159 | 0.2531 | 0.6729 | 1 | 0.071 |
| C25 | 0.4642(3) | 0.3012(2) | 0.6326(2) | 1 | 0.0665(8) |
| H25A | 0.4338 | 0.3092 | 0.6884 | 1 | 0.08 |
| H25B | 0.4411 | 0.3513 | 0.5994 | 1 | 0.08 |
| C26 | 0.4115(3) | 0.2193(3) | 0.5950(2) | 1 | 0.0754(10) |
| C27 | 0.2855(4) | 0.2319(4) | 0.5904(4) | 1 | 0.1200(19) |

| Atom | x | y | z | occ. | U(eq) |
|---|---|---|---|---|---|
| H27A | 0.2691 | 0.2858 | 0.5617 | 1 | 0.18 |
| H27B | 0.2553 | 0.2343 | 0.6461 | 1 | 0.18 |

Single Crystal X Ray Diffraction of Homoharringtonine Base (Form B)

See Corresponding FIGS. 2.2.2 and 2.2.3

From a suspension in its mother liquor, a suitable single crystal of size 0.43×0.29×0.18 mm was finally selected and implemented on the diffractometer.

| Structural data | |
|---|---|
| Empirical formula | $C_{31}H_{49}NO_{12}$ |
| Extended formula | $C_{29}H_{39}NO_9$, $2(CH_4O)$, $H_2O$ |
| Formula weight | 627.71 |
| Temperature | 150(2) K |
| Wavelength | 0.71073 Å |
| Crystal system, space group | orthorhombic, P $2_1$ $2_1$ $2_1$ |
| Unit cell dimensions | a = 11.7738(10) Å, α = 90° |
| | b = 14.3907(13) Å, β = 90° |
| | c = 19.1368(15) Å, γ = 90° |
| Volume | 3242.4(5) Å$^3$ |
| Z, Calculated density | 4, 1.286 (g · cm$^{-1}$) |
| Absorption coefficient | 0.098 mm$^{-1}$ |
| F(000) | 1352 |
| Crystal size | 0.43 × 0.29 × 0.18 mm |
| Crystal color | colourless |
| Theta range for data collection | 3.02 to 27.46° |
| h_min, h_max | −15, 13 |
| k_min, k_max | −18, 18 |
| l_min, l_max | −24, 19 |
| Reflections collected/unique | 16236/4103 [$^a$R(int) = 0.0334] |
| Reflections [I > 2σ] | 3764 |
| Completeness to theta_max | 0.99 |
| Absorption correction type | multi-scan |
| Refinement method | Full-matrix least-squares on F$^2$ |
| Data/restraints/parameters | 4103/2/421 |
| $^b$Goodness-of-fit | 1.031 |
| Final R indices [I > 2σ] | $^c$R$_1$ = 0.0346, $^d$wR$_2$ = 0.0871 |
| R indices (all data) | $^c$R$_1$ = 0.039, $^d$wR$_2$ = 0.09 |
| Largest diff. peak and hole | 0.259 and −0.2 e · Å$^{-3}$ |

Atomic coordinates, site occupancy (%) and equivalent isotropic displacement parameters (Å$^2$×10$^3$).

U(eq) is defined as one third of the trace of the orthogonalized Uij tensor.

Atom numbering of FIGS. 2.2.2 and 2.2.3 corresponds to below table.

| Atom | x | y | z | occ. | U(eq) |
|---|---|---|---|---|---|
| C1 | 0.14461(16) | 0.92123(13) | 0.19855(10) | 1 | 0.0185(4) |
| H1 | 0.1645 | 0.9474 | 0.2424 | 1 | 0.022 |
| C2 | 0.13507(16) | 0.96935(13) | 0.14015(10) | 1 | 0.0182(4) |
| C3 | 0.10057(15) | 0.91236(13) | 0.07788(10) | 1 | 0.0162(4) |
| H3 | 0.0245 | 0.9326 | 0.0604 | 1 | 0.019 |
| C4 | 0.09461(15) | 0.81122(13) | 0.10658(10) | 1 | 0.0156(4) |
| H4 | 0.0135 | 0.7915 | 0.1024 | 1 | 0.019 |
| C5 | 0.11993(15) | 0.81891(13) | 0.18697(10) | 1 | 0.0173(4) |
| C6 | 0.01795(18) | 0.78404(16) | 0.22996(10) | 1 | 0.0236(4) |
| H6A | −0.0435 | 0.831 | 0.2309 | 1 | 0.028 |
| H6B | −0.0124 | 0.7254 | 0.2103 | 1 | 0.028 |
| C7 | 0.06647(19) | 0.76830(18) | 0.30351(12) | 1 | 0.0324(5) |
| H7A | 0.0543 | 0.8236 | 0.3334 | 1 | 0.039 |
| H7B | 0.0307 | 0.7137 | 0.326 | 1 | 0.039 |
| C8 | 0.19354(19) | 0.75150(15) | 0.29115(10) | 1 | 0.0250(4) |
| H8A | 0.2394 | 0.8 | 0.3146 | 1 | 0.03 |
| H8B | 0.2164 | 0.69 | 0.3095 | 1 | 0.03 |
| N9 | 0.21006(14) | 0.75555(11) | 0.21387(8) | 1 | 0.0190(3) |
| C10 | 0.32858(17) | 0.78051(14) | 0.19706(11) | 1 | 0.0214(4) |
| H10A | 0.3792 | 0.729 | 0.2115 | 1 | 0.026 |
| H10B | 0.3502 | 0.8363 | 0.2243 | 1 | 0.026 |
| C11 | 0.34668(16) | 0.80017(13) | 0.11940(10) | 1 | 0.0185(4) |
| H11A | 0.3221 | 0.8645 | 0.1092 | 1 | 0.022 |
| H11B | 0.4288 | 0.7958 | 0.1088 | 1 | 0.022 |
| C12 | 0.28274(15) | 0.73420(12) | 0.07195(10) | 1 | 0.0166(4) |
| C13 | 0.16369(16) | 0.74035(12) | 0.06606(9) | 1 | 0.0158(4) |
| C14 | 0.10458(16) | 0.68001(13) | 0.02102(10) | 1 | 0.0185(4) |
| H14 | 0.0244 | 0.6838 | 0.0162 | 1 | 0.022 |
| C15 | 0.16632(17) | 0.61550(13) | −0.01569(11) | 1 | 0.0214(4) |
| C16 | 0.28285(17) | 0.60909(13) | −0.00929(11) | 1 | 0.0215(4) |
| C17 | 0.34324(16) | 0.66697(13) | 0.03421(10) | 1 | 0.0196(4) |
| H17 | 0.4234 | 0.6616 | 0.0385 | 1 | 0.023 |
| C18 | 0.2238(2) | 0.49213(19) | −0.07619(17) | 1 | 0.0473(7) |
| H18A | 0.2304 | 0.4778 | −0.1266 | 1 | 0.057 |
| H18B | 0.2144 | 0.433 | −0.0504 | 1 | 0.057 |
| C19 | 0.19032(19) | 1.11428(14) | 0.18498(12) | 1 | 0.0283(5) |
| H19A | 0.2613 | 1.0871 | 0.2022 | 1 | 0.042 |
| H19B | 0.1334 | 1.1137 | 0.2224 | 1 | 0.042 |
| H19C | 0.2041 | 1.1785 | 0.1701 | 1 | 0.042 |
| C21 | 0.15776(16) | 0.96435(12) | −0.03634(9) | 1 | 0.0155(3) |
| C22 | 0.25991(16) | 0.96278(12) | −0.08591(10) | 1 | 0.0169(4) |
| C23 | 0.29059(16) | 0.86127(13) | −0.10429(10) | 1 | 0.0188(4) |
| H23A | 0.3594 | 0.8612 | −0.134 | 1 | 0.023 |
| H23B | 0.3091 | 0.8276 | −0.0607 | 1 | 0.023 |
| C24 | 0.19701(16) | 0.80987(13) | −0.14192(10) | 1 | 0.0187(4) |
| C25 | 0.1561(2) | 0.68927(17) | −0.22153(14) | 1 | 0.0361(5) |
| H25A | 0.1117 | 0.7289 | −0.2529 | 1 | 0.054 |
| H25B | 0.1053 | 0.6598 | −0.1875 | 1 | 0.054 |
| H25C | 0.195 | 0.6412 | −0.2488 | 1 | 0.054 |
| C31 | 0.36248(16) | 1.00778(13) | −0.04883(10) | 1 | 0.0195(4) |
| H31A | 0.3848 | 0.9679 | −0.009 | 1 | 0.023 |
| H31B | 0.4272 | 1.0094 | −0.0819 | 1 | 0.023 |
| C32 | 0.34172(18) | 1.10662(12) | −0.02159(11) | 1 | 0.0212(4) |
| H32A | 0.3272 | 1.149 | −0.0613 | 1 | 0.025 |
| H32B | 0.2742 | 1.1072 | 0.0092 | 1 | 0.025 |
| C33 | 0.44570(19) | 1.13955(14) | 0.01904(12) | 1 | 0.0273(5) |
| H33A | 0.5137 | 1.1282 | −0.0102 | 1 | 0.033 |
| H33B | 0.453 | 1.1004 | 0.0613 | 1 | 0.033 |
| C34 | 0.44740(19) | 1.24164(14) | 0.04199(11) | 1 | 0.0248(4) |
| C35 | 0.5515(2) | 1.25841(17) | 0.08801(15) | 1 | 0.0416(6) |
| H35A | 0.5496 | 1.2159 | 0.128 | 1 | 0.062 |
| H35B | 0.5509 | 1.3227 | 0.1048 | 1 | 0.062 |
| H35C | 0.6206 | 1.2474 | 0.0607 | 1 | 0.062 |
| C36 | 0.4479(2) | 1.30687(14) | −0.01973(12) | 1 | 0.0311(5) |
| H36A | 0.4469 | 1.3713 | −0.0031 | 1 | 0.047 |
| H36B | 0.3805 | 1.2954 | −0.0486 | 1 | 0.047 |
| H36C | 0.5164 | 1.2963 | −0.0477 | 1 | 0.047 |
| O1 | 0.14964(13) | 1.06111(9) | 0.12688(7) | 1 | 0.0244(3) |
| O2 | 0.12829(13) | 0.55129(11) | −0.06415(9) | 1 | 0.0329(4) |
| O3 | 0.32361(13) | 0.53951(11) | −0.05252(9) | 1 | 0.0328(4) |
| O4 | 0.18522(11) | 0.92032(9) | 0.02297(7) | 1 | 0.0169(3) |
| O5 | 0.06782(11) | 1.00004(10) | −0.04854(7) | 1 | 0.0215(3) |
| O6 | 0.23721(13) | 1.01397(10) | −0.14731(7) | 1 | 0.0221(3) |
| HO6 | 0.170(3) | 1.007(2) | −0.1577(16) | 1 | 0.0 |
| O7 | 0.09736(13) | 0.82269(11) | −0.13360(9) | 1 | 0.0326(4) |
| O8 | 0.23961(13) | 0.74537(10) | −0.18490(8) | 1 | 0.0289(3) |
| O9 | 0.34591(17) | 1.25612(12) | 0.08302(10) | 1 | 0.0403(4) |
| HO9 | 0.346(3) | 1.315(2) | 0.0956(15) | 1 | 0.0 |
| C51 | 0.1062(3) | 0.5267(2) | 0.2091(2) | 1 | 0.0688(11) |
| H51A | 0.105 | 0.4613 | 0.1948 | 1 | 0.103 |
| H51B | 0.0453 | 0.5604 | 0.1851 | 1 | 0.103 |
| H51C | 0.0948 | 0.531 | 0.2597 | 1 | 0.103 |
| O52 | 0.21050(17) | 0.56578(12) | 0.19155(11) | 1 | 0.0451(5) |
| H52 | 0.204(3) | 0.632(3) | 0.1905(18) | 1 | 0.068 |
| O61 | 0.03166(17) | 1.03110(13) | −0.21801(10) | 1 | 0.0431(4) |
| H61 | −0.026(3) | 1.028(3) | −0.1858(18) | 1 | 0.065 |
| C62 | −0.0021(2) | 0.96665(19) | −0.26999(14) | 1 | 0.0428(6) |
| H62A | 0.0298 | 0.9852 | −0.3152 | 1 | 0.064 |
| H62B | −0.0852 | 0.9655 | −0.2731 | 1 | 0.064 |
| H62C | 0.0257 | 0.9046 | −0.2576 | 1 | 0.064 |
| O71 | 0.35707(17) | 1.45528(12) | 0.12174(10) | 1 | 0.0408(4) |
| H71A | 0.410(2) | 1.489(2) | 0.0914(15) | 1 | 0.061 |
| H71B | 0.301(2) | 1.498(2) | 0.1443(16) | 1 | 0.061 |

EXAMPLE 3: PREPARATION AND ANALYSES OF HOMOHARRINGTONINE HYDROGEN (2S)-MALATE (SYNONYMOUS: HOMOHARRINGTONINE (2S)-BIMALATE)

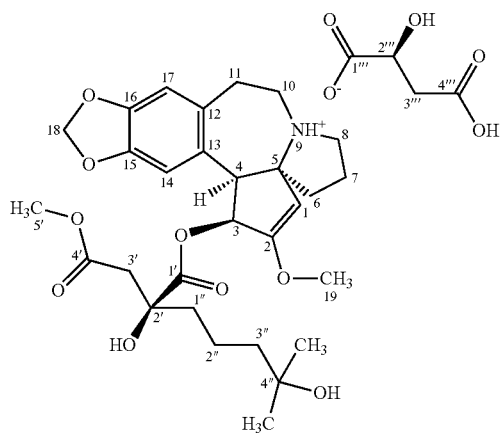

This ionic compound was obtained from commercial homoharringtonine (batch #51H0092) mixed with commercial (2S)-(−)-malic acid (natural form) according to the general procedure in which the solvent was methanol, then isolated as a white prismatic solid mp 205.4-207.7° C. from MeOH (measured by DSC, see FIG. 3.2). Several potentially acceptable crystals were kept suspended in their mother liquors for the subsequent X-ray diffraction analysis. (see below)

$^1$H NMR (400 MHz, Methanol-$d_4$)* δ 6.79 (s, 1H), 6.74 (s, 1H), 6.09 (dd, J=9.6, 0.6 Hz, 1H), 5.96 (d, J=1.1 Hz, 1H), 5.93 (d, J=1.1 Hz, 1H), 5.33 (d, J=0.6 Hz, 1H), 4.24 (dd, J=7.4, 5.4 Hz, 1H), 4.16 (d, J=9.6 Hz, 1H), 3.81 (s, 3H), 3.54 (s, 3H), 3.50 (dd, J=9.5, 4.3 Hz, 1H), 3.42-3.32 (m, 1H), 3.21-3.10 (m, 1H), 2.76 (dd, J=15.9, 5.5 Hz, 1H), 2.71-2.62 (m, 1H), 2.48 (dd, J=15.8, 7.4 Hz, 1H), 2.26-2.05 (m, 4H), 1.94 (d, J=16.1 Hz, 2H), 1.47-1.29 (m, 5H), 1.29-1.17 (m, 1H), 1.15 (s, 6H).

*Partial presuppression of water signal using 'watergate' irradiation $^1$H NMR (600 MHz, Deuterium oxide)* δ 6.84 (s, 1H), 6.76 (s, 1H), 6.01 (dd, J=9.6, 0.7 Hz, 1H), 5.95 (d, J=1.0 Hz, 1H), 5.94 (d, J=1.0 Hz, 1H), 5.34 (d, J=0.6 Hz, 1H), 4.31 (dd, J=8.2, 4.2 Hz, 1H), 4.19 (d, J=9.6 Hz, 1H), 3.76 (s, 3H), 3.52 (s, 3H), 3.52 (m, 1H), 3.42-3.32 (m, 1H), 3.30-3.23 (m, 1H), 3.22-3.15 (m, 1H), 2.76 (dd, J=16.0, 4.2 Hz, 1H), 2.74-2.68 (m, 1H), 2.57 (dd, J=16.0, 8.2 Hz, 1H), 2.36 (d, J=17.0 Hz, 1H), 2.29-2.08 (m, 2H), 1.99 (d, J=16.9 Hz, 1H), 1.97-1.89 (m, 1H), 1.45-1.37 (m, 2H), 1.36-1.26 (m, 3H), 1.12 (s, 6H), 1.12-1.02 (m, 1H).

*Partial presuppression of water signal using 'watergate' irradiation $^{13}$C NMR APT* (101 MHz, MeOD) δ 179.23, 176.13, 174.23, 171.61, 165.05, 149.76, 148.75, 130.92, 126.86, 114.85, 111.80, 102.86, 96.12, 78.09, 76.08, 74.35, 71.27, 69.35, 59.01, 54.21, 53.27, 52.07, 48.94, 44.76, 44.06, 41.80, 40.88, 40.52, 29.25, 29.23, 29.17, 19.95, 19.09.

$^{13}$C NMR APT* (101 MHz, D$_2$O) δ 178.97, 176.21, 174.23, 171.93, 162.88, 147.83, 146.74, 129.74, 125.22, 113.38, 111.12, 101.62, 95.52, 76.98, 75.25, 73.68, 71.34, 68.50, 58.41, 52.95, 52.24, 51.25, 47.58, 42.71, 42.54, 40.00, 39.18, 38.76, 27.69, 27.58, 27.47, 18.58, 17.68.

*APT=Attached Proton Test

IR (Diamond ATR, solid) cm$^{-1}$ 3404, 2969, 2601, 1981, 1758, 1736, 1712, 1657, 1525, 1505, 1490, 1468, 1435, 1374, 1353, 1265, 1226, 1188, 1148, 1080, 1032, 983, 943, 925, 862, 830, 796, 770, 756, 708, 691, 674, 650, 615, 589, 565, 541, 510, 477. See FIG. 1.2

IR (Diamond ATR, film) cm$^{-1}$ 3422, 2964, 1742, 1656, 1596, 1506, 1490, 1440, 1373, 1266, 1224, 1168, 1084, 1033, 929, 710, 615, 566, 509, 477, 0, 983, 943, 925, 862, 830, 796, 770, 756, 708, 691, 674, 650, 615, 589, 565, 541, 510. See FIG. 1.2

Solubility in neutral water: higher than 60 mg/mL

A. Single Crystal X-Ray Diffraction (See FIGS. 2.3.1 and 2.3.2)

From a suspension in its mother liquor, a suitable single crystal of size 0.58×0.46×0.29 mm was finally selected and implemented on the diffractometer.

| Structural data | |
|---|---|
| Empirical formula | $C_{33}H_{45}NO_{14}$ |
| Extended formula | $C_{29}H_{40}NO_9, C_4H_5O_5$ |
| Formula weight | 679.7 |
| Temperature | 150(2) K |
| Wavelength | 0.71073 Å |
| Crystal system, space group | orthorhombic, P 2$_1$ 2$_1$ 2$_1$ |
| Unit cell dimensions | a = 11.488(2) Å, α = 90° |
| | b = 15.399(3) Å, β = 90° |
| | c = 18.825(4) Å, γ = 90° |
| Volume | 3330.2(11) Å$^3$ |
| Z, Calculated density | 4, 1.356 (g · cm$^{-1}$) |
| Absorption coefficient | 0.106 mm$^{-1}$ |
| F(000) | 1448 |
| Crystal size | 0.58 × 0.46 × 0.29 mm |
| Crystal color | white |
| Theta range for data collection | 3.09 to 27.48° |
| h_min, h_max | −14, 14 |
| k_min, k_max | −19, 13 |
| l_min, l_max | −18, 24 |
| Reflections collected/unique | 28567/4233 [$^a$R(int) = 0.1176] |
| Reflections [I > 2σ] | 2414 |
| Completeness to theta_max | 0.998 |
| Absorption correction type | multi-scan |
| Max. and min. transmission | 0.970, 0.688 |
| Refinement method: | Full-matrix least-squares on F$^2$ |
| Data/restraints/parameters | 4233/0/440 |
| $^b$Goodness-of-fit | 1.038 |
| Final R indices [I > 2σ]: | $^c$R$_1$ = 0.0735, $^d$wR$_2$ = 0.1727 |
| R indices (all data): | $^c$R$_1$ = 0.1366, $^d$wR$_2$ = 0.2124 |
| Largest diff. peak and hole | 0.555 and −0.27 e · Å$^{-3}$ |

Atomic coordinates, site occupancy (%) and equivalent isotropic displacement parameters (Å$^2$×10$^3$).

U(eq) is defined as one third of the trace of the orthogonalized Uij tensor.

Atom numbering of FIG. 2.3.1 corresponds to below table.

| Atom | x | y | z | occ. | U(eq) |
|---|---|---|---|---|---|
| C1 | 0.8902(5) | 0.0603(4) | 0.7067(3) | 1 | 0.0450(15) |
| H1 | 0.8742 | 0.0363 | 0.7521 | 1 | 0.054 |
| C2 | 0.8846(5) | 0.0175(4) | 0.6464(3) | 1 | 0.0405(13) |
| C3 | 0.9163(5) | 0.0678(4) | 0.5821(3) | 1 | 0.0412(14) |
| H3 | 0.9896 | 0.0445 | 0.5606 | 1 | 0.049 |
| C4 | 0.9359(4) | 0.1614(4) | 0.6109(3) | 1 | 0.0355(13) |
| H4 | 1.0189 | 0.1762 | 0.6007 | 1 | 0.043 |
| C5 | 0.9255(5) | 0.1528(4) | 0.6934(3) | 1 | 0.0391(13) |
| C6 | 1.0363(5) | 0.1790(5) | 0.7327(3) | 1 | 0.0501(16) |
| H6A | 1.0975 | 0.1343 | 0.7269 | 1 | 0.06 |
| H6B | 1.0662 | 0.2352 | 0.7148 | 1 | 0.06 |
| C7 | 0.9996(6) | 0.1865(5) | 0.8099(3) | 1 | 0.0584(18) |
| H7A | 1.0501 | 0.2277 | 0.836 | 1 | 0.07 |

| Atom | x | y | z | occ. | U(eq) |
|---|---|---|---|---|---|
| H7B | 1.0023 | 0.1293 | 0.8339 | 1 | 0.07 |
| C8 | 0.8744(6) | 0.2204(5) | 0.8049(3) | 1 | 0.0539(17) |
| H8A | 0.8215 | 0.1843 | 0.834 | 1 | 0.065 |
| H8B | 0.8701 | 0.2812 | 0.8219 | 1 | 0.065 |
| N9 | 0.8411(4) | 0.2153(4) | 0.7276(3) | 1 | 0.0432(12) |
| H9 | 0.8561 | 0.2696 | 0.7081 | 1 | 0.052 |
| C10 | 0.7137(5) | 0.1984(5) | 0.7172(3) | 1 | 0.0496(16) |
| H10A | 0.6691 | 0.2495 | 0.7338 | 1 | 0.06 |
| H10B | 0.6904 | 0.148 | 0.7467 | 1 | 0.06 |
| C11 | 0.6826(4) | 0.1802(4) | 0.6402(3) | 1 | 0.0436(14) |
| H11A | 0.7034 | 0.1193 | 0.6287 | 1 | 0.052 |
| H11B | 0.5974 | 0.1864 | 0.6341 | 1 | 0.052 |
| C12 | 0.7435(4) | 0.2399(4) | 0.5885(3) | 1 | 0.0401(14) |
| C13 | 0.8622(4) | 0.2320(4) | 0.5758(3) | 1 | 0.0349(13) |
| C14 | 0.9172(4) | 0.2871(4) | 0.5278(3) | 1 | 0.0364(13) |
| H14 | 0.9984 | 0.2823 | 0.5191 | 1 | 0.044 |
| C15 | 0.8516(5) | 0.3487(4) | 0.4933(3) | 1 | 0.0441(15) |
| C16 | 0.7360(5) | 0.3568(4) | 0.5058(4) | 1 | 0.0464(15) |
| C17 | 0.6788(5) | 0.3043(4) | 0.5538(3) | 1 | 0.0437(15) |
| H17 | 0.598 | 0.3115 | 0.563 | 1 | 0.052 |
| C18 | 0.7884(6) | 0.4626(5) | 0.4322(5) | 1 | 0.076(2) |
| H18A | 0.8017 | 0.5203 | 0.4539 | 1 | 0.091 |
| H18B | 0.7749 | 0.4707 | 0.3807 | 1 | 0.091 |
| C19 | 0.8154(7) | −0.1118(5) | 0.6969(4) | 1 | 0.066(2) |
| H19A | 0.8787 | −0.115 | 0.7317 | 1 | 0.099 |
| H19B | 0.7907 | −0.1707 | 0.6841 | 1 | 0.099 |
| H19C | 0.7496 | −0.0802 | 0.7175 | 1 | 0.099 |
| C21 | 0.8355(4) | 0.0154(4) | 0.4745(3) | 1 | 0.0382(13) |
| C22 | 0.7306(5) | 0.0234(4) | 0.4248(3) | 1 | 0.0412(14) |
| C23 | 0.7103(5) | 0.1202(4) | 0.4059(3) | 1 | 0.0379(13) |
| H23A | 0.6413 | 0.1246 | 0.3746 | 1 | 0.046 |
| H23B | 0.6932 | 0.1527 | 0.4501 | 1 | 0.046 |
| C24 | 0.8129(5) | 0.1618(4) | 0.3693(3) | 1 | 0.0409(14) |
| C25 | 0.8695(6) | 0.2717(5) | 0.2887(4) | 1 | 0.069(2) |
| H25A | 0.9088 | 0.31 | 0.3226 | 1 | 0.104 |
| H25B | 0.8353 | 0.3065 | 0.2505 | 1 | 0.104 |
| H25C | 0.9259 | 0.2308 | 0.2686 | 1 | 0.104 |
| C31 | 0.6209(5) | −0.0103(4) | 0.4625(3) | 1 | 0.0450(14) |
| H31A | 0.6041 | 0.028 | 0.5035 | 1 | 0.054 |
| H31B | 0.5544 | −0.006 | 0.4293 | 1 | 0.054 |
| C32 | 0.6293(5) | −0.1031(4) | 0.4889(4) | 1 | 0.0491(16) |
| H32A | 0.6941 | −0.108 | 0.5233 | 1 | 0.059 |
| H32B | 0.6462 | −0.1422 | 0.4484 | 1 | 0.059 |
| C33 | 0.5166(6) | −0.1309(5) | 0.5242(4) | 1 | 0.0596(19) |
| H33A | 0.4518 | −0.1174 | 0.4914 | 1 | 0.072 |
| H33B | 0.5056 | −0.0947 | 0.5672 | 1 | 0.072 |
| C34 | 0.5053(7) | −0.2260(5) | 0.5462(4) | 1 | 0.069(2) |
| C35 | 0.6051(10) | −0.2507(6) | 0.5911(5) | 1 | 0.100(3) |
| H35A | 0.5942 | −0.3101 | 0.6086 | 1 | 0.15 |
| H35B | 0.6107 | −0.2108 | 0.6315 | 1 | 0.15 |
| H35C | 0.6769 | −0.2477 | 0.563 | 1 | 0.15 |
| C36 | 0.3912(10) | −0.2401(7) | 0.5849(6) | 1 | 0.112(4) |
| H36A | 0.3267 | −0.2205 | 0.5549 | 1 | 0.168 |
| H36B | 0.3914 | −0.2069 | 0.6293 | 1 | 0.168 |
| H36C | 0.3818 | −0.302 | 0.5955 | 1 | 0.168 |
| O31 | 0.5016(6) | −0.2752(4) | 0.4798(3) | 1 | 0.104(2) |
| H31 | 0.4952 | −0.3283 | 0.4889 | 1 | 0.156 |
| O1 | 0.8553(4) | −0.0674(3) | 0.6348(2) | 1 | 0.0543(11) |
| O2 | 0.6901(4) | 0.4222(3) | 0.4640(3) | 1 | 0.0625(13) |
| O3 | 0.8872(4) | 0.4087(3) | 0.4432(2) | 1 | 0.0560(13) |
| O21 | 0.8226(3) | 0.0660(2) | 0.53083(19) | 1 | 0.0371(9) |
| O22 | 0.9152(3) | −0.0342(3) | 0.4646(2) | 1 | 0.0507(11) |
| O23 | 0.7478(3) | −0.0256(3) | 0.3627(2) | 1 | 0.0426(10) |
| H23 | 0.8145 | −0.0155 | 0.3464 | 1 | 0.064 |
| O24 | 0.9138(3) | 0.1434(3) | 0.3794(2) | 1 | 0.0522(12) |
| O25 | 0.7785(4) | 0.2240(3) | 0.3248(2) | 1 | 0.0561(12) |
| C51 | 0.8039(5) | 0.4264(5) | 0.7157(4) | 1 | 0.0518(17) |
| C52 | 0.7548(6) | 0.5067(5) | 0.6770(4) | 1 | 0.0531(17) |
| H52 | 0.7672 | 0.5593 | 0.7073 | 1 | 0.064 |
| C53 | 0.6259(6) | 0.4973(5) | 0.6614(4) | 1 | 0.060(2) |
| H53A | 0.606 | 0.5382 | 0.6226 | 1 | 0.072 |
| H53B | 0.6125 | 0.4379 | 0.6431 | 1 | 0.072 |
| C54 | 0.5421(6) | 0.5127(5) | 0.7216(4) | 1 | 0.065(2) |
| O51 | 0.8885(4) | 0.3887(3) | 0.6897(3) | 1 | 0.0557(12) |
| O52 | 0.7540(6) | 0.4053(4) | 0.7716(3) | 1 | 0.095(2) |
| O53 | 0.8147(6) | 0.5173(5) | 0.6130(4) | 1 | 0.100(2) |
| H53 | 0.8805 | 0.4937 | 0.6161 | 1 | 0.15 |
| O54 | 0.5697(6) | 0.4866(5) | 0.7821(3) | 1 | 0.097(2) |
| H54 | 0.5978 | 0.4363 | 0.7791 | 1 | 0.146 |
| O55 | 0.4515(5) | 0.5523(5) | 0.7122(3) | 1 | 0.110(3) |

B. X-Ray Powder Diffraction

The sample is pure and there is a very good match between the experimental pattern and the calculated pattern (for view of diagrams and experimental details, see FIG. 2.3.3)

EXAMPLE 4: PREPARATION AND ANALYSES OF HOMOHARRINGTONINE HYDROGEN (2R)-MALATE (DIASTEREOMER OF EXAMPLE 3)

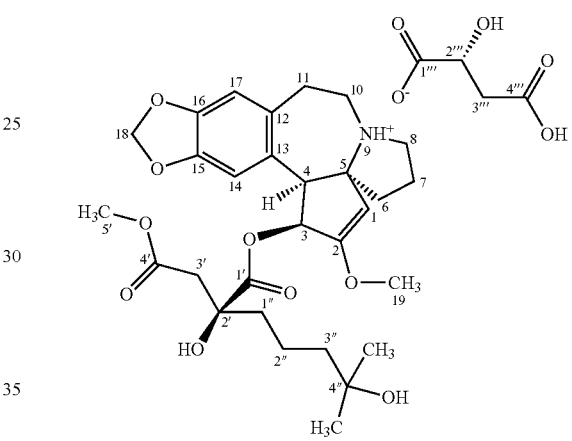

This ionic compound was obtained from commercial homoharringtonine (batch #51H0092) mixed with commercial (2R)-(+)-malic acid (unnatural form) according to the general procedure in which the solvent was methanol, then isolated as a white prismatic solid mp 205-208° C. from MeOH (measured by DSC, see FIG. 3.3). Several potentially acceptable crystals were kept suspended in their mother liquors for the subsequent X-ray diffraction analysis. (see below).

DSC Analysis (See FIG. 3.3)

$^1$H NMR (400 MHz, Methanol-$d_4$)* δ 6.80 (s, 1H), 6.74 (s, 1H), 6.09 (d, J=9.6 Hz, 1H), 5.97 (d, J=1.0 Hz, 1H), 5.93 (d, J=0.9 Hz, 1H), 5.33 (s, 1H), 4.26 (dd, J=7.4, 5.5 Hz, 1H), 4.17 (d, J=9.6 Hz, 1H), 3.81 (s, 3H), 3.55 (s, 3H), 3.53 (s, 1H), 3.34 (s, 2H), 3.22-3.12 (m, 1H), 2.77 (dd, J=15.9, 5.4 Hz, 1H), 2.72-2.64 (m, 1H), 2.49 (dd, J=15.9, 7.4 Hz, 1H), 2.29-2.05 (m, 4H), 1.95 (d, J=16.1 Hz, 2H), 1.48-1.18 (m, 6H), 1.16 (s, 6H).

*Partial presuppression of water signal using 'watergate' irradiation $^{13}$C NMR APT* (101 MHz, Methanol-$d_4$) δ 179.21, 176.06, 174.25, 171.63, 165.07, 149.78, 148.77, 130.94, 126.88, 114.85, 111.80, 102.88, 96.10, 78.07, 76.09, 74.36, 71.28, 69.33, 59.00, 54.22, 53.31, 52.07, 44.77, 44.06, 41.76, 40.88, 40.54, 29.27, 29.22, 19.94, 19.10.

*APT=Attached Proton Test

IR (Diamond ATR, solid) cm$^{-1}$ 3467, 3384, 2970, 2051, 1762, 1737, 1708, 1655, 1607, 1533, 1509, 1494, 1469, 1440, 1376, 1349, 1333, 1292, 1258, 1230, 1208, 1167, 1147, 1121, 1080, 1032, 985, 942, 926, 888, 865, 820, 771, 754, 717, 690, 675, 648, 616, 563, 542, 513, 476. See FIG. 1.3

IR (Diamond ATR, film) cm$^{-1}$ 3422, 2964, 1742, 1656, 1598, 1506, 1490, 1440, 1373, 1266, 1224, 1169, 1084, 1033, 929, 709, 567, 511. See FIG. 1.3

A. Single Crystal X-Ray Diffraction (See FIGS. 2.4.1 and 2.4.2)

From a suspension in its mother liquor, a suitable single crystal of size 0.55×0.48×0.4 mm was finally selected and implemented on the diffractometer.

| Structural data | |
|---|---|
| Empirical formula | $C_{34}H_{49}NO_{15}$ |
| Extended formula | $C_{29}H_{40}NO_9$, $C_4H_5O_5$, $CH_4O$ |
| Formula weight | 711.74 |
| Temperature | 150(2) K |
| Wavelength | 0.71073 Å |
| Crystal system, space group | orthorhombic, $P\,2_1\,2_1\,2_1$ |
| Unit cell dimensions: | |
| a = 11.3958(8) Å, | α = 90° |
| b = 15.5163(16) Å, | β = 90° |
| c = 19.3680(16) Å, | γ = 90° |
| Volume | 3424.7(5) Å$^3$ |
| Z, Calculated density | 4, 1.38 (g · cm$^{-1}$) |
| Absorption coefficient | 0.108 mm$^{-1}$ |
| F(000) | 1520 |
| Crystal size | 0.55 × 0.48 × 0.4 mm |
| Crystal color | colourless |
| Theta range for data collection | 3.06 to 27.47° |
| h_min, h_max | −14, 14 |
| k_min, k_max | −20, 11 |
| l_min, l_max | −25, 14 |
| Reflections collected/unique | 14680/4317 [$^a$R(int) = 0.0515] |
| Reflections [I > 2σ] | 3608 |
| Completeness to theta_max | 0.989 |
| Absorption correction type | multi-scan |
| Max. and min. transmission | 0.958, 0.839 |
| Refinement method: | Full-matrix least-squares on F$^2$ |
| Data/restraints/parameters | 4317/0/474 |
| $^b$Goodness-of-fit | 1.034 |
| Final R indices [I > 2σ]: | $^c$R$_1$ = 0.0397, $^d$wR$_2$ = 0.0825 |
| R indices (all data): | $^c$R$_1$ = 0.0531, $^d$wR$_2$ = 0.0878 |
| Largest diff. peak and hole | 0.26 and −0.27 e · Å$^{-3}$ |

Atomic coordinates, site occupancy (%) and equivalent isotropic displacement parameters (Å$^2$×10$^3$).

U(eq) is defined as one third of the trace of the orthogonalized Uij tensor.

Atom numbering of FIG. 2.4.1 corresponds to below table.

| Atom | x | y | z | occ. | U(eq) |
|---|---|---|---|---|---|
| C1 | 0.8742(2) | 0.06078(16) | 0.19603(12) | 1 | 0.0184(5) |
| H1 | 0.8565 | 0.0356 | 0.2395 | 1 | 0.022 |
| C2 | 0.8762(2) | 0.01795(16) | 0.13644(13) | 1 | 0.0188(5) |
| C3 | 0.9050(2) | 0.07250(16) | 0.07486(11) | 1 | 0.0170(5) |
| H3 | 0.9806 | 0.0529 | 0.0538 | 1 | 0.02 |
| C4 | 0.9198(2) | 0.16514(15) | 0.10526(11) | 1 | 0.0162(5) |
| H4 | 1.0039 | 0.1809 | 0.098 | 1 | 0.019 |
| C5 | 0.9039(2) | 0.15418(16) | 0.18536(12) | 1 | 0.0174(5) |
| C6 | 1.0098(2) | 0.18290(17) | 0.22700(12) | 1 | 0.0235(6) |
| H6A | 1.037 | 0.2405 | 0.2119 | 1 | 0.028 |
| H6B | 1.0752 | 0.1413 | 0.2222 | 1 | 0.028 |
| C7 | 0.9654(3) | 0.18574(18) | 0.30140(13) | 1 | 0.0267(6) |
| H7A | 1.0095 | 0.2288 | 0.3288 | 1 | 0.032 |
| H7B | 0.9732 | 0.1286 | 0.3237 | 1 | 0.032 |
| C8 | 0.8361(3) | 0.21154(17) | 0.29473(12) | 1 | 0.0238(6) |
| H8A | 0.7851 | 0.1693 | 0.3186 | 1 | 0.029 |
| H8B | 0.8226 | 0.2692 | 0.3151 | 1 | 0.029 |
| N9 | 0.81061(19) | 0.21246(14) | 0.21739(10) | 1 | 0.0176(4) |
| H9 | 0.825(3) | 0.269(2) | 0.2017(17) | 1 | 0.05 |
| C10 | 0.6851(2) | 0.19196(17) | 0.20232(13) | 1 | 0.0218(6) |
| H10A | 0.635 | 0.2391 | 0.2201 | 1 | 0.026 |
| H10B | 0.6631 | 0.1385 | 0.227 | 1 | 0.026 |
| C11 | 0.6617(2) | 0.18021(15) | 0.12509(12) | 1 | 0.0191(5) |
| H11A | 0.6845 | 0.121 | 0.1116 | 1 | 0.023 |
| H11B | 0.5764 | 0.1864 | 0.1166 | 1 | 0.023 |
| C12 | 0.7267(2) | 0.24357(15) | 0.07984(12) | 1 | 0.0173(5) |
| C13 | 0.8483(2) | 0.23587(15) | 0.07084(11) | 1 | 0.0158(5) |
| C14 | 0.9095(2) | 0.29500(15) | 0.02929(12) | 1 | 0.0183(5) |
| H14 | 0.9918 | 0.2903 | 0.0226 | 1 | 0.022 |
| C15 | 0.8457(2) | 0.35990(16) | −0.00131(12) | 1 | 0.0200(5) |
| C16 | 0.7266(2) | 0.36742(16) | 0.00808(13) | 1 | 0.0208(5) |
| C17 | 0.6642(2) | 0.31099(15) | 0.04811(12) | 1 | 0.0188(5) |
| H17 | 0.582 | 0.3171 | 0.0542 | 1 | 0.023 |
| C18 | 0.7889(2) | 0.4844(2) | −0.04641(17) | 1 | 0.0369(7) |
| H18A | 0.802 | 0.5311 | −0.0125 | 1 | 0.044 |
| H18B | 0.7814 | 0.5104 | −0.0929 | 1 | 0.044 |
| C19 | 0.8404(3) | −0.11951(17) | 0.18391(15) | 1 | 0.0307(6) |
| H19A | 0.912 | −0.1207 | 0.2119 | 1 | 0.046 |
| H19B | 0.8203 | −0.1782 | 0.1695 | 1 | 0.046 |
| H19C | 0.7759 | −0.0954 | 0.2113 | 1 | 0.046 |
| C21 | 0.8370(2) | 0.02556(14) | −0.03526(12) | 1 | 0.0158(5) |
| C22 | 0.7342(2) | 0.02954(15) | −0.08511(12) | 1 | 0.0162(5) |
| C23 | 0.7016(2) | 0.12332(15) | −0.10139(12) | 1 | 0.0187(5) |
| H23A | 0.6336 | 0.1238 | −0.1332 | 1 | 0.022 |
| H23B | 0.6773 | 0.1523 | −0.0582 | 1 | 0.022 |
| C24 | 0.8000(2) | 0.17318(15) | −0.13336(12) | 1 | 0.0184(5) |
| C25 | 0.8506(3) | 0.2801(2) | −0.21480(17) | 1 | 0.0398(8) |
| H25A | 0.8814 | 0.321 | −0.1808 | 1 | 0.06 |
| H25B | 0.8156 | 0.3119 | −0.2534 | 1 | 0.06 |
| H25C | 0.9146 | 0.2438 | −0.232 | 1 | 0.06 |
| C31 | 0.6261(2) | −0.01467(15) | −0.05365(12) | 1 | 0.0180(5) |
| H31A | 0.599 | 0.02 | −0.0139 | 1 | 0.022 |
| H31B | 0.5625 | −0.0146 | −0.0885 | 1 | 0.022 |
| C32 | 0.6456(2) | −0.10722(15) | −0.02934(12) | 1 | 0.0181(5) |
| H32A | 0.7012 | −0.1076 | 0.0099 | 1 | 0.022 |
| H32B | 0.6803 | −0.1416 | −0.0673 | 1 | 0.022 |
| C33 | 0.5293(2) | −0.14767(15) | −0.00701(13) | 1 | 0.0196(5) |
| H33A | 0.4777 | −0.151 | −0.048 | 1 | 0.024 |
| H33B | 0.4913 | −0.1082 | 0.0264 | 1 | 0.024 |
| C34 | 0.5349(2) | −0.23726(16) | 0.02570(12) | 1 | 0.0202(5) |
| C35 | 0.4125(2) | −0.26450(18) | 0.04804(15) | 1 | 0.0280(6) |
| H35A | 0.4172 | −0.3188 | 0.0737 | 1 | 0.042 |
| H35B | 0.363 | −0.2724 | 0.0072 | 1 | 0.042 |
| H35C | 0.3785 | −0.2198 | 0.0777 | 1 | 0.042 |
| C36 | 0.5878(3) | −0.30546(16) | −0.02198(14) | 1 | 0.0261(6) |
| H36A | 0.6674 | −0.2881 | −0.0353 | 1 | 0.039 |
| H36B | 0.5391 | −0.3111 | −0.0634 | 1 | 0.039 |
| H36C | 0.591 | −0.3609 | 0.0022 | 1 | 0.039 |
| O1 | 0.85935(16) | −0.06660(11) | 0.12358(9) | 1 | 0.0246(4) |
| O2 | 0.88492(17) | 0.42476(12) | −0.04504(10) | 1 | 0.0291(5) |
| HO2 | 0.832(3) | −0.035(2) | −0.1469(17) | 1 | 0.05 |
| O3 | 0.68491(16) | 0.43735(12) | −0.02943(10) | 1 | 0.0313(5) |
| O4 | 0.81179(14) | 0.06809(10) | 0.02407(8) | 1 | 0.0175(4) |
| O5 | 0.92726(15) | −0.01197(11) | −0.04651(9) | 1 | 0.0229(4) |
| O6 | 0.76585(17) | −0.01235(11) | −0.14790(8) | 1 | 0.0213(4) |
| O7 | 0.90141(17) | 0.16881(12) | −0.11593(10) | 1 | 0.0289(4) |
| O8 | 0.76172(16) | 0.22615(12) | −0.18254(10) | 1 | 0.0294(5) |
| O9 | 0.60916(17) | −0.22805(12) | 0.08630(9) | 1 | 0.0220(4) |
| HO9 | 0.624(3) | −0.279(2) | 0.1042(17) | 1 | 0.05 |
| C51 | 0.8226(2) | 0.44762(17) | 0.18302(13) | 1 | 0.0236(6) |
| C52 | 0.7112(2) | 0.45571(16) | 0.22623(13) | 1 | 0.0224(6) |
| H52 | 0.721 | 0.5059 | 0.2581 | 1 | 0.027 |
| C53 | 0.6023(2) | 0.47238(16) | 0.18092(13) | 1 | 0.0224(5) |
| H53A | 0.612 | 0.4418 | 0.1364 | 1 | 0.027 |
| H53B | 0.5323 | 0.4483 | 0.2042 | 1 | 0.027 |
| C54 | 0.5820(2) | 0.56740(17) | 0.16673(12) | 1 | 0.0207(5) |
| O51 | 0.84243(18) | 0.51249(12) | 0.14213(10) | 1 | 0.0327(5) |
| O52 | 0.88827(16) | 0.38509(12) | 0.18781(10) | 1 | 0.0289(4) |
| O53 | 0.69947(19) | 0.38065(13) | 0.26660(10) | 1 | 0.0341(5) |
| H53 | 0.628(3) | 0.377(2) | 0.2833(17) | 1 | 0.05 |
| O54 | 0.48847(17) | 0.60192(12) | 0.18067(9) | 1 | 0.0274(4) |
| O55 | 0.67121(17) | 0.60868(11) | 0.14119(9) | 1 | 0.0263(4) |
| H55 | 0.757(3) | 0.559(2) | 0.1382(16) | 1 | 0.05 |
| C61 | 0.4392(3) | 0.46918(18) | 0.34036(15) | 1 | 0.0321(7) |
| H61A | 0.3848 | 0.4648 | 0.3794 | 1 | 0.048 |

-continued

| Atom | x | y | z | occ. | U(eq) |
|---|---|---|---|---|---|
| H61B | 0.3981 | 0.4932 | 0.3003 | 1 | 0.048 |
| H61C | 0.5048 | 0.5069 | 0.3529 | 1 | 0.048 |
| O62 | 0.4827(2) | 0.38596(14) | 0.32369(11) | 1 | 0.0418(6) |
| H62 | 0.457(3) | 0.347(2) | 0.3498(17) | 1 | 0.05 |

B. X-Ray Powder Diffraction

The sample was pure, there is no doubt that this is the correct phase. However there is a gap of certain diffraction lines, which would be associated with a variation of unit cell parameters. There may be a change in the rate of hydration for example, to cause such a phenomenon (for view of diagrams and experimental details, see FIG. 2.4.3).

EXAMPLE 5: PREPARATION AND ANALYSES OF HOMOHARRINGTONINE HYDROGEN (2S,3S)-TARTRATE

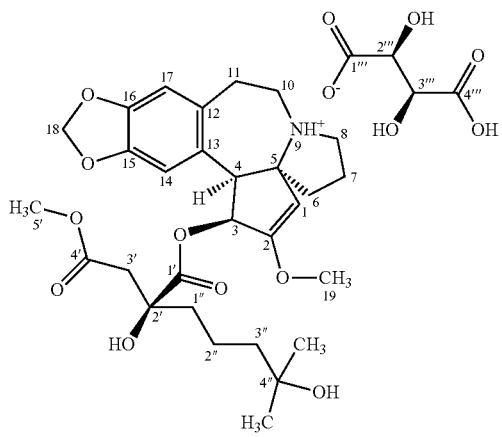

This ionic compound was obtained from commercial homoharringtonine (batch #51H0092) mixed with commercial (2S,3S-(−)-tartaric acid (unnatural form) according to the general procedure, then isolated as a white prismatic solid mp 202-205° C. (uncorrected) from MeOH. (198.1-203.9, measured by DSC, see FIG. 3.4). Several potentially acceptable crystals were kept suspended in their mother liquors for the subsequent X-ray diffraction analysis. (see below).

DSC Analysis (See FIG. 3.4)

$^1$H NMR (400 MHz, Methanol-$d_4$)* δ 6.81 (s, 1H), 6.75 (s, 1H), 6.10 (d, J=9.5 Hz, 1H), 5.97 (d, J=1.1 Hz, 1H), 5.94 (d, J=1.1 Hz, 1H), 5.34 (s, 1H), 4.36 (s, 2H), 4.18 (d, J=9.6 Hz, 1H), 3.82 (s, 3H), 3.55 (s, 3H), 2.24 (d, J=16.2 Hz, 2H), 1.95 (d, J=16.1 Hz, 1H), 1.16 (s, 6H).

*Partial presuppression of water signal using 'watergate' irradiation $^{13}$C NMR APT* (101 MHz, Methanol-d4) δ 176.81, 174.28, 171.67, 165.24, 149.87, 148.85, 130.83, 126.76, 114.91, 111.89, 102.93, 96.04, 78.34, 76.13, 74.38, 74.10, 71.32, 59.10, 54.28, 53.22, 52.12, 44.80, 44.09, 40.91, 40.46, 29.20, 29.19, 19.95, 19.13.

*APT=Attached Proton Test

IR (Diamond ATR, solid) cm$^{-1}$ 3502, 3048, 2971, 2884, 2051, 1981, 1765, 1736, 1656, 1592, 1506, 1490, 1432, 1375, 1348, 1321, 1295, 1265, 1227, 1205, 1165, 1147, 1111, 1081, 1031, 984, 939, 921, 887, 866, 831, 810, 727, 691, 675, 615, 564, 510, 477. See FIG. 1.4

IR (Diamond ATR, film) cm$^{-1}$ 3419, 2963, 1741, 1656, 1611, 1506, 1489, 1440, 1373, 1265, 1224, 1168, 1118, 1083, 1035, 983, 928, 674, 614, 512, 477. See FIG. 1.4

X-Ray Crystallographic Studies

A. Single Crystal X-Ray Diffraction (See FIGS. 2.5.1 and 2.5.2)

From a suspension in its mother liquor, a suitable single crystal of size 0.35×0.28×0.19 mm was finally selected and implemented on the diffractometer.

| Structural data | |
|---|---|
| Empirical formula | $_{33}H_{45}NO_{15}$ |
| Extended formula | $C_{33}H_{45}N_1O_{15}$ |
| Formula weight | 695.7 |
| Temperature | 150(2) K |
| Wavelength | 0.71073 Å |
| Crystal system, space group | orthorhombic, P $2_1$ $2_1$ $2_1$ |
| Unit cell dimensions | a = 10.7962(3) Å, α = 90° |
| | b = 16.3649(5) Å, β = 90° |
| | c = 18.6773(5) Å, γ = 90° |
| Volume | 3299.88(16) Å$^3$ |
| Z, Calculated density | 4, 1.4 (g · cm$^{-1}$) |
| Absorption coefficient | 0.111 mm$^{-1}$ |
| F(000) | 1480 |
| Crystal size | 0.35 × 0.28 × 0.19 mm |
| Crystal color | colourless |
| Theta range for data collection | 3.12 to 27.48° |
| h_min, h_max | −14, 14 |
| k_min, k_max | −18, 21 |
| l_min, l_max | −23, 24 |
| Reflections collected/unique | 53493/4200 [$^a$R(int) = 0.0357] |
| Reflections [I > 2σ] | 4022 |
| Completeness to theta_max | 0.997 |
| Absorption correction type | multi-scan |
| Max. and min. transmission | 0.979, 0.921 |
| Refinement method | Full-matrix least-squares on F$^2$ |
| Data/restraints/parameters | 4200/0/464 |
| $^b$Goodness-of-fit | 1.044 |
| Final R indices [I > 2σ]: | $^c$R$_1$ = 0.0289, $^d$wR$_2$ = 0.0766 |
| R indices (all data): | $^c$R$_1$ = 0.0308, $^d$wR$_2$ = 0.0781 |
| Largest diff. peak and hole: | 0.245 and −0.156 e · Å$^{-3}$ |

Atomic coordinates, site occupancy (%) and equivalent isotropic displacement parameters (A$^2$×10$^3$).

U(eq) is defined as one third of the trace of the orthogonalized Uij tensor.

Atom numbering of FIG. 2.5.1 corresponds to below table.

| Atom | x | y | z | occ. | U(eq) |
|---|---|---|---|---|---|
| C1 | 0.60365(16) | 0.56010(10 | 0.77843(9) | 1 | 0.0207(3) |
| H1 | 0.6286 | 0.5375 | 0.7338 | 1 | 0.025 |
| C2 | 0.59199(16) | 0.51759(10) | 0.83901(9) | 1 | 0.0204(3) |
| C3 | 0.54863(14) | 0.56685(9) | 0.90214(8) | 1 | 0.0173(3) |
| H3 | 0.4655 | 0.5475 | 0.9185 | 1 | 0.021 |
| C4 | 0.53958(14) | 0.65545(9) | 0.87170(8) | 1 | 0.0159(3) |
| H4 | 0.4499 | 0.6705 | 0.8739 | 1 | 0.019 |
| C5 | 0.57198(15) | 0.64844(10) | 0.79030(9) | 1 | 0.0176(3) |
| C6 | 0.46897(15) | 0.68171(10) | 0.74191(8) | 1 | 0.0209(3) |
| H6A | 0.4358 | 0.7336 | 0.7612 | 1 | 0.025 |
| H6B | 0.4003 | 0.6418 | 0.738 | 1 | 0.025 |
| C7 | 0.52972(18) | 0.69568(12) | 0.66864(9) | 1 | 0.0279(4) |
| H7A | 0.4941 | 0.7444 | 0.6449 | 1 | 0.034 |
| H7B | 0.5177 | 0.6476 | 0.6372 | 1 | 0.034 |
| C8 | 0.66784(17) | 0.70863(10) | 0.68489(9) | 1 | 0.0232(3) |
| H8A | 0.7186 | 0.6657 | 0.6617 | 1 | 0.028 |
| H8B | 0.6957 | 0.7627 | 0.6674 | 1 | 0.028 |
| N9 | 0.67903(13) | 0.70357(8) | 0.76564(7) | 1 | 0.0175(3) |
| H9 | 0.667(3) | 0.7517(18) | 0.7806(16) | 1 | 0.05 |
| C10 | 0.80715(16) | 0.68107(11) | 0.78842(9) | 1 | 0.0233(3) |
| H10A | 0.8653 | 0.7246 | 0.7736 | 1 | 0.028 |

-continued

| Atom | x | y | z | occ. | U(eq) |
|---|---|---|---|---|---|
| H10B | 0.8321 | 0.6299 | 0.7641 | 1 | 0.028 |
| C11 | 0.81574(15) | 0.66918(10) | 0.86982(9) | 1 | 0.0211(3) |
| H11A | 0.7888 | 0.613 | 0.8818 | 1 | 0.025 |
| H11B | 0.9033 | 0.6749 | 0.8847 | 1 | 0.025 |
| C12 | 0.73790(14) | 0.72935(10) | 0.91171(9) | 1 | 0.0183(3) |
| C13 | 0.60770(14) | 0.72158(9) | 0.91235(8) | 1 | 0.0160(3) |
| C14 | 0.53534(15) | 0.77926(9) | 0.94934(8) | 1 | 0.0177(3) |
| H14 | 0.4476 | 0.7753 | 0.9498 | 1 | 0.021 |
| C15 | 0.59463(16) | 0.84150(10) | 0.98478(9) | 1 | 0.0203(3) |
| C16 | 0.72235(16) | 0.84894(10) | 0.98391(9) | 1 | 0.0228(3) |
| C17 | 0.79564(15) | 0.79481(11) | 0.94736(9) | 1 | 0.0215(3) |
| H17 | 0.8831 | 0.8013 | 0.9461 | 1 | 0.026 |
| C18 | 0.64308(19) | 0.95977(12) | 1.03596(11) | 1 | 0.0325(4) |
| H18A | 0.6364 | 1.0053 | 1.0012 | 1 | 0.039 |
| H18B | 0.6407 | 0.9827 | 1.085 | 1 | 0.039 |
| C19 | 0.6668(2) | 0.39314(9) | 0.79407(10) | 1 | 0.0279(4) |
| H19A | 0.7405 | 0.4221 | 0.7771 | 1 | 0.042 |
| H19B | 0.6068 | 0.3884 | 0.7549 | 1 | 0.042 |
| H19C | 0.6903 | 0.3384 | 0.8106 | 1 | 0.042 |
| C21 | 0.60705(15) | 0.51652(9) | 1.01819(8) | 1 | 0.0167(3) |
| C22 | 0.72136(14) | 0.50930(9) | 1.06633(8) | 1 | 0.0166(3) |
| C23 | 0.77327(15) | 0.59411(9) | 1.08420(9) | 1 | 0.0192(3) |
| H23A | 0.8471 | 0.5876 | 1.1151 | 1 | 0.023 |
| H23B | 0.8004 | 0.6208 | 1.0393 | 1 | 0.023 |
| C24 | 0.68149(16) | 0.64899(10) | 1.12155(9) | 1 | 0.0217(3) |
| C25 | 0.6586(2) | 0.76969(15) | 1.18925(17) | 1 | 0.0533(7) |
| H25A | 0.6067 | 0.7412 | 1.2243 | 1 | 0.08 |
| H25B | 0.6057 | 0.7964 | 1.1536 | 1 | 0.08 |
| H25C | 0.709 | 0.8109 | 1.2137 | 1 | 0.08 |
| C31 | 0.82188(15) | 0.46027(9) | 1.02660(9) | 1 | 0.0191(3) |
| H31A | 0.8479 | 0.4917 | 0.9839 | 1 | 0.023 |
| H31B | 0.8949 | 0.4551 | 1.0583 | 1 | 0.023 |
| C32 | 0.78268(16) | 0.37451(9) | 1.00245(9) | 1 | 0.0197(3) |
| H32A | 0.7604 | 0.3411 | 1.0447 | 1 | 0.024 |
| H32B | 0.709 | 0.3784 | 0.9711 | 1 | 0.024 |
| C33 | 0.88905(17) | 0.33394(10) | 0.96190(10) | 1 | 0.0233(3) |
| H33A | 0.9647 | 0.3386 | 0.9916 | 1 | 0.028 |
| H33B | 0.9038 | 0.3655 | 0.9175 | 1 | 0.028 |
| C34 | 0.87253(17) | 0.24391(10) | 0.94135(9) | 1 | 0.0230(3) |
| C35 | 0.98538(19) | 0.21661(13) | 0.89846(13) | 1 | 0.0370(5) |
| H35A | 0.9902 | 0.2482 | 0.854 | 1 | 0.055 |
| H35B | 0.9779 | 0.1584 | 0.8871 | 1 | 0.055 |
| H35C | 1.0605 | 0.2258 | 0.9268 | 1 | 0.055 |
| C36 | 0.8548(2) | 0.18850(12) | 1.00617(11) | 1 | 0.0385(5) |
| H36A | 0.8438 | 0.132 | 0.9901 | 1 | 0.058 |
| H36B | 0.7814 | 0.2059 | 1.0329 | 1 | 0.058 |
| H36C | 0.9279 | 0.192 | 1.0372 | 1 | 0.058 |
| O1 | 0.61196(13) | 0.43788(7) | 0.85237(7) | 1 | 0.0255(3) |
| O2 | 0.54324(13) | 0.90276(8) | 1.02592(7) | 1 | 0.0284(3) |
| O3 | 0.75632(13) | 0.91539(8) | 1.02482(7) | 1 | 0.0320(3) |
| O4 | 0.63780(10) | 0.56087(7) | 0.95949(6) | 1 | 0.0183(2) |
| O5 | 0.50856(11) | 0.48612(7) | 1.02953(7) | 1 | 0.0244(3) |
| O6 | 0.69079(12) | 0.46715(7) | 1.13040(6) | 1 | 0.0221(2) |
| HO6 | 0.616(3) | 0.4684(17) | 1.1363(15) | 1 | 0.05 |
| O7 | 0.57142(13) | 0.64049(9) | 1.12151(10) | 1 | 0.0408(4) |
| O8 | 0.73882(13) | 0.71156(8) | 1.15402(8) | 1 | 0.0352(3) |
| O9 | 0.76355(13) | 0.23916(8) | 0.89708(8) | 1 | 0.0302(3) |
| HO9 | 0.751(3) | 0.1897(18) | 0.8886(15) | 1 | 0.05 |
| C51 | 0.69752(17) | 1.00450(11) | 0.84160(9) | 1 | 0.0240(3) |
| C52 | 0.75591(16) | 0.92992(10) | 0.80382(9) | 1 | 0.0216(3) |
| H52 | 0.8202 | 0.9054 | 0.8358 | 1 | 0.026 |
| C53 | 0.81501(17) | 0.95062(11) | 0.73116(9) | 1 | 0.0248(3) |
| H53 | 0.7586 | 0.9885 | 0.7048 | 1 | 0.03 |
| C54 | 0.94378(18) | 0.99098(12) | 0.73715(10) | 1 | 0.0291(4) |
| O51 | 0.76283(13) | 1.06995(8) | 0.84564(8) | 1 | 0.0331(3) |
| O52 | 0.59210(13) | 0.99642(8) | 0.86509(8) | 1 | 0.0337(3) |
| O53 | 0.65877(13) | 0.87221(7) | 0.79311(7) | 1 | 0.0276(3) |
| HO53 | 0.604(3) | 0.8924(17) | 0.8176(15) | 1 | 0.05 |
| O54 | 0.82858(17) | 0.87829(10) | 0.69067(9) | 1 | 0.0424(4) |
| HO54 | 0.905(3) | 0.8812(18) | 0.6760(15) | 1 | 0.05 |
| O55 | 1.02589(16) | 0.96663(11) | 0.69804(9) | 1 | 0.0465(4) |
| O56 | 0.95769(14) | 1.05015(9) | 0.78265(9) | 1 | 0.0373(3) |
| HO56 | 0.868(3) | 1.0629(17) | 0.8111(14) | 1 | 0.05 |

B. X-Ray Powder Diffraction

The sample was pure. There was a very good match between the experimental pattern and the calculated pattern (for view of diagrams and experimental details, see FIG. 2.5.3).

EXAMPLE 6: PREPARATION AND ANALYSES OF HOMOHARRINGTONINE HYDROGEN (2R,3R)-TARTRATE (DIASTEREOMER OF EXAMPLE 5)

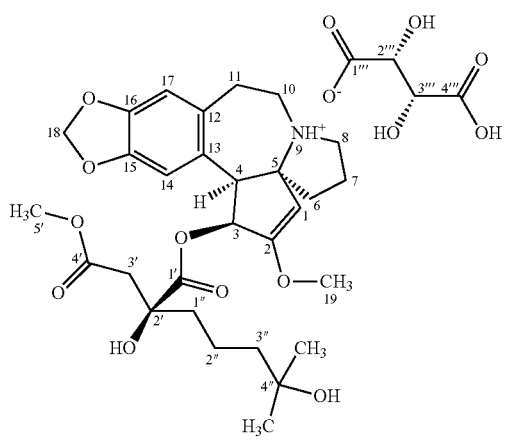

This ionic compound was obtained from commercial homoharringtonine (batch #51H0092) mixed with commercial (+)-(2R,3R)-tartaric acid (batch #) according to the general procedure in which the solvent was methanol, then isolated as a white prismatic solid mp 206-208° C. (uncorrected) from MeOH. (204.6-208.5, measured by DSC, see FIG. 3.5). Several potentially acceptable crystals were kept suspended in their mother liquors for the subsequent X-ray diffraction analysis. (see below).

DSC Analysis (See FIG. 3.5)

$^1$H NMR (400 MHz, Methanol-$d_4$)* δ 6.80 (s, 1H), 6.75 (s, 1H), 6.10 (d, J=9.7 Hz, 1H), 5.97 (d, J=1.0 Hz, 1H), 5.94 (d, J=1.1 Hz, 1H), 5.34 (s, 1H), 4.36 (s, 2H), 4.18 (d, J=9.6 Hz, 1H), 3.82 (s, 3H), 3.55 (s, 3H), 3.44-3.32 (m, 2H), 3.28-3.16 (m, 1H), 2.69 (dd, J=13.7, 5.9 Hz, 1H), 2.27-2.21 (m, 2H), 2.21-1.97 (m, 2H), 1.95 (d, J=16.1 Hz, 1H), 1.49-1.18 (m, 6H), 1.16 (s, 6H).

*Partial presuppression of water signal using 'watergate' irradiation $^{13}$C NMR APT* (101 MHz, Methanol-$d_4$) δ 176.80, 174.24, 171.62, 165.20, 149.84, 148.83, 130.81, 126.73, 114.86, 111.85, 102.89, 96.00, 78.29, 76.09, 74.34, 74.07, 71.28, 59.05, 54.22, 53.18, 52.07, 44.76, 44.05, 40.87, 40.43, 29.23, 29.17, 29.15, 19.91, 19.10.

*APT=Attached Proton Test

IR (Diamond ATR, solid) cm$^{-1}$ 3491, 3044, 2969, 1762, 1737, 1654, 1587, 1506, 1489, 1464, 1431, 1375, 1320, 1295, 1259, 1229, 1210, 1172, 1149, 1107, 1082, 1028, 984, 940, 924, 866, 819, 804, 735, 690, 616, 565, 512, 476. See FIG. 1.5

IR (Diamond ATR, film) cm$^{-1}$ 3417, 2963, 1741, 1655, 1611, 1505, 1489, 1440, 1373, 1265, 1223, 1167, 1118, 1082, 1034, 983, 928, 769, 675, 614, 565, 510, 478, 0, 1031, 984, 939, 921, 887, 866, 831, 810, 727, 691, 675, 615, 564, 510. See FIG. 1.5

X-Ray Crystallographic Studies

A. Single Crystal X-Ray Diffraction (See FIGS. 2.6.1 and 2.6.2)

From a suspension in its mother liquor, a suitable single crystal of size 0.54×0.41×0.34 mm was finally selected and implemented on the diffractometer.

| Structural data | |
|---|---|
| Empirical formula | $C_{33}H_{45}NO_{15}$ |
| Extended formula | $C_{29}H_{40}NO_9$, $C_4H_5O_6$ |
| Formula weight | 695.7 |
| Temperature | 150(2) K |
| Wavelength | 0.71073 Å |
| Crystal system, space group | orthorhombic, $P\,2_1\,2_1\,2_1$ |
| Unit cell dimensions: | |
| a = 10.6770(3) | Å, α = 90° |
| b = 16.6169(6) | Å, β = 90° |
| c = 18.7442(7) | Å, γ = 90° |
| Volume | 3325.6(2) Å$^3$ |
| Z, Calculated density | 4, 1.39 (g · cm$^{-1}$) |
| Absorption coefficient | 0.110 mm$^{-1}$ |
| F(000) | 1480 |
| Crystal size | 0.54 × 0.41 × 0.34 mm |
| Crystal color | colourless |
| Theta range for data collection | 3.11 to 27.48° |
| h_min, h_max | −13, 10 |
| k_min, k_max | −21, 19 |
| l_min, l_max | −23, 15 |
| Reflections collected/unique | 15282/4165 [$^a$R(int) = 0.0328] |
| Reflections [I > 2σ] | 3523 |
| Completeness to theta_max | 0.979 |
| Absorption correction type | multi-scan |
| Max. and min. transmission | 0.963, 0.891 |
| Refinement method | Full-matrix least-squares on F$^2$ |
| Data/restraints/parameters | 4165/0/458 |
| $^b$Goodness-of-fit | 1.021 |
| Final R indices [I > 2σ]: | $^c$R$_1$ = 0.0368, $^d$wR$_2$ = 0.0759 |
| R indices (all data): | $^c$R$_1$ = 0.0498, $^d$wR$_2$ = 0.0816 |
| Largest diff. peak and hole | 0.23 and −0.195 e · Å$^{-3}$ |

Atomic coordinates, site occupancy (%) and equivalent isotropic displacement parameters (Å$^2$×10$^3$).
U(eq) is defined as one third of the trace of the orthogonalized Uij tensor.

Atom numbering of FIG. 2.6.1 corresponds to below table.

| Atom | x | y | z | occ. | U(eq) |
|---|---|---|---|---|---|
| C1 | 0.8908(2) | 0.06521(13) | 0.73105(13) | 1 | 0.0187(5) |
| H1 | 0.8694 | 0.0434 | 0.7763 | 1 | 0.022 |
| C2 | 0.9037(2) | 0.02207(13) | 0.67131(13) | 1 | 0.0194(5) |
| C3 | 0.9421(2) | 0.06998(13) | 0.60762(12) | 1 | 0.0170(5) |
| H3 | 1.0267 | 0.0525 | 0.5907 | 1 | 0.02 |
| C4 | 0.94749(19) | 0.15799(13) | 0.63555(12) | 1 | 0.0149(5) |
| H4 | 1.0376 | 0.1742 | 0.6331 | 1 | 0.018 |
| C5 | 0.91467(19) | 0.15286(12) | 0.71688(12) | 1 | 0.0164(5) |
| C6 | 1.0130(2) | 0.19306(14) | 0.76376(13) | 1 | 0.0210(5) |
| H6A | 1.0399 | 0.2449 | 0.7427 | 1 | 0.025 |
| H6B | 1.0873 | 0.1579 | 0.7691 | 1 | 0.025 |
| C7 | 0.9504(2) | 0.20687(17) | 0.83590(14) | 1 | 0.0310(6) |
| H7A | 0.9805 | 0.2574 | 0.858 | 1 | 0.037 |
| H7B | 0.9677 | 0.1616 | 0.8688 | 1 | 0.037 |
| C8 | 0.8100(2) | 0.21218(14) | 0.81897(12) | 1 | 0.0218(5) |
| H8A | 0.7635 | 0.1686 | 0.8434 | 1 | 0.026 |
| H8B | 0.7756 | 0.2646 | 0.8345 | 1 | 0.026 |
| N9 | 0.80013(17) | 0.20331(11) | 0.73928(10) | 1 | 0.0167(4) |
| H9 | 0.808(3) | 0.2532(19) | 0.7212(17) | 1 | 0.05 |
| C10 | 0.6742(2) | 0.17363(14) | 0.71581(13) | 1 | 0.0212(5) |
| H10A | 0.609 | 0.2121 | 0.7316 | 1 | 0.025 |
| H10B | 0.6569 | 0.1211 | 0.7386 | 1 | 0.025 |
| C11 | 0.6677(2) | 0.16426(14) | 0.63473(13) | 1 | 0.0200(5) |
| H11A | 0.6969 | 0.1096 | 0.622 | 1 | 0.024 |
| H11B | 0.5792 | 0.1689 | 0.6196 | 1 | 0.024 |
| C12 | 0.7446(2) | 0.22516(13) | 0.59340(13) | 1 | 0.0178(5) |
| C13 | 0.87646(19) | 0.22060(12) | 0.59378(12) | 1 | 0.0142(5) |
| C14 | 0.9478(2) | 0.27752(13) | 0.55633(12) | 1 | 0.0176(5) |
| H14 | 1.0367 | 0.2753 | 0.5567 | 1 | 0.021 |
| C15 | 0.8861(2) | 0.33632(13) | 0.51922(13) | 1 | 0.0188(5) |
| C16 | 0.7568(2) | 0.34102(14) | 0.51918(13) | 1 | 0.0229(5) |
| C17 | 0.6842(2) | 0.28758(13) | 0.55610(13) | 1 | 0.0210(5) |
| H17 | 0.5955 | 0.2924 | 0.5566 | 1 | 0.025 |
| C18 | 0.8325(3) | 0.44907(16) | 0.46298(16) | 1 | 0.0358(7) |
| H18A | 0.8347 | 0.4683 | 0.413 | 1 | 0.043 |
| H18B | 0.8367 | 0.4963 | 0.4951 | 1 | 0.043 |
| C19 | 0.8337(2) | −0.10152(13) | 0.71742(14) | 1 | 0.0278(6) |
| H19A | 0.8918 | −0.1024 | 0.7579 | 1 | 0.042 |
| H19B | 0.8166 | −0.1568 | 0.702 | 1 | 0.042 |
| H19C | 0.7552 | −0.0756 | 0.7319 | 1 | 0.042 |
| C21 | 0.8802(2) | 0.01342(12) | 0.49504(13) | 1 | 0.0172(5) |
| C22 | 0.7657(2) | 0.00350(13) | 0.44714(12) | 1 | 0.0171(5) |
| C23 | 0.7075(2) | 0.08447(12) | 0.42747(13) | 1 | 0.0185(5) |
| H23A | 0.637 | 0.0752 | 0.3942 | 1 | 0.022 |
| H23B | 0.6731 | 0.1097 | 0.4711 | 1 | 0.022 |
| C24 | 0.7990(2) | 0.14152(13) | 0.39345(13) | 1 | 0.0203(5) |
| C25 | 0.8218(2) | 0.26011(16) | 0.32546(17) | 1 | 0.0354(7) |
| H25A | 0.8661 | 0.2903 | 0.3626 | 1 | 0.053 |
| H25B | 0.7713 | 0.2972 | 0.2968 | 1 | 0.053 |
| H25C | 0.8828 | 0.2329 | 0.2947 | 1 | 0.053 |
| C32 | 0.6115(2) | −0.17869(13) | 0.54608(14) | 1 | 0.0218(5) |
| H32A | 0.5368 | −0.179 | 0.5147 | 1 | 0.026 |
| H32B | 0.5885 | −0.1491 | 0.59 | 1 | 0.026 |
| C37 | 0.7146(2) | −0.13192(12) | 0.50853(13) | 1 | 0.0197(5) |
| H37A | 0.7423 | −0.1619 | 0.4657 | 1 | 0.024 |
| H37B | 0.7874 | −0.1262 | 0.5409 | 1 | 0.024 |
| C38 | 0.6679(2) | −0.04831(12) | 0.48638(13) | 1 | 0.0192(5) |
| H38A | 0.6402 | −0.0191 | 0.5296 | 1 | 0.023 |
| H38B | 0.594 | −0.0549 | 0.455 | 1 | 0.023 |
| C42 | 0.6411(2) | −0.26590(13) | 0.56665(13) | 1 | 0.0214(5) |
| C44 | 0.5296(2) | −0.30128(16) | 0.60626(15) | 1 | 0.0310(6) |
| H44A | 0.5486 | −0.3567 | 0.6205 | 1 | 0.047 |
| H44B | 0.456 | −0.301 | 0.575 | 1 | 0.047 |
| H44C | 0.5122 | −0.2689 | 0.6488 | 1 | 0.047 |
| C45 | 0.6740(3) | −0.31800(14) | 0.50279(15) | 1 | 0.0351(7) |
| H45A | 0.7474 | −0.2955 | 0.4785 | 1 | 0.053 |
| H45B | 0.603 | −0.3193 | 0.4697 | 1 | 0.053 |
| H45C | 0.6928 | −0.3728 | 0.5189 | 1 | 0.053 |
| O1 | 0.88885(17) | −0.05711(9) | 0.65947(9) | 1 | 0.0254(4) |
| O2 | 0.93569(16) | 0.39596(10) | 0.47637(9) | 1 | 0.0273(4) |
| O3 | 0.71970(17) | 0.40404(11) | 0.47595(10) | 1 | 0.0334(4) |
| O4 | 0.85067(13) | 0.06035(9) | 0.55137(8) | 1 | 0.0176(3) |
| O5 | 0.97892(14) | −0.01899(9) | 0.48520(9) | 1 | 0.0250(4) |
| O6 | 0.80450(16) | −0.03582(10) | 0.38304(9) | 1 | 0.0231(4) |
| HO6 | 0.878(3) | −0.0464(19) | 0.3873(17) | 1 | 0.05 |
| O7 | 0.91117(15) | 0.13633(11) | 0.39748(11) | 1 | 0.0374(5) |
| O8 | 0.74109(15) | 0.20093(9) | 0.35831(10) | 1 | 0.0275(4) |
| O9 | 0.74711(17) | −0.26262(10) | 0.61420(11) | 1 | 0.0320(5) |
| HO9 | 0.755(3) | −0.307(2) | 0.6285(18) | 1 | 0.05 |
| C51 | 0.5651(2) | 0.49263(15) | 0.76865(15) | 1 | 0.0299(6) |
| C52 | 0.6393(2) | 0.42749(13) | 0.72898(15) | 1 | 0.0237(5) |
| H52 | 0.6068 | 0.4235 | 0.6791 | 1 | 0.028 |
| C53 | 0.7815(2) | 0.44249(13) | 0.72627(14) | 1 | 0.022 |
| H53 | 0.8101 | 0.4609 | 0.7744 | 1 | 0.026 |
| C54 | 0.8215(2) | 0.50558(14) | 0.67017(14) | 1 | 0.0241(5) |
| O51 | 0.5872(2) | 0.56776(10) | 0.75398(12) | 1 | 0.0416(5) |
| HO51 | 0.663(3) | 0.5688(18) | 0.7178(18) | 1 | 0.05 |
| O52 | 0.48857(19) | 0.47183(12) | 0.81317(11) | 1 | 0.0462(6) |
| O53 | 0.61742(18) | 0.35372(10) | 0.76410(12) | 1 | 0.0383(5) |
| HO53 | 0.566(3) | 0.361(2) | 0.7939(18) | 1 | 0.05 |
| O54 | 0.84448(16) | 0.36948(10) | 0.70908(10) | 1 | 0.0275(4) |
| HO54 | 0.887(3) | 0.3812(19) | 0.6718(18) | 1 | 0.05 |
| O55 | 0.90625(17) | 0.48767(11) | 0.62938(10) | 1 | 0.0342(4) |
| O56 | 0.76291(16) | 0.57314(9) | 0.67107(11) | 1 | 0.0323(4) |

A. X-Ray Powder Diffraction

The sample was pure and there was a very good match between the experimental pattern and the calculated pattern (for view of diagrams and experimental details, see FIG. 2.6.3).

EXAMPLE 7: PREPARATION AND ANALYSES OF HOMOHARRINGTONINE HYDROGEN (2‴S)-CITRAMALATE

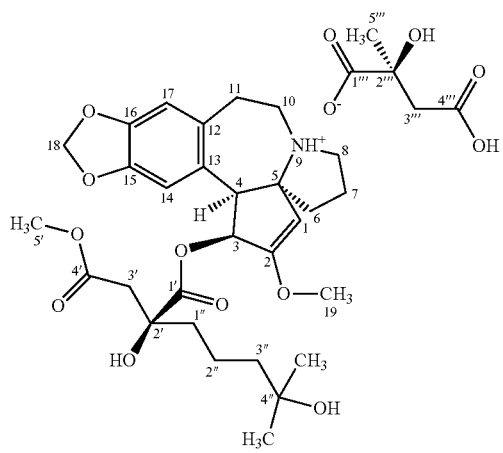

This ionic compound was obtained from commercial homoharringtonine (batch #51H0092) mixed with commercial (2S)-citramalic acid according to the general procedure in which the solvent was methanol, then isolated as a white prismatic solid mp 195.9-198.9° C. (measured by DSC, see FIG. 3.6). Several potentially acceptable crystals were kept suspended in their mother liquors for the subsequent X-ray diffraction analysis. (see below).

DSC Analysis (See FIG. 3.6)

$^1$H NMR (400 MHz, Methanol-$d_4$)* δ 6.80 (s, 1H), 6.74 (s, 1H), 6.09 (d, J=9.6 Hz, 1H), 5.96 (d, J=0.9 Hz, 1H), 5.93 (d, J=0.9 Hz, 1H), 5.33 (s, 1H), 4.17 (d, J=9.6 Hz, 1H), 3.81 (s, 3H), 3.54 (s, 3H), 3.45-3.31 (m, 2H), 3.19 (dd, J=10.6, 6.9 Hz, 1H), 2.70 (d, J=15.7 Hz, 2H), 2.63 (d, J=15.7 Hz, 1H), 2.26-2.12 (m, 4H), 1.94 (d, J=16.1 Hz, 2H), 1.45-1.29 (m, 9H), 1.29-1.17 (m, 1H), 1.15 (s, 6H).

*Partial presuppression of water signal using 'watergate' irradiation $^{13}$C NMR (101 MHz, MeOD) δ 181.21, 176.08, 174.23, 171.62, 165.18, 149.81, 148.79, 130.84, 126.78, 114.87, 114.58, 111.53, 102.58, 95.71, 78.24, 76.08, 74.03, 73.18, 71.27, 58.75, 53.91, 52.90, 51.79, 48.63, 46.32, 44.47, 43.77, 40.59, 40.15, 28.94, 28.89, 28.87, 26.22, 19.62, 18.80.

IR (Diamond ATR, solid) cm$^{-1}$ 2965, 1759, 1739, 1710, 1651, 1506, 1489, 1371, 1341, 1225, 1162, 1079, 1033, 972, 944, 925, 885, 866, 830, 786, 714, 690, 643, 615, 584, 562, 511. See FIG. 1.6

IR (Diamond ATR, film) cm$^{-1}$ 3434, 2968, 1744, 1656, 1590, 1505, 1490, 1374, 1265, 1224, 1166, 1084, 1033, 930, 710, 565. See FIG. 1.6

X-Ray Powder Diffraction

The powder sample is well crystallised, with a peak width of 0.102° (2θ) at 17.597° (2θ) (for view of diagrams and experimental details, see FIG. 2.7.1).

EXAMPLE 8: PREPARATION AND ANALYSES OF HOMOHARRINGTONINE HYDROGEN (2‴R)-CITRAMALATE

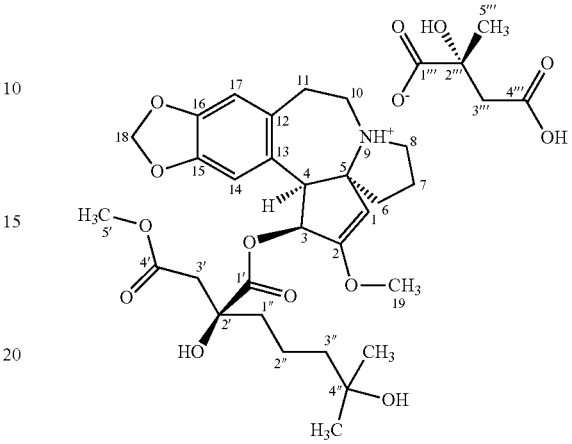

This ionic compound was obtained from commercial homoharringtonine (batch #51H0092) mixed with commercial (2R)-citramalic acid according to the general procedure in which the solvent was methanol, then isolated as a white prismatic solid mp 202.7-204.7° C. (measured by DSC, see FIG. 3.7). Several potentially acceptable crystals were kept suspended in their mother liquors for the subsequent X-ray diffraction analysis. (see below).

DSC Analysis (See FIG. 3.7)

$^1$H NMR (400 MHz, Methanol-$d_4$)* δ 6.79 (s, 1H), 6.74 (s, 1H), 6.08 (d, J=9.6 Hz, 1H), 5.95 (d, J=1.0 Hz, 1H), 5.93 (d, J=1.0 Hz, 1H), 5.33 (s, 1H), 4.17 (d, J=9.6 Hz, 1H), 3.81 (s, 3H), 3.54 (s, 3H), 3.43-3.31 (m, 2H), 3.22-3.14 (m, 1H), 2.73-2.66 (m, 2H), 2.63 (d, J=15.7 Hz, 1H), 2.23 (d, J=16.0 Hz, 2H), 2.19 (s, 1H), 1.94 (d, J=16.1 Hz, 1H), 1.44-1.29 (m, 8H), 1.29-1.17 (m, 1H), 1.15 (s, 6H).

*Partial presuppression of water signal using 'watergate' irradiation $^{13}$C NMR APT* (101 MHz, Methanol-$d_4$) δ 181.21, 176.08, 174.23, 171.62, 165.18, 149.81, 148.79, 130.84, 126.78, 114.87, 111.82, 102.87, 96.00, 78.24, 76.08, 74.33, 73.18, 71.27, 59.04, 54.21, 53.20, 52.07, 48.94, 46.62, 44.76, 44.05, 40.87, 40.45, 29.23, 29.19, 29.17, 26.50, 19.92, 19.09.

*APT=Attached Proton Test

IR (Diamond ATR, solid) cm$^{-1}$ 3681, 3512, 2969, 2845, 1764, 1740, 1707, 1652, 1605, 1513, 1495, 1469, 1440, 1369, 1332, 1292, 1260, 1227, 1204, 1167, 1147, 1124, 1080, 1048, 1033, 1023, 991, 971, 930, 885, 869, 824, 786, 753, 718, 689, 676, 644, 614, 564, 512, 475. See FIG. 1.7

IR (Diamond ATR, film) cm$^{-1}$ 3434, 2968, 2845, 1742, 1655, 1582, 1506, 1490, 1458, 1374, 1265, 1224, 1166, 1084, 1047, 1033, 930, 831, 710, 565, 476. See FIG. 1.7

X-Ray Crystallographic Studies

A. Single Crystal X-Ray Diffraction (See FIGS. 2.8.1 and 2.8.2)

From a suspension in its mother liquor, a suitable single crystal of size 0.44×0.32×0.16 mm was finally selected and implemented on the diffractometer.

| Structural data | |
|---|---|
| Empirical formula | $C_{34}H_{47}NO_{14}$ |
| Extended formula | $C_{29}H_{40}NO_9$, $C_5H_7O_5$ |
| Formula weight | 693.73 |
| Temperature | 150(2) K |
| Wavelength | 0.71073 Å |
| Crystal system, space group | orthorhombic, $P\,2_1\,2_1\,2_1$ |
| Unit cell dimensions | a = 10.3550(3) Å, α = 90° |
| | b = 17.0899(6) Å, β = 90° |
| | c = 19.2854(7) Å, γ = 90° |
| Volume | 3412.9(2) Å$^3$ |
| Z, Calculated density | 4, 1.35 (g · cm$^{-1}$) |
| Absorption coefficient | 0.105 mm$^{-1}$ |
| F(000) | 1480 |
| Crystal size | 0.44 × 0.32 × 0.16 mm |
| Crystal color | colourless |
| Theta range for data collection | 3.09 to 27.48° |
| h_min, h_max | -13, 13 |
| k_min, k_max | -22, 20 |
| l_min, l_max | -19, 25 |
| Reflections collected/unique | 16497/7790 [$^a$R(int) = 0.0336] |
| Reflections [I > 2σ] | 6790 |
| Completeness to theta_max | 0.996 |
| Absorption correction type | multi-scan |
| Max. and min. transmission | 0.983, 0.880 |
| Refinement method | Full-matrix least-squares on F$^2$ |
| Data/restraints/parameters | 7790/0/462 |
| $^b$Goodness-of-fit | 1.026 |
| Final R indices [I > 2σ] | $^c$R$_1$ = 0.0413, $^d$wR$_2$ = 0.0899 |
| R indices (all data) | $^c$R$_1$ = 0.0508, $^d$wR$_2$ = 0.0948 |
| Largest diff. peak and hole | 0.403 and -0.199 e · Å$^{-3}$ |

Atomic coordinates, site occupancy (%) and equivalent isotropic displacement parameters (Å$^2$×10$^3$).
U(eq) is defined as one third of the trace of the orthogonalized Uij tensor.

Atom numbering of FIG. 2.8.1 corresponds to below table.

| Atom | x | y | z | occ. | U(eq) |
|---|---|---|---|---|---|
| C1 | 0.11571(16) | 0.05636(10) | 0.26511(9) | 1 | 0.0175(4) |
| H1 | 0.1363 | 0.0342 | 0.2213 | 1 | 0.021 |
| C2 | 0.09856(16) | 0.01523(10) | 0.32323(9) | 1 | 0.0171(4) |
| C3 | 0.06120(16) | 0.06351(11) | 0.38472(9) | 1 | 0.0162(3) |
| H3 | -0.0279 | 0.0492 | 0.4002 | 1 | 0.019 |
| C4 | 0.06272(15) | 0.14871(10) | 0.35705(9) | 1 | 0.0143(3) |
| H4 | -0.0287 | 0.1675 | 0.3589 | 1 | 0.017 |
| C5 | 0.09821(15) | 0.14231(10) | 0.27823(9) | 1 | 0.0159(4) |
| C6 | 0.00002(16) | 0.18455(11) | 0.23179(9) | 1 | 0.0195(4) |
| H6A | -0.0761 | 0.1508 | 0.2234 | 1 | 0.023 |
| H6B | -0.0293 | 0.2336 | 0.254 | 1 | 0.023 |
| C7 | 0.06914(19) | 0.20226(14) | 0.16369(10) | 1 | 0.0282(5) |
| H7A | 0.0457 | 0.255 | 0.1465 | 1 | 0.034 |
| H7B | 0.046 | 0.1632 | 0.1279 | 1 | 0.034 |
| C8 | 0.21369(17) | 0.19809(11) | 0.18060(9) | 1 | 0.0190(4) |
| H8A | 0.2545 | 0.153 | 0.1569 | 1 | 0.023 |
| H8B | 0.2581 | 0.2467 | 0.166 | 1 | 0.023 |
| N9 | 0.22010(13) | 0.18836(9) | 0.25825(7) | 1 | 0.0156(3) |
| HN9 | 0.215(2) | 0.2413(15) | 0.2762(14) | 1 | 0.05 |
| C10 | 0.34708(16) | 0.15611(11) | 0.28115(9) | 1 | 0.0187(4) |
| H10A | 0.4167 | 0.193 | 0.2681 | 1 | 0.022 |
| H10B | 0.3634 | 0.1059 | 0.2571 | 1 | 0.022 |
| C11 | 0.35010(16) | 0.14274(11) | 0.35966(9) | 1 | 0.0182(4) |
| H11A | 0.313 | 0.0906 | 0.3698 | 1 | 0.022 |
| H11B | 0.4411 | 0.1423 | 0.3753 | 1 | 0.022 |
| C12 | 0.27690(16) | 0.20378(10) | 0.40075(9) | 1 | 0.0161(3) |
| C13 | 0.14095(15) | 0.20673(10) | 0.39833(9) | 1 | 0.0142(3) |
| C14 | 0.07316(17) | 0.26533(10) | 0.43397(9) | 1 | 0.0168(4) |
| H14 | -0.0183 | 0.2688 | 0.4315 | 1 | 0.02 |
| C15 | 0.14387(18) | 0.31747(10) | 0.47263(9) | 1 | 0.0200(4) |
| C16 | 0.27616(18) | 0.31308(11) | 0.47618(9) | 1 | 0.0207(4) |
| C17 | 0.34575(17) | 0.25856(11) | 0.43994(9) | 1 | 0.0190(4) |
| H17 | 0.4374 | 0.258 | 0.4414 | 1 | 0.023 |
| C18 | 0.2137(2) | 0.41952(12) | 0.53342(11) | 1 | 0.0334(5) |
| H18A | 0.2207 | 0.4679 | 0.5055 | 1 | 0.04 |
| H18B | 0.2103 | 0.4343 | 0.583 | 1 | 0.04 |
| C19 | 0.1546(2) | -0.10852(11) | 0.27911(11) | 1 | 0.0300(5) |
| H19A | 0.0911 | -0.1088 | 0.2414 | 1 | 0.045 |
| H19B | 0.1691 | -0.1622 | 0.2952 | 1 | 0.045 |
| H19C | 0.2361 | -0.0864 | 0.2622 | 1 | 0.045 |
| C21 | 0.11247(16) | 0.01321(10) | 0.49827(9) | 1 | 0.0161(3) |
| C22 | 0.22813(16) | 0.00398(10) | 0.54736(9) | 1 | 0.0178(4) |
| C23 | 0.29449(17) | 0.08219(10) | 0.56296(10) | 1 | 0.0189(4) |
| H23A | 0.369 | 0.0729 | 0.594 | 1 | 0.023 |
| H23B | 0.3277 | 0.1048 | 0.5192 | 1 | 0.023 |
| C24 | 0.20436(17) | 0.13941(10) | 0.59644(10) | 1 | 0.0196(4) |
| C25 | 0.18690(19) | 0.25170(12) | 0.66695(12) | 1 | 0.0293(5) |
| H25A | 0.1478 | 0.2853 | 0.6315 | 1 | 0.044 |
| H25B | 0.2392 | 0.2837 | 0.6984 | 1 | 0.044 |
| H25C | 0.1187 | 0.2253 | 0.6933 | 1 | 0.044 |
| C31 | 0.32662(17) | -0.05075(11) | 0.51274(10) | 1 | 0.0204(4) |
| H31A | 0.361 | -0.0244 | 0.4709 | 1 | 0.025 |
| H31B | 0.3997 | -0.0586 | 0.5451 | 1 | 0.025 |
| C32 | 0.27492(18) | -0.13115(11) | 0.49143(10) | 1 | 0.0222(4) |
| H32A | 0.2495 | -0.1609 | 0.5333 | 1 | 0.027 |
| H32B | 0.1973 | -0.1245 | 0.462 | 1 | 0.027 |
| C33 | 0.37715(18) | -0.17662(11) | 0.45161(11) | 1 | 0.0248(4) |
| H33A | 0.4587 | -0.1741 | 0.4783 | 1 | 0.03 |
| H33B | 0.3923 | -0.1495 | 0.407 | 1 | 0.03 |
| C34 | 0.34851(18) | -0.26269(11) | 0.43594(11) | 1 | 0.0240(4) |
| C36 | 0.4577(2) | -0.29453(13) | 0.39087(14) | 1 | 0.0423(6) |
| H36A | 0.4411 | -0.3497 | 0.3801 | 1 | 0.063 |
| H36B | 0.5397 | -0.2899 | 0.4159 | 1 | 0.063 |
| H36C | 0.4623 | -0.2644 | 0.3477 | 1 | 0.063 |
| C35 | 0.3354(2) | -0.31160(13) | 0.50108(12) | 1 | 0.0363(5) |
| H35A | 0.2616 | -0.2929 | 0.5283 | 1 | 0.054 |
| H35B | 0.4144 | -0.3071 | 0.5288 | 1 | 0.054 |
| H35C | 0.3216 | -0.3665 | 0.4884 | 1 | 0.054 |
| O1 | 0.10699(13) | -0.06191(7) | 0.33525(7) | 1 | 0.0244(3) |
| O2 | 0.32223(14) | 0.37011(8) | 0.52078(7) | 1 | 0.0304(3) |
| O3 | 0.09930(13) | 0.37738(8) | 0.51464(7) | 1 | 0.0288(3) |
| O4 | 0.15171(11) | 0.05193(7) | 0.44075(6) | 1 | 0.0171(3) |
| O5 | 0.00628(12) | -0.01257(8) | 0.50746(7) | 1 | 0.0222(3) |
| O6 | 0.18733(13) | -0.03191(8) | 0.60999(7) | 1 | 0.0221(3) |
| HO6 | 0.120(3) | -0.0138(16) | 0.6222(14) | 1 | 0.05 |
| O7 | 0.08889(13) | 0.13801(9) | 0.59158(9) | 1 | 0.0357(4) |
| O8 | 0.26816(12) | 0.19381(8) | 0.63389(7) | 1 | 0.0243(3) |
| O9 | 0.22961(14) | -0.26485(9) | 0.39752(9) | 1 | 0.0348(4) |
| HO9 | 0.203(3) | -0.3138(17) | 0.3982(14) | 1 | 0.05 |
| C51 | 0.17383(18) | 0.50529(11) | 0.36479(10) | 1 | 0.0247(4) |
| C52 | 0.31671(18) | 0.48833(12) | 0.35581(12) | 1 | 0.0299(5) |
| H52A | 0.3411 | 0.4469 | 0.3892 | 1 | 0.036 |
| H52B | 0.3654 | 0.5361 | 0.3686 | 1 | 0.036 |
| C53 | 0.36065(18) | 0.46262(12) | 0.28366(12) | 1 | 0.0288(5) |
| C54 | 0.2995(2) | 0.51004(15) | 0.22598(13) | 1 | 0.0470(6) |
| H54A | 0.3131 | 0.5659 | 0.2348 | 1 | 0.071 |
| H54B | 0.2067 | 0.4991 | 0.2242 | 1 | 0.071 |
| H54C | 0.3392 | 0.4958 | 0.1816 | 1 | 0.071 |
| C55 | 0.33695(18) | 0.37452(11) | 0.26995(10) | 1 | 0.0243(4) |
| O51 | 0.13621(14) | 0.56592(9) | 0.39014(9) | 1 | 0.0361(4) |
| O52 | 0.09277(13) | 0.45011(9) | 0.34618(8) | 1 | 0.0300(3) |
| HO52 | 0.147(2) | 0.4107(15) | 0.3218(14) | 1 | 0.05 |
| O53 | 0.49802(14) | 0.47478(10) | 0.28234(10) | 1 | 0.0438(4) |
| HO53 | 0.530(2) | 0.4274(17) | 0.2667(14) | 1 | 0.05 |
| O54 | 0.42729(14) | 0.33586(9) | 0.24647(8) | 1 | 0.0368(4) |
| O55 | 0.22436(12) | 0.34821(8) | 0.28413(7) | 1 | 0.0261(3) |

A. X-Ray Powder Diffraction

The sample was pure and well crystallised, with a peak width of 0.107° (2θ) at 16.992° (2θ). There was a very good match between the experimental pattern and the calculated pattern (for view of diagrams and experimental details, see FIG. 2.8.3).

EXAMPLE 9: PREPARATION AND ANALYSES OF HOMOHARRINGTONINE HYDROGEN SUCCINATE

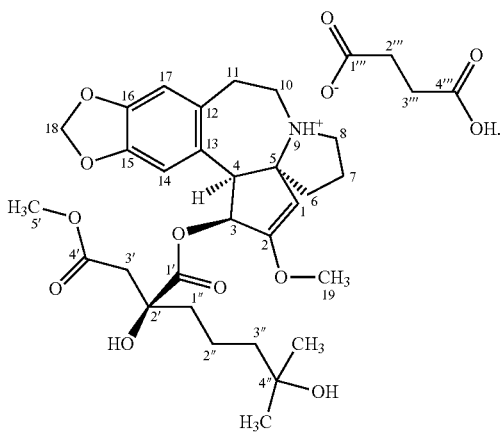

This ionic compound was obtained from commercial homoharringtonine (batch #51H0092) mixed with commercial succinic acid according to the general procedure in which the solvent was methanol, then isolated as a white prismatic solid mp 158.1-160.0° C. (measured by DSC, see FIG. 3.8).

DSC Analysis (See FIG. 3.8)

$^1$H NMR (400 MHz, Methanol-$d_4$)* δ 6.77 (s, 1H), 6.71 (s, 1H), 6.07 (dd, J=9.6, 0.7 Hz, 1H), 5.95 (d, J=1.1 Hz, 1H), 5.92 (d, J=1.1 Hz, 1H), 5.31 (d, J=0.6 Hz, 1H), 4.12 (d, J=9.6 Hz, 1H), 3.79 (s, 3H), 3.54 (s, 3H), 2.49 (s, 4H), 2.22 (d, J=16.2 Hz, 1H), 1.93 (d, J=16.1 Hz, 2H), 1.15 (s, 6H).

*Partial presuppression of water signal using 'watergate' irradiation $^{13}$C NMR APT* (101 MHz, $D_2O$) δ 179.49, 174.22, 171.93, 162.89, 147.84, 146.75, 129.74, 125.23, 113.38, 111.12, 101.62, 95.53, 76.99, 75.26, 73.68, 71.33, 58.41, 52.95, 52.23, 51.27, 48.86, 47.58, 42.72, 42.55, 39.19, 38.77, 31.20, 27.59, 18.59, 17.69.

*APT=Attached Proton Test

IR (KBr, solid), cm$^{-1}$ 3571.1, 3375.3, 3083.4, 2964.4, 1755.4, 1736.7, 1661.8, 1575.5, 1504.8, 1489.7, 1375.0, 1346.3, 1326.1, 1267.2, 1227.1, 1188.3, 1151.7, 1083.4, 1034.7, 929.4, 859.4, 802.8, 758.1, 709.9, 658.9, 617.9, 561.2, 510.6. See FIG. 1.8

EXAMPLE 10: PREPARATION AND ANALYSES OF (3S,4S,5R,2'R)-HOMOHARRINGTONINE HYDROGEN ITACONATE

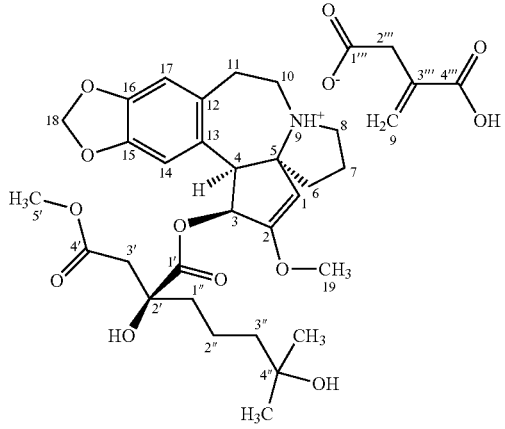

This ionic compound was obtained from commercial homoharringtonine (batch #51H0092) mixed with commercial itaconic acid (batch #) according to the general procedure in which the solvent was methanol, then isolated as a white prismatic solid mp 178.3-181.2° C. (measured by DSC, see FIG. 3.9). Several potentially acceptable crystals were kept suspended in their mother liquors for the subsequent X-ray diffraction analysis. (see below).

DSC Analysis (See FIG. 3.9)

$^1$H NMR (400 MHz, Methanol-$d_4$)* δ 6.78 (s, 1H), 6.72 (s, 1H), 6.08 (d, J=9.6 Hz, 1H), 6.01 (d, J=1.7 Hz, 1H), 5.95 (d, J=1.1 Hz, 1H), 5.92 (d, J=1.1 Hz, 1H), 5.51 (q, J=1.2 Hz, 1H), 5.32 (s, 1H), 4.14 (d, J=9.6 Hz, 1H), 3.80 (s, 3H), 3.54 (s, 3H), 3.51-3.42 (m, 1H), 3.25-3.07 (m, 2H), 2.72-2.60 (m, 1H), 2.26-2.20 (m, 2H), 2.20-2.07 (m, 2H), 1.94 (d, J=16.1 Hz, 2H), 1.47-1.29 (m, 5H), 1.23 (d, J=10.6 Hz, 1H), 1.15 (s, 6H).

*Partial presuppression of water signal using 'watergate' irradiation $^{13}$C NMR (101 MHz, MeOD)** δ 125.11, 114.53, 111.47, 102.52, 96.09, 74.12, 58.66, 53.95, 53.18, 48.70, 44.48, 43.78, 41.66, 40.59, 40.44, 29.12, 28.94, 28.87, 19.70, 18.81.

**DEPT135: Distortionless Enhancement by Polarization Transfer (non-quaternary carbons only)

IR (Diamond ATR, solid) cm$^{-1}$ 3473.2, 2968.4, 2899.8, 2564.7, 1760.7, 1733.5, 1657.6, 1569.7, 1506.4, 1488.9, 1436.1, 1374.9, 1348.9, 1264.2, 1240.7, 1226.2, 1185, 1168.8, 1149.8, 1112.1, 1082.4, 1043.1, 1032.9, 1022.2, 982, 928.1, 890, 866.7, 819.8, 772.1, 722.1, 690.1, 616.7, 543. See FIG. 1.9

IR (ATR, film) cm$^{-1}$ 3458.8, 2967, 1741.5, 1654.8, 1576.7, 1505.2, 1489.3, 1464.3, 1373.4, 1223.8, 1167, 1083.1, 1033.3, 933.6, 563.4. See FIG. 1.9

X-Ray Crystallographic Studies

Single Crystal X-Ray Diffraction (See FIGS. 2.9.1 and 2.9.2)

From a suspension in its mother liquor, a suitable single crystal of size 0.39×0.22×0.1 mm was finally selected and implemented on the diffractometer.

| Structural data | |
|---|---|
| Empirical formula | $C_{34}H_{45}NO_{13}$ |
| Extended formula | $C_{29}H_{40}NO_9$, $C_5H_5O_4$ |
| Formula weight | 675.71 |
| Temperature | 150(2) K |
| Wavelength | 0.71073 Å |
| Crystal system, space group | orthorhombic, $P\,2_1\,2_1\,2_1$ |
| Unit cell dimensions | a = 10.9895(4) Å, α = 90° |
| | b = 16.1963(6) Å, β = 90° |
| | c = 18.7277(5) Å, γ = 90° |
| Volume | 3333.33(19) Å$^3$ |
| Z, Calculated density | 4, 1.346 (g · cm$^{-1}$) |
| Absorption coefficient | 0.103 mm$^{-1}$ |
| F(000) | 1440 |
| Crystal size | 0.39 × 0.22 × 0.1 mm |
| Crystal color | colourless |
| Theta range for data collection | 3.12 to 27.48° |
| h_min, h_max | −11, 14 |
| k_min, k_max | −13, 20 |
| l_min, l_max | −16, 24 |
| Reflections collected/unique | 15962/4207 [$^a$R(int) = 0.0449] |
| Reflections [I > 2σ] | 3444 |
| Completeness to theta_max | 0.986 |
| Absorption correction type | multi-scan |
| Max. and min. transmission | 0.990, 0.844 |
| Refinement method: | Full-matrix least-squares on F$^2$ |
| Data/restraints/parameters | 4207/0/446 |
| $^b$Goodness-of-fit | 1.054 |
| Final R indices [I > 2σ] | $^c$R$_1$ = 0.0411, $^d$wR$_2$ = 0.0914 |
| R indices (all data) | $^c$R$_1$ = 0.0557, $^d$wR$_2$ = 0.0986 |
| Largest diff. peak and hole | 0.312 and −0.249 e · Å$^{-3}$ |

Atomic coordinates, site occupancy (%) and equivalent isotropic displacement parameters ($Å^2 \times 10^3$).
U(eq) is defined as one third of the trace of the orthogonalized Uij tensor.

Atom numbering of FIG. 2.9.1 corresponds to below table.

| Atom | x | y | z | occ. | U(eq) |
|---|---|---|---|---|---|
| C1 | 0.4085(2) | 0.94954(16) | 0.28454(13) | 1 | 0.0246(6) |
| H1 | 0.3897 | 0.972 | 0.239 | 1 | 0.029 |
| C2 | 0.4040(2) | 0.99163(16) | 0.34531(13) | 1 | 0.0239(5) |
| C3 | 0.4399(2) | 0.94237(16) | 0.40941(12) | 1 | 0.0206(5) |
| H3 | 0.5169 | 0.9646 | 0.4305 | 1 | 0.025 |
| C4 | 0.4605(2) | 0.85392(16) | 0.38019(11) | 1 | 0.0187(5) |
| H4 | 0.548 | 0.8406 | 0.3893 | 1 | 0.022 |
| C5 | 0.4471(2) | 0.86236(16) | 0.29702(12) | 1 | 0.0216(5) |
| C6 | 0.5613(2) | 0.83684(18) | 0.25641(12) | 1 | 0.0244(6) |
| H6A | 0.5945 | 0.7845 | 0.2755 | 1 | 0.029 |
| H6B | 0.6247 | 0.8801 | 0.2599 | 1 | 0.029 |
| C7 | 0.5195(2) | 0.8261(2) | 0.17935(13) | 1 | 0.0330(7) |
| H7A | 0.5696 | 0.7843 | 0.1544 | 1 | 0.04 |
| H7B | 0.5244 | 0.879 | 0.153 | 1 | 0.04 |
| C8 | 0.3878(3) | 0.7973(2) | 0.18586(13) | 1 | 0.0347(7) |
| H8A | 0.3332 | 0.8339 | 0.1582 | 1 | 0.042 |
| H8B | 0.3791 | 0.7402 | 0.1675 | 1 | 0.042 |
| N9 | 0.35665(19) | 0.80066(14) | 0.26453(10) | 1 | 0.0225(5) |
| H9 | 0.3728 | 0.749 | 0.284 | 1 | 0.027 |
| C10 | 0.2240(2) | 0.81867(19) | 0.27555(14) | 1 | 0.0293(6) |
| H10A | 0.1752 | 0.7717 | 0.2576 | 1 | 0.035 |
| H10B | 0.2013 | 0.8683 | 0.2477 | 1 | 0.035 |
| C11 | 0.1946(2) | 0.83313(19) | 0.35427(13) | 1 | 0.0280(6) |
| H11A | 0.2153 | 0.8908 | 0.3668 | 1 | 0.034 |
| H11B | 0.1061 | 0.8258 | 0.3617 | 1 | 0.034 |
| C12 | 0.2625(2) | 0.77534(17) | 0.40351(12) | 1 | 0.0218(5) |
| C13 | 0.3876(2) | 0.78580(16) | 0.41518(12) | 1 | 0.0197(5) |
| C14 | 0.4503(2) | 0.73128(16) | 0.45992(12) | 1 | 0.0226(5) |
| H14 | 0.5349 | 0.7378 | 0.4685 | 1 | 0.027 |
| C15 | 0.3868(2) | 0.66846(18) | 0.49096(13) | 1 | 0.0281(6) |
| C16 | 0.2644(2) | 0.65757(18) | 0.47829(14) | 1 | 0.0300(6) |
| C17 | 0.1998(2) | 0.70918(17) | 0.43475(13) | 1 | 0.0274(6) |
| H17 | 0.1156 | 0.7006 | 0.426 | 1 | 0.033 |
| C18 | 0.3315(3) | 0.5504(2) | 0.5409(2) | 1 | 0.0595(10) |
| H18A | 0.3503 | 0.5025 | 0.5101 | 1 | 0.071 |
| H18B | 0.3207 | 0.5305 | 0.5905 | 1 | 0.071 |
| C19 | 0.3222(3) | 1.11383(18) | 0.29761(14) | 1 | 0.0333(7) |
| H19A | 0.2562 | 1.0809 | 0.277 | 1 | 0.05 |
| H19B | 0.3856 | 1.1225 | 0.2616 | 1 | 0.05 |
| H19C | 0.2902 | 1.1674 | 0.3132 | 1 | 0.05 |
| C21 | 0.3633(2) | 0.98532(16) | 0.52334(12) | 1 | 0.0193(5) |
| C22 | 0.2491(2) | 0.98238(16) | 0.56983(12) | 1 | 0.0210(5) |
| C23 | 0.2120(2) | 0.89286(16) | 0.58578(12) | 1 | 0.0225(5) |
| H23A | 0.1406 | 0.8932 | 0.618 | 1 | 0.027 |
| H23B | 0.1873 | 0.8659 | 0.5406 | 1 | 0.027 |
| C24 | 0.3118(2) | 0.84293(17) | 0.61968(12) | 1 | 0.0228(5) |
| C25 | 0.3602(3) | 0.7333(2) | 0.69781(18) | 1 | 0.0448(8) |
| H25A | 0.4231 | 0.7681 | 0.7195 | 1 | 0.067 |
| H25B | 0.3973 | 0.6974 | 0.6618 | 1 | 0.067 |
| H25C | 0.3218 | 0.6994 | 0.7348 | 1 | 0.067 |
| C31 | 0.1446(2) | 1.02575(17) | 0.53105(13) | 1 | 0.0239(5) |
| H31A | 0.1214 | 0.9918 | 0.4892 | 1 | 0.029 |
| H31B | 0.0735 | 1.0275 | 0.5635 | 1 | 0.029 |
| C32 | 0.1704(2) | 1.11351(17) | 0.50526(13) | 1 | 0.0272(6) |
| H32A | 0.1946 | 1.1483 | 0.5463 | 1 | 0.033 |
| H32B | 0.2387 | 1.1127 | 0.4708 | 1 | 0.033 |
| C33 | 0.0585(3) | 1.1503(2) | 0.46982(16) | 1 | 0.0367(7) |
| H33A | -0.0106 | 1.1443 | 0.5033 | 1 | 0.044 |
| H33B | 0.0395 | 1.1164 | 0.4272 | 1 | 0.044 |
| C34 | 0.0638(3) | 1.2404(2) | 0.44632(14) | 1 | 0.0348(7) |
| C35 | -0.0534(3) | 1.2636(3) | 0.4090(2) | 1 | 0.0667(12) |
| H35A | -0.0642 | 1.2289 | 0.3667 | 1 | 0.1 |
| H35B | -0.0499 | 1.3217 | 0.3946 | 1 | 0.1 |
| H35C | -0.122 | 1.2554 | 0.4417 | 1 | 0.1 |
| C36 | 0.0885(3) | 1.2991(2) | 0.50777(16) | 1 | 0.0518(9) |
| H36A | 0.0919 | 1.3558 | 0.4897 | 1 | 0.078 |
| H36B | 0.1664 | 1.2849 | 0.5301 | 1 | 0.078 |
| H36C | 0.0232 | 1.2944 | 0.5432 | 1 | 0.078 |
| O1 | 0.37336(17) | 1.07063(11) | 0.35827(9) | 1 | 0.0295(4) |
| O2 | 0.2228(2) | 0.58991(14) | 0.51681(12) | 1 | 0.0481(6) |
| O3 | 0.4284(2) | 0.60914(13) | 0.53788(11) | 1 | 0.0427(5) |
| O4 | 0.34267(14) | 0.94422(11) | 0.46170(8) | 1 | 0.0201(4) |
| O5 | 0.45495(15) | 1.02085(12) | 0.53858(9) | 1 | 0.0266(4) |
| O6 | 0.27352(16) | 1.02392(12) | 0.63524(9) | 1 | 0.0251(4) |
| HO6 | 0.342(3) | 1.033(2) | 0.6369(17) | 1 | 0.05 |
| O7 | 0.41851(16) | 0.85198(13) | 0.60753(11) | 1 | 0.0356(5) |
| O8 | 0.26888(16) | 0.78534(13) | 0.66423(11) | 1 | 0.0366(5) |
| O9 | 0.1644(2) | 1.24749(16) | 0.39741(12) | 1 | 0.0513(6) |
| HO9 | 0.160(3) | 1.307(2) | 0.3826(17) | 1 | 0.05 |
| C51 | 0.1037(3) | 0.4553(2) | 0.31090(15) | 1 | 0.0388(7) |
| C52 | 0.1159(3) | 0.5480(2) | 0.3010(2) | 1 | 0.0512(9) |
| H52A | 0.0462 | 0.5679 | 0.2723 | 1 | 0.061 |
| H52B | 0.1112 | 0.5749 | 0.3484 | 1 | 0.061 |
| C53 | 0.2325(3) | 0.57416(19) | 0.26485(16) | 1 | 0.0403(8) |
| C54 | 0.3464(3) | 0.57891(18) | 0.30905(13) | 1 | 0.0285(6) |
| C55 | 0.2404(5) | 0.5906(2) | 0.19500(19) | 1 | 0.0747(14) |
| H55A | 0.3166 | 0.6049 | 0.1745 | 1 | 0.09 |
| H55B | 0.1697 | 0.5881 | 0.1659 | 1 | 0.09 |
| O51 | 0.00971(18) | 0.41958(16) | 0.29455(13) | 1 | 0.0529(6) |
| O52 | 0.19701(19) | 0.41745(13) | 0.33812(11) | 1 | 0.0377(5) |
| HO52 | 0.262(3) | 0.454(2) | 0.3511(17) | 1 | 0.05 |
| O53 | 0.41850(17) | 0.63675(12) | 0.30044(10) | 1 | 0.0344(5) |
| O54 | 0.36137(17) | 0.52002(13) | 0.35372(10) | 1 | 0.0346(5) |

EXAMPLE 11: PREPARATION AND ANALYSES OF HOMOHARRINGTONINE HYDROGEN FUMARATE

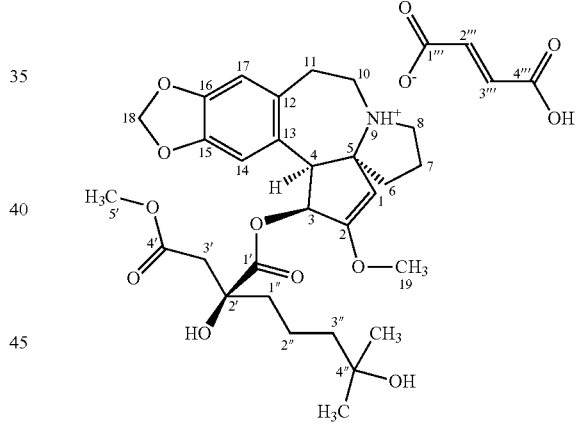

This ionic compound was obtained from commercial homoharringtonine (batch #51H0092) mixed with commercial fumaric acid (batch #) according to the general procedure in which the solvent was methanol, then isolated as a white prismatic solid mp 103.5-107.2° C. (measured by DSC, see FIG. 3.10).

DSC Analysis (See FIG. 3.10)

$^1$H NMR (400 MHz, Methanol-$d_4$)* δ 6.80 (s, 1H), 6.74 (s, 1H), 6.65 (s, 2H), 6.09 (d, J=9.6 Hz, 1H), 5.96 (d, J=0.9 Hz, 1H), 5.93 (d, J=0.9 Hz, 1H), 5.33 (s, 1H), 4.17 (d, J=9.6 Hz, 1H), 3.82 (s, 3H), 3.55 (s, 3H), 3.43-3.32 (m, 2H), 3.24-3.10 (m, 1H), 2.75-2.61 (m, 1H), 2.30-2.08 (m, 4H), 1.95 (d, J=16.1 Hz, 2H), 1.47-1.30 (m, 5H), 1.16 (s, 6H).

*Partial presuppression of water signal using 'watergate" irradiation $^{13}$C NMR (101 MHz, MeOD)** δ 135.91, 114.59, 111.56, 102.57, 95.74, 74.03, 58.74, 53.89, 52.92, 51.79, 49.56, 48.62, 44.47, 43.77, 40.59, 40.16, 28.94, 28.90, 28.88, 19.64, 18.81.

**DEPT135: Distortionless Enhancement by Polarization Transfer (non-quaternary carbons only)

IR (ATR, solid), cm$^{-1}$ 3607.9, 3212.6, 2955.6, 1980.4, 1777.4, 1731.4, 1708.1, 1653.6, 1584.3, 1505.9, 1488.6, 1440.0, 1372.4, 1338.6, 1292.0, 1251.1, 1221.1, 1173.3, 1150.9, 1119.3, 1088.7, 1034.0, 982.0, 934.1, 903.3, 839.6, 790.3, 761.8, 646.0, 613.5, 563.6, 510.2. See FIG. 1.10

X-Ray Powder Diffraction

The powder sample is well crystallised, with a peak width of 0.119° (2θ) at 19.564° (2θ) (for view of diagrams and experimental details, see FIG. 2.7.1).

EXAMPLE 12: PREPARATION AND ANALYSES OF HOMOHARRINGTONINE HYDROGEN TARTRONATE

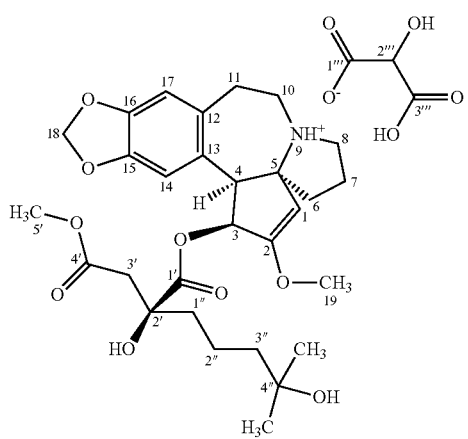

This ionic compound was obtained from commercial homoharringtonine (batch #51H0092) mixed with commercial tartronic acid (batch #) according to the general procedure in which the solvent was methanol, then isolated as a white prismatic solid mp 163.1-167.6° C. (measured by DSC, see FIG. 3.11).

DSC Analysis (See FIG. 3.11)

$^1$H NMR (400 MHz, Methanol-d$_4$)* δ 6.80 (s, 1H), 6.75 (s, 1H), 6.09 (d, J=9.6 Hz, 1H), 5.96 (d, J=0.9 Hz, 1H), 5.94 (d, J=0.9 Hz, 1H), 5.34 (s, 1H), 4.18 (d, J=9.6 Hz, 1H), 3.82 (s, 3H), 3.54 (s, 3H), 2.69 (m, 1H), 2.22 (m, 4H), 2.04-1.91 (m, 2H), 1.47-1.29 (m, 5H), 1.23 (m, 1H), 1.15 (s, 6H).

*Partial presuppression of water signal using 'watergate" irradiation $^{13}$C NMR (101 MHz, MeOD)** δ 114.60, 111.55, 102.61, 95.67, 74.02, 58.77, 53.94, 52.86, 51.79, 48.67, 44.47, 43.77, 40.59, 40.10, 28.94, 28.88, 28.84, 19.63, 18.80.

**DEPT135: Distortionless Enhancement by Polarization Transfer (non-quaternary carbons only)

IR (Diamond ATR, solid) cm$^{-1}$ 3451, 2969, 2898, 2051, 1763, 1730, 1657, 1507, 1490, 1467, 1437, 1376, 1352, 1316, 1294, 1266, 1228, 1208, 1186, 1148, 1126, 1083, 1032, 1002, 985, 943, 927, 891, 866, 802, 753, 720, 690, 675, 652, 614, 563, 510, 477. See FIG. 1.11

IR (Diamond ATR, film) cm$^{-1}$ 3429, 2965, 1744, 1655, 1505, 1489, 1440, 1374, 1266, 1224, 1165, 1084, 1033, 928, 807, 615. See FIG. 1.11

EXAMPLE 13: PREPARATION AND ANALYSES OF HOMOHARRINGTONINE HYDROGEN MALONATE

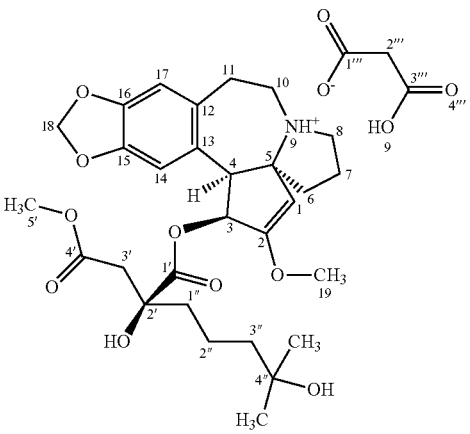

This ionic compound was obtained from commercial homoharringtonine (batch #51H0092) mixed with commercial (2R)-citramalic acid according to the general procedure in which the solvent was methanol-d$_4$, then isolated as a white prismatic solid mp 127.0-131.9° C. (measured by DSC, see FIG. 3.12).

DSC Analysis (See FIG. 3.12)

$^1$H NMR (400 MHz, Methanol-d$_4$)* δ 6.81 (s, 1H), 6.75 (s, 1H), 6.10 (d, J=9.6 Hz, 1H), 5.97 (d, J=1.1 Hz, 1H), 5.94 (d, J=1.0 Hz, 1H), 5.34 (s, 1H), 4.18 (d, J=9.6 Hz, 1H), 3.82 (s, 3H), 3.55 (s, 3H), 3.24-3.17 (m, 1H), 2.74-2.64 (m, 1H), 2.30-2.09 (m, 4H), 1.95 (d, J=16.1 Hz, 2H), 1.48-1.30 (m, 5H), 1.16 (s, 6H).

*Partial presuppression of water signal using 'Watergate' irradiation $^{13}$C NMR APT* (101 MHz, Methanol-d4) δ 174.83, 174.22, 171.62, 165.26, 149.82, 148.81, 130.79, 126.75, 114.88, 111.83, 102.90, 95.90, 78.32, 76.09, 74.30, 71.27, 59.04, 54.21, 53.18, 52.07, 48.94, 44.75, 44.05, 40.87, 40.42, 29.22, 29.17, 29.14, 19.91, 19.09. See FIG. 1.12

*APT=Attached Proton Test

IR (Diamond ATR, solid) cm$^{-1}$ 3453.1, 2967.5, 2933.2, 2899.3, 1765.0, 1735.2, 1654.6, 1505.9, 1489.1, 1463.7, 1439.1, 1374.9, 1349.7, 1292.0, 1266.2, 1226.5, 1207.5, 1148.4, 1083.3, 1060.6, 1032.3, 1002.1, 985.4, 944.1, 925.5, 891.0, 858.5, 830.6, 797.6, 756.7, 721.5, 710.8, 690.8, 615.1, 565.1, 510.8, 498.3, 489.9, 478.9, 472.8. See FIG. 1.12

EXAMPLE 14: PREPARATION AND ANALYSES OF HOMOHARRINGTONINE DIHYDROGEN CITRATE

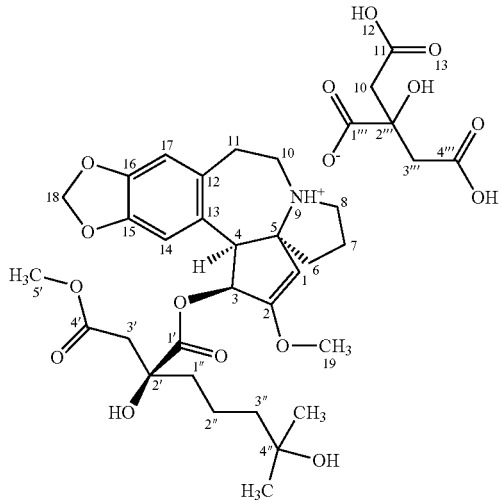

This ionic compound was obtained from commercial homoharringtonine (batch #51H0092) mixed with commercial citric acid (batch #) according to the general procedure in which the solvent was methanol, then isolated as a white prismatic solid mp 170.35-173.9° C. (measured by DSC, see FIG. 3.13). Several potentially acceptable crystals were kept suspended in their mother liquors for the subsequent X-ray diffraction analysis. (see below).

DSC Analysis (See FIG. 3.13)

$^1$H NMR (400 MHz, Methanol-$d_4$)* δ 6.80 (s, 1H), 6.75 (s, 1H), 6.09 (d, J=9.6 Hz, 1H), 5.96 (s, 1H), 5.94 (s, 1H), 5.33 (s, 1H), 4.17 (d, J=9.7 Hz, 1H), 3.81 (s, 3H), 3.54 (s, 3H), 2.79 (d, J=15.4 Hz, 2H), 2.71 (d, J=15.4 Hz, 2+1H), 2.23 (d, J=16.2 Hz, 1H), 1.95 (d, J=16.1 Hz, 1H), 1.49-1.17 (m, 6H), 1.15 (s, 6H).

*Partial presuppression of water signal using 'watergate' irradiation $^{13}$C NMR APT*(101 MHz, Methanol-$d_4$) δ 179.22, 174.90, 174.22, 171.61, 165.22, 149.83, 148.81, 130.80, 126.75, 114.89, 111.84, 102.89, 95.97, 78.30, 76.09, 74.33, 74.01, 71.29, 59.05, 54.23, 53.21, 52.07, 48.95, 44.76, 44.06, 40.88, 40.44, 29.22, 29.18, 29.16, 19.92, 19.10.

*APT=Attached Proton Test

IR (Diamond ATR, solid) cm$^{-1}$ 2959, 1757, 1732, 1715, 1651, 1580, 1508, 1489, 1464, 1432, 1371, 1305, 1262, 1224, 1186, 1151, 1111, 1081, 1032, 985, 944, 922, 909, 864, 829, 806, 705, 690, 614, 581, 563, 510, 486. See FIG. 1.13

IR (Diamond ATR, film) cm$^{-1}$ 3442, 2967, 1738, 1654, 1585, 1505, 1489, 1440, 1373, 1264, 1223, 1115, 1083, 1033, 928. See FIG. 1.13

X-Ray Crystallographic Studies

Single Crystal X-Ray Diffraction (See FIGS. 2.11.1 and 2.11.2)

From a suspension in its mother liquor, a suitable single crystal of size 0.58×0.36×0.28 mm was finally selected and implemented on the diffractometer.

| Structural data | |
|---|---|
| Empirical formula | $C_{36}H_{51}NO_{17}$ |
| Extended formula | $C_{29}H_{40}NO_9$, $C_6H_7O_7$, $CH_4O$ |
| Formula weight | 769.78 |
| Temperature | 150(2) K |
| Wavelength | 0.71073 Å |
| Crystal system, space group | orthorhombic, P $2_1$ $2_1$ $2_1$ |
| Unit cell dimensions | a = 9.9967(3) Å, α = 90° |
| | b = 18.8971(5) Å, β = 90° |
| | c = 19.2826(7) Å, γ = 90° |
| Volume | 3642.6(2) Å$^3$ |
| Z, Calculated density | 4, 1.404 (g · cm$^{-1}$) |
| Absorption coefficient | 0.112 mm$^{-1}$ |
| F(000) | 1640 |
| Crystal size | 0.58 × 0.36 × 0.28 mm |
| Crystal color | colourless |
| Theta range for data collection | 2.94 to 27.48° |
| h_min, h_max | −12, 12 |
| k_min, k_max | −20, 24 |
| l_min, l_max | −25, 13 |
| Reflections collected/unique | 18037/4637 [$^a$R(int) = 0.0424] |
| Reflections [I > 2σ] | 4165 |
| Completeness to theta_max | 0.998 |
| Absorption correction type | multi-scan |
| Max. and min. transmission | 0.969, 0.858 |
| Refinement method | Full-matrix least-squares on F$^2$ |
| Data/restraints/parameters | 4637/0/513 |
| $^b$Goodness-of-fit | 1.032 |
| Final R indices [I > 2σ] | $^c$R$_1$ = 0.0367, $^d$wR$_2$ = 0.0851 |
| R indices (all data) | $^c$R$_1$ = 0.0427, $^d$wR$_2$ = 0.0884 |
| Largest diff. peak and hole | 0.298 and −0.214 e · Å$^{-3}$ |

Atomic coordinates, site occupancy (%) and equivalent isotropic displacement parameters (Å$^2$×10$^3$).
U(eq) is defined as one third of the trace of the orthogonalized Uij tensor.

Atom numbering of FIG. 2.11.1 corresponds to below table.

| Atom | x | y | z | occ. | U(eq) |
|---|---|---|---|---|---|
| C1 | 0.3491(2) | 0.92951(11) | 0.25699(11) | 1 | 0.0149(4) |
| H1 | 0.3259 | 0.9482 | 0.2129 | 1 | 0.018 |
| C2 | 0.3729(2) | 0.96852(11) | 0.31322(11) | 1 | 0.0152(4) |
| C3 | 0.4025(2) | 0.92636(11) | 0.37724(10) | 1 | 0.0138(4) |
| H3 | 0.4934 | 0.9384 | 0.3953 | 1 | 0.017 |
| C4 | 0.3993(2) | 0.84827(11) | 0.35162(11) | 1 | 0.0119(4) |
| H4 | 0.4942 | 0.8317 | 0.3535 | 1 | 0.014 |
| C5 | 0.3638(2) | 0.85222(11) | 0.27257(11) | 1 | 0.0136(4) |
| C6 | 0.4667(2) | 0.81449(12) | 0.22685(11) | 1 | 0.0176(5) |
| H6A | 0.4901 | 0.7677 | 0.2464 | 1 | 0.021 |
| H6B | 0.5492 | 0.8431 | 0.2224 | 1 | 0.021 |
| C7 | 0.3972(3) | 0.80632(13) | 0.15620(12) | 1 | 0.0220(5) |
| H7A | 0.4181 | 0.8469 | 0.1256 | 1 | 0.026 |
| H7B | 0.4258 | 0.7621 | 0.133 | 1 | 0.026 |
| C8 | 0.2475(3) | 0.80407(12) | 0.17319(11) | 1 | 0.0212(5) |
| H8A | 0.2 | 0.8437 | 0.1504 | 1 | 0.025 |
| H8B | 0.2075 | 0.7589 | 0.1575 | 1 | 0.025 |
| N9 | 0.2393(2) | 0.81069(9) | 0.25106(9) | 1 | 0.0141(4) |
| HN9 | 0.251(4) | 0.7629(18) | 0.2669(17) | 1 | 0.05 |
| C10 | 0.1057(2) | 0.83634(12) | 0.27463(11) | 1 | 0.0172(5) |
| H10A | 0.0365 | 0.8014 | 0.2612 | 1 | 0.021 |
| H10B | 0.0848 | 0.8815 | 0.251 | 1 | 0.021 |
| C11 | 0.1006(2) | 0.84755(11) | 0.35335(11) | 1 | 0.0144(4) |
| H11A | 0.1348 | 0.8955 | 0.364 | 1 | 0.017 |
| H11B | 0.0062 | 0.8455 | 0.3686 | 1 | 0.017 |
| C12 | 0.1806(2) | 0.79388(11) | 0.39455(11) | 1 | 0.0130(4) |
| C13 | 0.3209(2) | 0.79563(10) | 0.39455(11) | 1 | 0.0118(4) |
| C14 | 0.3947(2) | 0.74640(11) | 0.43291(11) | 1 | 0.0141(4) |
| H14 | 0.4897 | 0.7472 | 0.433 | 1 | 0.017 |
| C15 | 0.3252(2) | 0.69701(11) | 0.47031(11) | 1 | 0.0153(4) |
| C16 | 0.1875(2) | 0.69386(11) | 0.46951(11) | 1 | 0.0153(4) |
| C17 | 0.1124(2) | 0.74148(11) | 0.43253(11) | 1 | 0.0159(4) |
| H17 | 0.0174 | 0.7392 | 0.4325 | 1 | 0.019 |
| C18 | 0.2626(2) | 0.59964(11) | 0.52687(12) | 1 | 0.0212(5) |
| H18A | 0.2671 | 0.5574 | 0.4966 | 1 | 0.025 |

-continued

| Atom | x | y | z | occ. | U(eq) |
|---|---|---|---|---|---|
| H18B | 0.2624 | 0.5837 | 0.5758 | 1 | 0.025 |
| C19 | 0.3571(3) | 1.07978(12) | 0.25888(13) | 1 | 0.0270(6) |
| H19A | 0.2638 | 1.0737 | 0.2445 | 1 | 0.041 |
| H19B | 0.4165 | 1.0631 | 0.2219 | 1 | 0.041 |
| H19C | 0.3746 | 1.13 | 0.2679 | 1 | 0.041 |
| C21 | 0.3353(2) | 0.98104(10) | 0.48356(11) | 1 | 0.0126(4) |
| C22 | 0.2160(2) | 0.99292(11) | 0.53183(11) | 1 | 0.0140(4) |
| C23 | 0.1479(2) | 0.92348(11) | 0.55222(11) | 1 | 0.0162(4) |
| H23A | 0.0747 | 0.9336 | 0.5854 | 1 | 0.019 |
| H23B | 0.1079 | 0.9015 | 0.5105 | 1 | 0.019 |
| C24 | 0.2446(2) | 0.87236(11) | 0.58470(11) | 1 | 0.0160(4) |
| C25 | 0.2645(3) | 0.77137(12) | 0.65633(13) | 1 | 0.0259(5) |
| H25A | 0.3417 | 0.7932 | 0.6792 | 1 | 0.039 |
| H25B | 0.2957 | 0.7397 | 0.6195 | 1 | 0.039 |
| H25C | 0.2129 | 0.7442 | 0.6904 | 1 | 0.039 |
| C31 | 0.1157(2) | 1.04230(11) | 0.49544(12) | 1 | 0.0172(5) |
| H31A | 0.0748 | 1.0168 | 0.4559 | 1 | 0.021 |
| H31B | 0.0433 | 1.0545 | 0.5284 | 1 | 0.021 |
| C32 | 0.1792(2) | 1.11061(11) | 0.46873(12) | 1 | 0.0195(5) |
| H32A | 0.2259 | 1.1006 | 0.4245 | 1 | 0.023 |
| H32B | 0.247 | 1.1269 | 0.5026 | 1 | 0.023 |
| C33 | 0.0774(2) | 1.16973(11) | 0.45699(13) | 1 | 0.0185(5) |
| 33A | 0.0362 | 1.1819 | 0.5021 | 1 | 0.022 |
| H33B | 0.0055 | 1.1515 | 0.4265 | 1 | 0.022 |
| C34 | 0.1343(2) | 1.23774(11) | 0.42451(12) | 1 | 0.0177(5) |
| C35 | 0.1490(3) | 1.23004(14) | 0.34612(13) | 1 | 0.0286(6) |
| H35A | 0.1813 | 1.2747 | 0.3264 | 1 | 0.043 |
| H35B | 0.062 | 1.2182 | 0.3257 | 1 | 0.043 |
| H35C | 0.2132 | 1.1923 | 0.3358 | 1 | 0.043 |
| C36 | 0.2649(3) | 1.26062(13) | 0.45770(15) | 1 | 0.0279(6) |
| H36A | 0.2555 | 1.26 | 0.5083 | 1 | 0.042 |
| H36B | 0.2874 | 1.3086 | 0.4423 | 1 | 0.042 |
| H36C | 0.3363 | 1.228 | 0.4439 | 1 | 0.042 |
| O1 | 0.38145(18) | 1.03942(8) | 0.32111(8) | 1 | 0.0215(4) |
| O2 | 0.14401(17) | 0.63966(8) | 0.51222(8) | 1 | 0.0216(4) |
| O3 | 0.37524(16) | 0.64530(8) | 0.51409(8) | 1 | 0.0188(3) |
| O4 | 0.30170(15) | 0.93996(7) | 0.42992(8) | 1 | 0.0145(4) |
| O5 | 0.44249(16) | 1.00917(8) | 0.49151(8) | 1 | 0.0177(3) |
| O6 | 0.26234(18) | 1.02640(8) | 0.59345(8) | 1 | 0.0185(3) |
| HO6 | 0.345(4) | 1.0383(18) | 0.5906(18) | 1 | 0.05 |
| O7 | 0.36240(17) | 0.87121(9) | 0.57473(9) | 1 | 0.0269(4) |
| O8 | 0.18077(17) | 0.82599(8) | 0.62673(8) | 1 | 0.0204(4) |
| O9 | 0.03435(17) | 1.29295(8) | 0.43436(9) | 1 | 0.0194(4) |
| HO9 | 0.039(4) | 1.3068(17) | 0.4747(18) | 1 | 0.047 |
| C51 | 0.2081(2) | 0.62031(12) | 0.26814(12) | 1 | 0.0197(5) |
| C52 | 0.2431(2) | 0.55356(11) | 0.31079(11) | 1 | 0.0165(4) |
| C53 | 0.1183(2) | 0.53099(11) | 0.35211(12) | 1 | 0.0196(5) |
| H53A | 0.1 | 0.5667 | 0.3885 | 1 | 0.023 |
| H53B | 0.0402 | 0.5298 | 0.3205 | 1 | 0.023 |
| C54 | 0.1343(2) | 0.45913(12) | 0.38583(12) | 1 | 0.0215(5) |
| O51 | 0.2755(2) | 0.67426(8) | 0.28230(9) | 1 | 0.0293(4) |
| O52 | 0.11948(19) | 0.61575(9) | 0.22240(10) | 1 | 0.0300(4) |
| O53 | 0.34983(17) | 0.57012(9) | 0.35660(9) | 1 | 0.0221(4) |
| HO53 | 0.358(4) | 0.6160(18) | 0.3535(18) | 1 | 0.05 |
| O54 | 0.2279(2) | 0.44156(10) | 0.42120(12) | 1 | 0.0433(6) |
| O55 | 0.03274(18) | 0.41626(9) | 0.37134(8) | 1 | 0.0204(4) |
| HO55 | 0.044(4) | 0.3790(18) | 0.3902(18) | 1 | 0.05 |
| C60 | 0.2959(2) | 0.49411(12) | 0.26327(12) | 1 | 0.0204(4) |
| H60A | 0.3642 | 0.5153 | 0.2324 | 1 | 0.025 |
| H60B | 0.3427 | 0.4594 | 0.2931 | 1 | 0.025 |
| C61 | 0.1992(3) | 0.45307(13) | 0.21778(13) | 1 | 0.0251(5) |
| O62 | 0.0989(2) | 0.48721(10) | 0.18875(10) | 1 | 0.0344(5) |
| HO62 | 0.104(3) | 0.5364(18) | 0.2012(18) | 1 | 0.05 |
| O63 | 0.2167(2) | 0.39075(9) | 0.20666(11) | 1 | 0.0381(5) |
| O71 | 0.5434(2) | 1.13984(10) | 0.43673(10) | 1 | 0.0321(4) |
| HO71 | 0.498(4) | 1.1011(18) | 0.4527(18) | 1 | 0.05 |
| C72 | 0.6645(3) | 1.11097(17) | 0.41010(17) | 1 | 0.0443(8) |
| H72A | 0.6436 | 1.0742 | 0.376 | 1 | 0.066 |
| H72B | 0.7165 | 1.0903 | 0.4481 | 1 | 0.066 |
| H72C | 0.7167 | 1.1485 | 0.3879 | 1 | 0.066 |

X-Ray Powder Diffraction

The powder sample is well crystallised, with a peak width of 0.127° (2θ) at 18.255° (2θ). The powder is constituted in major part by the expected sample referenced HOCIT 5776. However, the powder pattern reveals the presence of a second phase, with significant lines at 7.001° (2θ) and 12.317° (2θ) for example, not calculated from the structure determined with a single crystal (for view of diagrams and experimental details, see FIG. 2.11.3).

EXAMPLE 15: PREPARATION AND ANALYSES OF HOMOHARRINGTONINE SALICYLATE

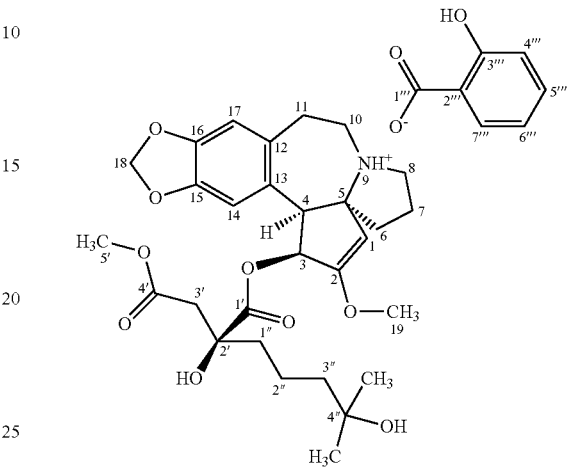

This ionic compound was obtained from commercial homoharringtonine (batch #51H0092) mixed with commercial salicylic acid (batch #) according to the general procedure in which the solvent was methanol, then isolated as a white prismatic solid mp 148.7-151.3° C. (measured by DSC, see FIG. 3.14). Several potentially acceptable crystals were kept suspended in their mother liquors for the subsequent X-ray diffraction analysis. (see below).

DSC Analysis (See FIG. 3.14)

$^1$H NMR (400 MHz, Methanol-$d_4$)* δ 7.80 (dd, J=7.7, 1.7 Hz, 1H), 7.26 (ddd, J=8.8, 7.2, 1.8 Hz, 1H), 6.80-6.70 (m, 4H), 6.09 (d, J=9.6 Hz, 1H), 5.92 (d, J=1.0 Hz, 1H), 5.88 (d, J=1.0 Hz, 1H), 5.33 (s, 1H), 4.17 (d, J=9.6 Hz, 1H), 3.81 (s, 3H), 3.54 (s, 3H), 3.18 (dd, J=11.0, 6.9 Hz, 1H), 2.71-2.62 (m, 1H), 2.28-2.08 (m, 4H), 1.95 (d, J=16.1 Hz, 1H), 1.47-1.30 (m, 5H), 1.30-1.18 (m, 1H), 1.16 (s, 6H).

*Partial presuppression of water signal using 'watergate' irradiation.

$^{13}$C NMR (101 MHz, MeOD)** δ 133.50, 131.36, 118.66, 116.85, 114.49, 111.46, 102.48, 95.80, 74.04, 58.71, 53.86, 52.96, 51.78, 49.56, 48.62, 44.45, 43.75, 40.58, 40.24, 28.96, 28.94, 28.86, 19.65, 18.79.

**DEPT135: Distortionless Enhancement by Polarization Transfer (non-quaternary carbons only)

IR (Diamond ATR, solid) cm$^{-1}$ 2961.4, 2622.5, 1760.5, 1748, 1740.7, 1722.8, 1651.8, 1625.2, 1590.4, 1579.2, 1503.9, 1487.7, 1459.3, 1374, 1334.4, 1293.2, 1224.3, 1167.4, 1082.6, 1043.9, 1030.5, 995.4, 924.5, 890.7, 857.3, 832.8, 805.3, 763.6, 704.8, 666.2, 613.2, 565.6. See FIG. 1.14

IR (Diamond ATR, film) cm$^{-1}$ 3416.8, 2962.9, 2377.4, 2156.9, 1746.7, 1655.2, 1628.2, 1591.3, 1504.8, 1488.2, 1459.5, 1375.8, 1330.2, 1223.6, 1084.2, 1034.5, 930.1, 858.3, 807.3, 763.1, 705.4. See FIG. 1.14

X-Ray Crystallographic Studies

Single Crystal X-Ray Diffraction (See FIGS. 2.12.1 to 2.12.4)

From a suspension in its mother liquor, a small single crystal of size 0.15×0.11×0.04 mm was finally selected and implemented on the diffractometer.

| Structural data | |
|---|---|
| Empirical formula | $C_{72}H_{94}N_2O_{26}$ |
| Extended formula | $2(C_{29}H_{40}NO_9), 2(C_7H_5O_3), 2(H_2O)$ |
| Formula weight | 1403.5 |
| Temperature | 150(2) K |
| Wavelength | 0.71073 Å |
| Crystal system, space group | monoclinic, P $2_1$ |
| Unit cell dimensions | a = 11.6871(3) Å, α = 90° |
| | b = 25.8294(6) Å, β = 114.6320(10)° |
| | c = 12.6300(3) Å, γ = 90° |
| Volume | 3465.69(15) Å$^3$ |
| Z, Calculated density | 2, 1.345 (g · cm$^{-1}$) |
| Absorption coefficient | 0.102 mm$^{-1}$ |
| F(000) | 1496 |
| Crystal size | 0.15 × 0.11 × 0.04 mm |
| Crystal color | colourless |
| Theta range for data collection | 2.96 to 27.48° |
| h_min, h_max | −15, 15 |
| k_min, k_max | −33, 33 |
| l_min, l_max | −11, 16 |
| Reflections collected/unique | 29505/8078 [$^aR(int) = 0.0621$] |
| Reflections [I > 2σ] | 6299 |
| Completeness to theta_max | 0.994 |
| Absorption correction type | multi-scan |
| Max. and min. transmission | 0.996, 0.886 |
| Refinement method: | Full-matrix least-squares on F$^2$ |
| Data/restraints/parameters | 8078/1/928 |
| $^b$Goodness-of-fit | 1.076 |
| Final R indices [I > 2σ] | $^cR_1 = 0.0619, ^dwR_2 = 0.121$ |
| R indices (all data) | $^cR_1 = 0.086, ^dwR_2 = 0.1312$ |
| Largest diff. peak and hole | 0.531 and −0.3 e · Å$^{-3}$ |

Atomic coordinates, site occupancy (%) and equivalent isotropic displacement parameters (A$^2$×10$^3$).

U(eq) is defined as one third of the trace of the orthogonalized Uij tensor.

Atom numbering of FIG. 2.12.1 corresponds to below table.

| Atom | x | y | z | occ. | U(eq) |
|---|---|---|---|---|---|
| C1 | −0.3818(4) | 0.00999(17) | 0.1577(4) | 1 | 0.0196(9) |
| H1 | −0.3779 | −0.0157 | 0.1054 | 1 | 0.024 |
| C2 | −0.3310(4) | 0.00487(17) | 0.2729(4) | 1 | 0.0193(9) |
| C3 | −0.3588(4) | 0.04946(17) | 0.3333(4) | 1 | 0.0186(9) |
| H3 | −0.4173 | 0.038 | 0.3682 | 1 | 0.022 |
| C4 | −0.4266(4) | 0.08958(17) | 0.2350(4) | 1 | 0.0172(9) |
| H4 | −0.5126 | 0.0945 | 0.2325 | 1 | 0.021 |
| C5 | −0.4453(4) | 0.06061(18) | 0.1208(4) | 1 | 0.0183(9) |
| C6 | −0.5832(4) | 0.0587(2) | 0.0314(4) | 1 | 0.0298(11) |
| H6A | −0.627 | 0.0292 | 0.0483 | 1 | 0.036 |
| H6B | −0.6271 | 0.091 | 0.0347 | 1 | 0.036 |
| C7 | −0.5836(6) | 0.0525(3) | −0.0867(5) | 1 | 0.0523(19) |
| H7A | −0.6431 | 0.0772 | −0.1428 | 1 | 0.063 |
| H7B | −0.6082 | 0.0169 | −0.1162 | 1 | 0.063 |
| C8 | −0.4507(5) | 0.0637(2) | −0.0699(4) | 1 | 0.0287(11) |
| H8A | −0.4066 | 0.0313 | −0.0719 | 1 | 0.034 |
| H8B | −0.4502 | 0.0871 | −0.1318 | 1 | 0.034 |
| N9 | −0.3883(4) | 0.08909(15) | 0.0468(3) | 1 | 0.0179(8) |
| HN9 | −0.406(6) | 0.119(3) | 0.038(6) | 1 | 0.0 |
| C10 | −0.2485(4) | 0.08986(18) | 0.0908(4) | 1 | 0.0211(10) |
| H10A | −0.2248 | 0.1127 | 0.0402 | 1 | 0.025 |
| H10B | −0.2186 | 0.0545 | 0.0856 | 1 | 0.025 |
| C11 | −0.1831(4) | 0.10881(17) | 0.2165(4) | 1 | 0.0176(9) |
| H11A | −0.1748 | 0.0794 | 0.2696 | 1 | 0.021 |
| H11B | −0.0973 | 0.1207 | 0.2312 | 1 | 0.021 |
| C12 | −0.2525(4) | 0.15248(17) | 0.2444(4) | 1 | 0.0165(9) |
| C13 | −0.3674(4) | 0.14288(17) | 0.2526(4) | 1 | 0.0151(9) |
| C14 | −0.4317(4) | 0.18343(17) | 0.2773(4) | 1 | 0.0167(9) |
| H14 | −0.5087 | 0.1775 | 0.2838 | 1 | 0.0 |
| C15 | −0.3799(4) | 0.23192(17) | 0.2919(4) | 1 | 0.0181(9) |
| C16 | −0.2683(4) | 0.24154(17) | 0.2810(4) | 1 | 0.0179(9) |
| C17 | −0.2022(4) | 0.20246(17) | 0.2595(4) | 1 | 0.0175(9) |
| H17 | −0.1243 | 0.209 | 0.2551 | 1 | 0.021 |
| C18 | −0.3495(5) | 0.3174(2) | 0.2989(6) | 1 | 0.0342(13) |
| H18A | −0.3276 | 0.3447 | 0.3591 | 1 | 0.041 |
| H18B | −0.3985 | 0.3333 | 0.2218 | 1 | 0.041 |
| C19 | −0.2286(5) | −0.07362(19) | 0.2749(5) | 1 | 0.0287(11) |
| H19A | −0.3051 | −0.09 | 0.218 | 1 | 0.043 |
| H19B | −0.1753 | −0.0999 | 0.329 | 1 | 0.043 |
| H19C | −0.1826 | −0.0574 | 0.2342 | 1 | 0.043 |
| C21 | −0.2376(4) | 0.07232(16) | 0.5324(4) | 1 | 0.0150(9) |
| C22 | −0.1193(4) | 0.10173(17) | 0.6134(4) | 1 | 0.0181(9) |
| C23 | −0.1290(4) | 0.15962(16) | 0.5815(4) | 1 | 0.0210(10) |
| H23A | −0.0436 | 0.1748 | 0.6184 | 1 | 0.025 |
| H23B | −0.1574 | 0.1625 | 0.4961 | 1 | 0.025 |
| C24 | −0.2154(4) | 0.19169(17) | 0.6156(4) | 1 | 0.0191(9) |
| C25 | −0.4265(5) | 0.2160(2) | 0.5670(5) | 1 | 0.0293(12) |
| H25A | −0.4225 | 0.2098 | 0.645 | 1 | 0.044 |
| H25B | −0.5115 | 0.2084 | 0.5085 | 1 | 0.044 |
| H25C | −0.4059 | 0.2523 | 0.5602 | 1 | 0.044 |
| C31 | −0.0033(4) | 0.07965(17) | 0.6007(4) | 1 | 0.0186(9) |
| H31A | −0.0119 | 0.0866 | 0.5206 | 1 | 0.022 |
| H31B | 0.0725 | 0.0983 | 0.6551 | 1 | 0.022 |
| C32 | 0.0168(4) | 0.02207(17) | 0.6244(4) | 1 | 0.0219(10) |
| H32A | −0.059 | 0.003 | 0.5716 | 1 | 0.026 |
| H32B | 0.0297 | 0.0148 | 0.7056 | 1 | 0.026 |
| C33 | 0.1312(4) | 0.00353(17) | 0.6058(4) | 1 | 0.0203(10) |
| H33A | 0.2055 | 0.0237 | 0.6578 | 1 | 0.024 |
| H33B | 0.117 | 0.0115 | 0.5246 | 1 | 0.024 |
| C34 | 0.1622(4) | −0.05425(18) | 0.6277(4) | 1 | 0.0224(10) |
| C35 | 0.0526(5) | −0.0876(2) | 0.5504(5) | 1 | 0.0333(12) |
| H35A | 0.0218 | −0.0755 | 0.4698 | 1 | 0.05 |
| H35B | −0.0153 | −0.0853 | 0.5766 | 1 | 0.05 |
| H35C | 0.0803 | −0.1237 | 0.555 | 1 | 0.05 |
| C36 | 0.2022(6) | −0.0690(2) | 0.7544(5) | 1 | 0.0418(14) |
| H36A | 0.2289 | −0.1053 | 0.7657 | 1 | 0.063 |
| H36B | 0.1312 | −0.0643 | 0.7756 | 1 | 0.063 |
| H36C | 0.2724 | −0.0469 | 0.8038 | 1 | 0.063 |
| O1 | −0.2627(3) | −0.03428(12) | 0.3396(3) | 1 | 0.0245(7) |
| O2 | −0.4215(3) | 0.27736(13) | 0.3215(3) | 1 | 0.0295(8) |
| O3 | −0.2371(3) | 0.29334(12) | 0.3015(3) | 1 | 0.0291(8) |
| O4 | −0.2456(3) | 0.07096(12) | 0.4237(3) | 1 | 0.0193(7) |
| O5 | −0.3115(3) | 0.05224(13) | 0.5638(3) | 1 | 0.0272(8) |
| O6 | −0.1014(3) | 0.09442(13) | 0.7304(3) | 1 | 0.0232(7) |
| HO6 | −0.159(6) | 0.100(3) | 0.736(6) | 1 | 0.05 |
| O7 | −0.1806(3) | 0.22291(14) | 0.6937(3) | 1 | 0.0343(9) |
| O8 | −0.3364(3) | 0.18247(12) | 0.5481(3) | 1 | 0.0231(7) |
| O9 | 0.2605(3) | −0.06667(14) | 0.5922(4) | 1 | 0.0349(9) |
| HO9 | 0.319(6) | −0.049(3) | 0.633(6) | 1 | 0.05 |
| C41 | −0.4061(4) | 0.20979(18) | −0.0709(4) | 1 | 0.0185(9) |
| C42 | −0.4133(4) | 0.26758(17) | −0.0845(4) | 1 | 0.0190(9) |
| C43 | −0.4734(4) | 0.29825(18) | −0.0317(4) | 1 | 0.0236(10) |
| C44 | −0.4734(5) | 0.3520(2) | −0.0387(5) | 1 | 0.0348(13) |
| H44 | −0.5137 | 0.3723 | −0.0014 | 1 | 0.042 |
| C45 | −0.4139(5) | 0.3755(2) | −0.1008(5) | 1 | 0.0361(13) |
| H45 | −0.4138 | 0.4122 | −0.106 | 1 | 0.043 |
| C46 | −0.3542(5) | 0.3463(2) | −0.1557(5) | 1 | 0.0320(12) |
| H46 | −0.3132 | 0.3627 | −0.1977 | 1 | 0.038 |
| C47 | −0.3558(4) | 0.2929(2) | −0.1480(4) | 1 | 0.0252(11) |
| H47 | −0.3169 | 0.2728 | −0.1868 | 1 | 0.03 |
| O41 | −0.3392(3) | 0.18505(13) | −0.1087(3) | 1 | 0.0267(8) |
| O42 | −0.4676(3) | 0.18943(12) | −0.0187(3) | 1 | 0.0218(7) |
| O43 | −0.5327(4) | 0.27633(14) | 0.0297(4) | 1 | 0.0331(9) |
| HO43 | −0.525(6) | 0.249(3) | 0.031(6) | 1 | 0.05 |
| C51 | 0.0847(4) | 0.26596(17) | −0.0909(4) | 1 | 0.0198(10) |
| H51 | 0.0267 | 0.2505 | −0.161 | 1 | 0.024 |
| C52 | 0.1215(4) | 0.31517(18) | −0.0810(4) | 1 | 0.0200(10) |
| C53 | 0.2190(4) | 0.32915(16) | 0.0374(4) | 1 | 0.0164(9) |
| H53 | 0.3014 | 0.3357 | 0.0333 | 1 | 0.02 |
| C54 | 0.2289(4) | 0.27955(16) | 0.1123(4) | 1 | 0.0136(9) |
| H54 | 0.3181 | 0.2674 | 0.1417 | 1 | 0.016 |
| C55 | 0.1468(4) | 0.23828(16) | 0.0226(4) | 1 | 0.0142(8) |
| C56 | 0.2210(4) | 0.18952(17) | 0.0199(4) | 1 | 0.0199(9) |
| H56A | 0.2763 | 0.1964 | −0.0202 | 1 | 0.024 |
| H56B | 0.2728 | 0.1769 | 0.0997 | 1 | 0.024 |
| C57 | 0.1175(4) | 0.15039(18) | −0.0484(4) | 1 | 0.0243(10) |
| H57A | 0.0894 | 0.1551 | −0.1334 | 1 | 0.029 |
| H57B | 0.148 | 0.1144 | −0.0276 | 1 | 0.029 |
| C58 | 0.0111(4) | 0.16215(17) | −0.0123(4) | 1 | 0.0216(10) |
| H58A | 0.0026 | 0.134 | 0.0371 | 1 | 0.026 |
| H58B | −0.0697 | 0.166 | −0.0817 | 1 | 0.026 |
| N59 | 0.0475(3) | 0.21301(14) | 0.0560(3) | 1 | 0.0161(8) |
| HN59 | 0.088(5) | 0.199(2) | 0.139(5) | 1 | 0.05 |
| C60 | −0.0649(4) | 0.24526(18) | 0.0388(4) | 1 | 0.0199(10) |

-continued

| Atom | x | y | z | occ. | U(eq) |
|---|---|---|---|---|---|
| H60A | −0.1166 | 0.2267 | 0.0718 | 1 | 0.024 |
| H60B | −0.1165 | 0.2495 | −0.0458 | 1 | 0.024 |
| C61 | −0.0319(4) | 0.29898(18) | 0.0951(4) | 1 | 0.0188(9) |
| H61A | −0.0155 | 0.3225 | 0.0412 | 1 | 0.023 |
| H61B | −0.1057 | 0.3126 | 0.1056 | 1 | 0.023 |
| C62 | 0.0809(4) | 0.29972(16) | 0.2115(4) | 1 | 0.0143(9) |
| C63 | 0.2020(4) | 0.28854(16) | 0.2193(4) | 1 | 0.0135(8) |
| C64 | 0.3049(4) | 0.28691(17) | 0.3276(4) | 1 | 0.0156(9) |
| H64 | 0.3865 | 0.2784 | 0.3338 | 1 | 0.019 |
| C65 | 0.2853(4) | 0.29777(17) | 0.4240(4) | 1 | 0.0179(9) |
| C66 | 0.1677(4) | 0.31120(17) | 0.4167(4) | 1 | 0.0197(10) |
| C67 | 0.0638(4) | 0.31097(16) | 0.3130(4) | 1 | 0.0188(9) |
| H67 | −0.0174 | 0.3182 | 0.3094 | 1 | 0.023 |
| C68 | 0.3079(5) | 0.3226(2) | 0.6008(4) | 1 | 0.0320(12) |
| H68A | 0.3372 | 0.3589 | 0.6181 | 1 | 0.038 |
| H68B | 0.3258 | 0.3046 | 0.6753 | 1 | 0.038 |
| C69 | −0.0155(6) | 0.3400(2) | −0.2692(5) | 1 | 0.0428(15) |
| H69A | 0.014 | 0.314 | −0.3086 | 1 | 0.064 |
| H69B | −0.0446 | 0.3707 | −0.3186 | 1 | 0.064 |
| H69C | −0.0852 | 0.3256 | −0.2545 | 1 | 0.064 |
| C71 | 0.2427(4) | 0.41910(16) | 0.0877(4) | 1 | 0.0159(9) |
| C72 | 0.2104(5) | 0.45689(17) | 0.1661(5) | 1 | 0.0244(11) |
| C73 | 0.2446(5) | 0.4339(2) | 0.2868(4) | 1 | 0.0288(11) |
| H73A | 0.2371 | 0.4613 | 0.3385 | 1 | 0.035 |
| H73B | 0.1834 | 0.4063 | 0.2808 | 1 | 0.035 |
| C74 | 0.3766(5) | 0.4115(2) | 0.3417(4) | 1 | 0.0286(11) |
| C75 | 0.5447(5) | 0.3850(3) | 0.5159(5) | 1 | 0.0448(15) |
| H75A | 0.5447 | 0.3514 | 0.4801 | 1 | 0.067 |
| H75B | 0.5651 | 0.3802 | 0.5988 | 1 | 0.067 |
| H75C | 0.6078 | 0.4076 | 0.5075 | 1 | 0.067 |
| C81 | 0.0688(5) | 0.46846(19) | 0.1066(5) | 1 | 0.0297(12) |
| H81A | 0.0225 | 0.4358 | 0.1018 | 1 | 0.036 |
| H81B | 0.0477 | 0.4926 | 0.1566 | 1 | 0.036 |
| C82 | 0.0219(5) | 0.4915(2) | −0.0146(5) | 1 | 0.0379(14) |
| H82A | 0.0717 | 0.477 | −0.0546 | 1 | 0.045 |
| H82B | 0.0364 | 0.5294 | −0.0077 | 1 | 0.045 |
| C83 | −0.1172(5) | 0.4814(2) | −0.0889(5) | 1 | 0.0378(13) |
| H83A | −0.1271 | 0.4443 | −0.111 | 1 | 0.045 |
| H83B | −0.1636 | 0.4874 | −0.0399 | 1 | 0.045 |
| C84 | −0.1788(5) | 0.5126(2) | −0.1973(5) | 1 | 0.0353(13) |
| C85 | −0.3125(6) | 0.4957(3) | −0.2704(6) | 1 | 0.0532(17) |
| H85A | −0.3601 | 0.4953 | −0.2222 | 1 | 0.08 |
| H85B | −0.3123 | 0.4609 | −0.3012 | 1 | 0.08 |
| H85C | −0.352 | 0.52 | −0.3352 | 1 | 0.08 |
| C86 | −0.1053(6) | 0.5173(3) | −0.2700(5) | 1 | 0.0439(15) |
| H86A | −0.1535 | 0.5378 | −0.3398 | 1 | 0.066 |
| H86B | −0.0895 | 0.4828 | −0.2931 | 1 | 0.066 |
| H86C | −0.0248 | 0.5345 | −0.2246 | 1 | 0.066 |
| O51 | 0.0848(3) | 0.35381(13) | −0.1615(3) | 1 | 0.0285(8) |
| O52 | 0.3708(3) | 0.29717(14) | 0.5395(3) | 1 | 0.0264(8) |
| O53 | 0.1754(3) | 0.32134(13) | 0.5276(3) | 1 | 0.0260(7) |
| O54 | 0.1836(3) | 0.37380(11) | 0.0855(3) | 1 | 0.0184(7) |
| O55 | 0.3039(3) | 0.42839(12) | 0.0351(3) | 1 | 0.0225(7) |
| O56 | 0.2839(4) | 0.50176(14) | 0.1739(4) | 1 | 0.0364(9) |
| HO56 | 0.272(6) | 0.531(3) | 0.200(6) | 1 | 0.05 |
| O57 | 0.4356(3) | 0.39631(15) | 0.2885(3) | 1 | 0.0382(9) |
| O58 | 0.4187(4) | 0.40908(16) | 0.4575(3) | 1 | 0.0409(10) |
| O59 | −0.1879(3) | 0.56408(15) | −0.1531(4) | 1 | 0.0467(10) |
| H59 | −0.2274 | 0.5839 | −0.2093 | 1 | 0.07 |
| C91 | 0.2069(5) | 0.15694(19) | 0.3512(5) | 1 | 0.0274(11) |
| C92 | 0.2274(4) | 0.16464(17) | 0.4767(4) | 1 | 0.0223(10) |
| C93 | 0.1463(3) | 0.19621(14) | 0.5016(3) | 1 | 0.0268(11) |
| H93 | 0.0736 | 0.2099 | 0.4399 | 1 | 0.032 |
| C94 | 0.1706(3) | 0.20812(14) | 0.6171(3) | 1 | 0.0321(12) |
| H94 | 0.1166 | 0.2309 | 0.6341 | 1 | 0.039 |
| C95 | 0.2751(5) | 0.1862(2) | 0.7069(3) | 1 | 0.0376(13) |
| H95 | 0.2916 | 0.1937 | 0.7856 | 1 | 0.045 |
| C96 | 0.3549(5) | 0.1536(2) | 0.6824(5) | 1 | 0.0340(13) |
| H96 | 0.4255 | 0.1386 | 0.7441 | 1 | 0.041 |
| C97 | 0.3320(5) | 0.1430(2) | 0.5688(5) | 1 | 0.0286(11) |
| O91 | 0.1084(3) | 0.17337(13) | 0.2713(3) | 1 | 0.0265(8) |
| O92 | 0.2952(4) | 0.13363(15) | 0.3347(3) | 1 | 0.0370(9) |
| O93 | 0.4150(3) | 0.11174(15) | 0.5479(4) | 1 | 0.0363(9) |
| HO93 | 0.369(6) | 0.114(3) | 0.462(6) | 1 | 0.05 |
| OW1 | 0.4458(4) | 0.01162(15) | 0.6698(4) | 1 | 0.0458(10) |
| OW2 | 0.6810(3) | 0.11024(14) | 0.7538(3) | 1 | 0.0318(8) |

The invention claimed is:

1. A crystalline homoharringtonine salt of Formula (I)

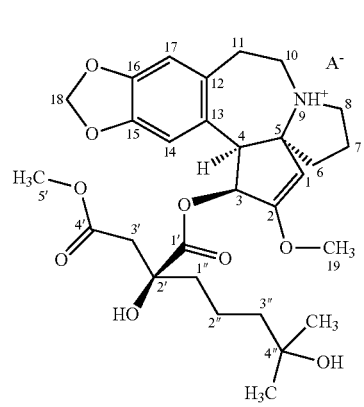

Formula (I)

or solvate thereof, wherein the homoharringtonine is protonated on the nitrogen and $A^−$ represents an organic acid anion selected from the group consisting of fumarate, maleate, citramalate, malate, tartrate, tartronate, succinate, itaconate or citrate, obtained by separately dissolving a compound of formula (II)

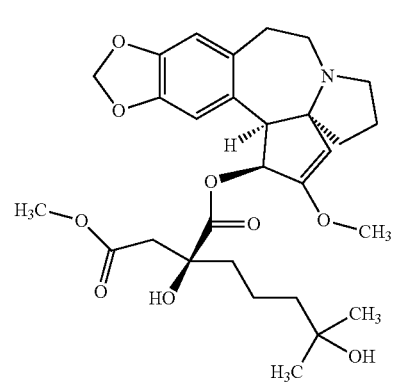

Formula (II)

and an organic acid AH selected from the group consisting of fumaric acid, maleic acid, citramalic acid, malic acid, tartaric acid, tartronic acid, succinic acid, itaconic acid or citric acid, in methanol at a concentration close to saturation and at a temperature close to the boiling point of methanol, to obtain two methanolic solution, mixing both methanolic solutions under stirring, thus obtaining a mixed solution, cooling the mixed solution, evaporating methanol, and collecting the crystalline homoharringtonine salt of formula (I) as defined above after a period ranging from a few minutes up to several days.

2. The salt of claim 1 having following formula

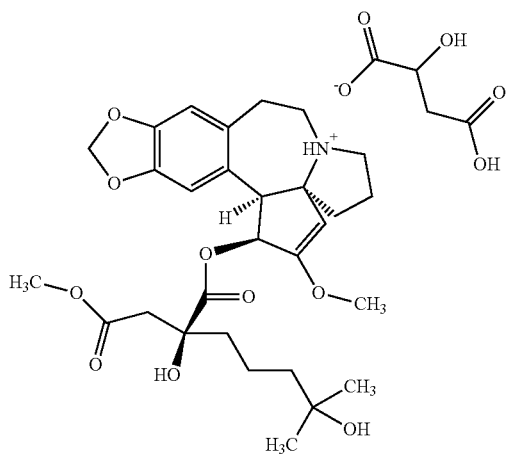

in which the malic acid is of configuration 2S having formula

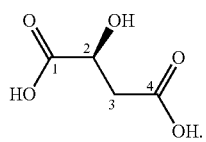

3. The salt of claim 2, in which the malic acid is of configuration 2R having formula

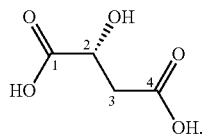

4. The salt of claim 1, wherein the salt is a crystalline salt named (3S,4S,5R,2'R)-homoharringtonine hydrogen (R)-malate exhibiting the following formula:

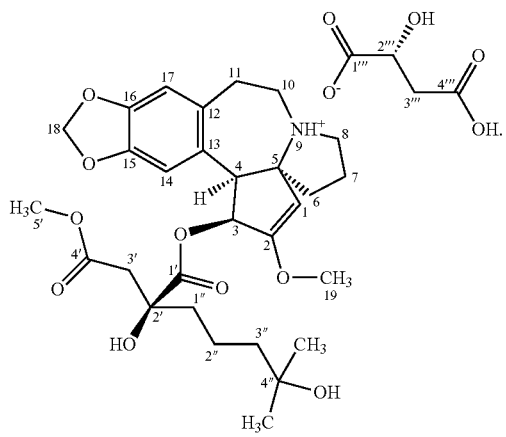

5. The salt of claim 1, wherein the salt is a crystalline salt named (3S,4S,5R,2'R)-homoharringtonine hydrogen succinate exhibiting the following formula:

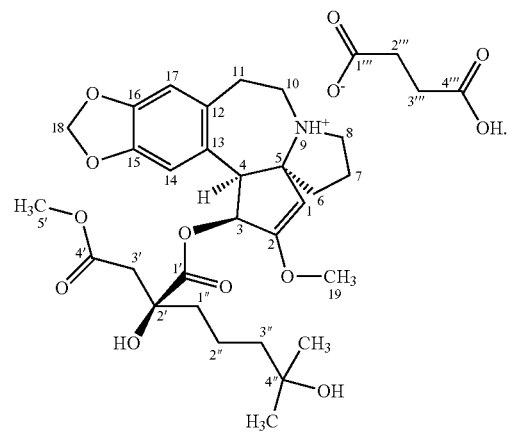

6. The salt of claim 1, wherein the salt is a crystalline salt named (3S,4S,5R,2'R)-homoharringtonine hydrogen (2'''S, 3'''S)-tartrate exhibiting the following formula:

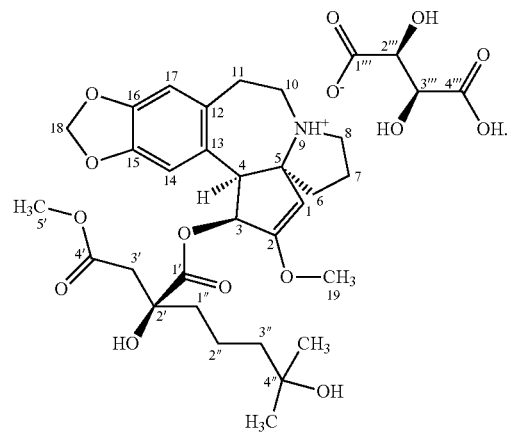

7. The salt of claim 1, wherein the salt is a crystalline salt named (3S,4S,5R,2'R)-homoharringtonine hydrogen (2'''R, 3'''R)-tartrate exhibiting the below formula:

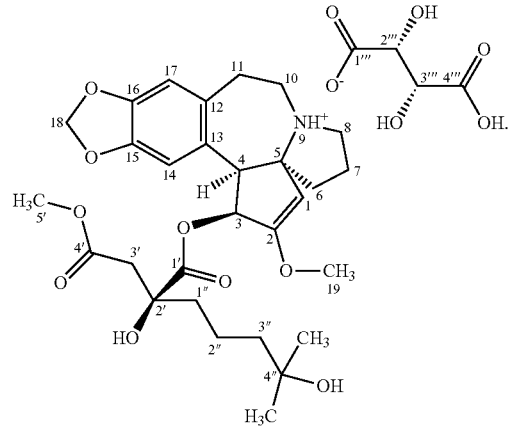

8. The salt of claim 1, The crystalline salt named (3S,4S, 5R,2'R)-homoharringtonine hydrogen itaconate exhibiting the following formula:

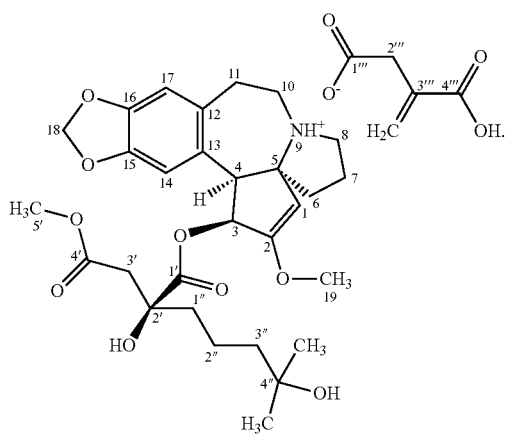

9. The salt of claim 1, wherein the salt is a crystalline salt named (3S,4S,5R,2'R)-homoharringtonine hydrogen fumarate exhibiting the following formula:

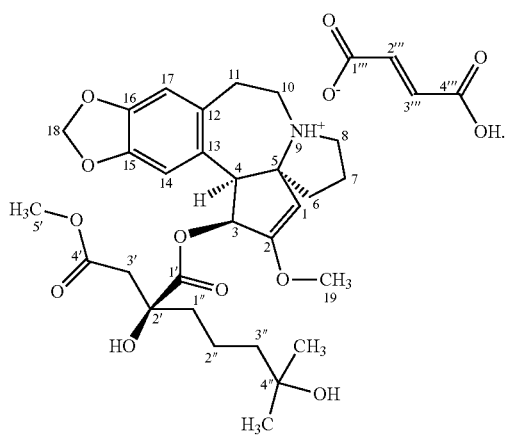

10. The salt of claim 1, wherein the salt is a crystalline salt named (3S,4S,5R,2'R)-homoharringtonine hydrogen tartronate exhibiting the below formula:

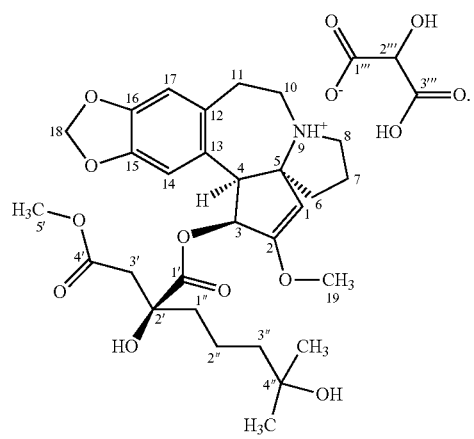

11. The salt of claim 1, wherein the salt is a crystalline salt named (3S,4S,5R,2'R)-homoharringtonine hydrogen malonate exhibiting the following formula:

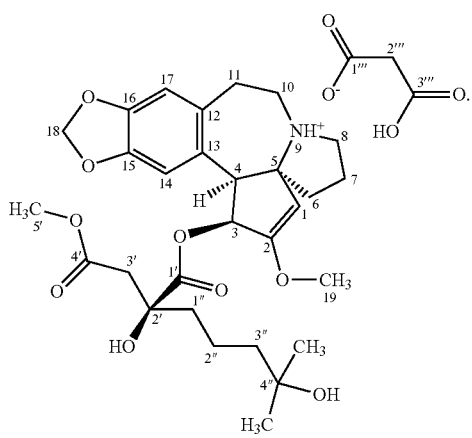

12. The salt of claim 1, wherein the salt is a crystalline salt named (3S,4S,5R,2'R)-homoharringtonine dihydrogen citrate exhibiting the following formula:

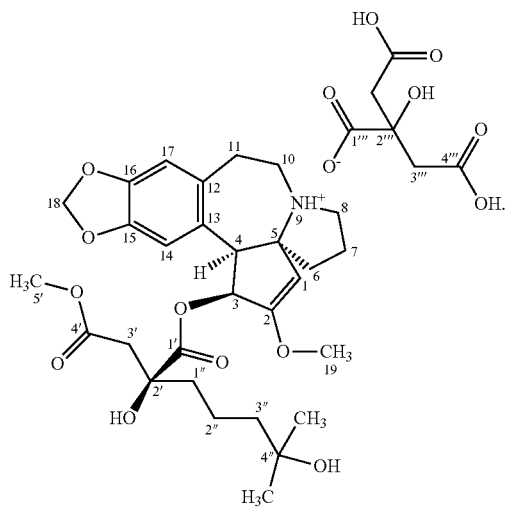

13. The salt of claim 1, wherein the salt is a crystalline salt named (3S,4S,5R,2'R)-homoharringtonine salicate exhibiting the following formula:

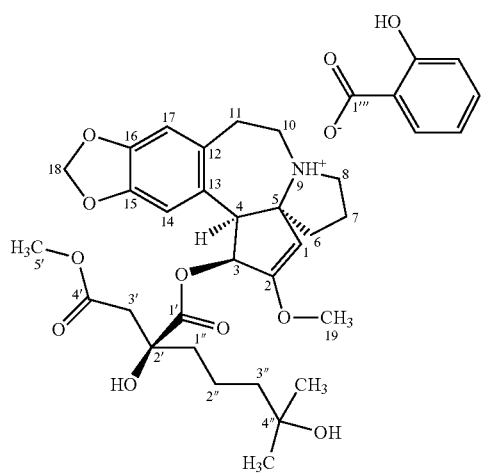

14. The cation (3S,4S,5R,2'R)-homoharringtoninium as described in FIGS. 2.3.1, 2.4.1, 2.5.1, 2.6.1, 2.8.1, 2.9.1, 2.11.1, and 2.12.1, having the following formula (III)

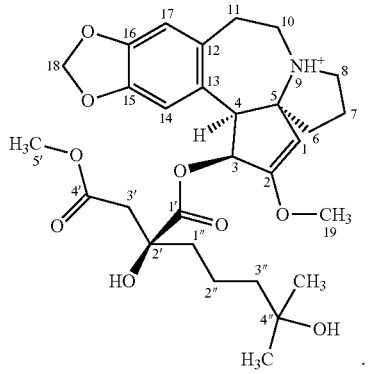

Formula (III)

15. A process for preparing and purifying the salt of claim 1, comprising:
    contacting a natural, hemi-synthetic or synthetic homoharringtonine with acid AH as defined in claim 1, in suspension or in solution in methanol, or mixed at the solid state either at the amorphous state or at the crystalline state,
    recrystallizing said salt in methanol at a concentration close to saturation and at a temperature close to the boiling point of methanol, to obtain two methanolic solution, mixing both methanolic solutions under stirring, thus obtaining a mixed solution, cooling the mixed solution, evaporating methanol, and collecting the crystalline homoharringtonine salt of formula (I) as defined above after a period ranging from a few minutes up to several days.

16. The process of claim 15, wherein it comprises fractional crystallization, thereby providing an enantiomerically enriched crystalline homoharringtonine salt.

17. A pharmaceutical dosage form comprising a pharmaceutically acceptable carrier and a therapeutically effective amount the salt of claim 1, or solvate thereof.

* * * * *